United States Patent
Matsumoto et al.

(10) Patent No.: US 11,134,898 B2
(45) Date of Patent: Oct. 5, 2021

(54) ELECTRONIC APPARATUS, INFORMATION PROCESSING APPARATUS, INFORMATION PROCESSING METHOD, AND RECORDING MEDIUM

(71) Applicant: Panasonic Intellectual Property Management Co., Ltd., Osaka (JP)

(72) Inventors: Akinori Matsumoto, Osaka (JP); Koji Morikawa, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 966 days.

(21) Appl. No.: 15/839,916

(22) Filed: Dec. 13, 2017

(65) Prior Publication Data

US 2018/0168514 A1  Jun. 21, 2018

(30) Foreign Application Priority Data

Dec. 20, 2016 (JP) .............................. JP2016-246834

(51) Int. Cl.
| | |
|---|---|
| A61B 5/00 | (2006.01) |
| A61B 5/282 | (2021.01) |
| A61B 5/291 | (2021.01) |
| A61B 5/296 | (2021.01) |
| A61B 5/398 | (2021.01) |

(52) U.S. Cl.
CPC ............ *A61B 5/7214* (2013.01); *A61B 5/282* (2021.01); *A61B 5/291* (2021.01); *A61B 5/296* (2021.01); *A61B 5/398* (2021.01); *A61B 5/6843* (2013.01); *A61B 2562/0209* (2013.01); *A61B 2562/043* (2013.01)

(58) Field of Classification Search
CPC ....... A61B 5/7214; A61B 5/282; A61B 5/291; A61B 5/296; A61B 5/398; A61B 5/6843; A61B 2562/043; A61B 2562/0209
USPC ................................................ 600/547, 421
See application file for complete search history.

(56) References Cited

U.S. PATENT DOCUMENTS

| | | | |
|---|---|---|---|
| 3,742,936 A * | 7/1973 | Blanie .................... | A61B 5/411 600/526 |
| 5,047,930 A * | 9/1991 | Martens ................. | A61B 5/369 600/301 |
| 5,792,063 A | 8/1998 | Danielsson et al. | |

(Continued)

FOREIGN PATENT DOCUMENTS

| | | |
|---|---|---|
| JP | 10-028680 | 2/1998 |
| JP | 2006-506124 | 2/2006 |

(Continued)

*Primary Examiner* — May A Abouelela
(74) *Attorney, Agent, or Firm* — Wenderoth, Lind & Ponack, L.L.P.

(57) ABSTRACT

In the electronic apparatus, a contact impedance compensation controller calculates a first compensation value and a second compensation value so that a resulting value obtained by adding a third resistance value between a measuring electrode and first skin to a first resistance value is equal to a resulting value obtained by adding a fourth resistance value between a reference electrode and second skin to a second resistance value, determines first information on the basis of the first compensation value, determines the second information on the basis of the second compensation value, and sends the first information to the first compensation circuit.

9 Claims, 32 Drawing Sheets

(56) References Cited

U.S. PATENT DOCUMENTS

| | | | | |
|---|---|---|---|---|
| 6,216,027 B1* | 4/2001 | Willis | | A61B 5/287 600/424 |
| 6,385,019 B1* | 5/2002 | Gagne | | A61B 5/296 361/15 |
| 10,226,195 B2* | 3/2019 | Briante | | A61B 5/316 |
| 10,310,680 B2* | 6/2019 | Yang | | A61B 5/282 |
| 2002/0038092 A1* | 3/2002 | Stanaland | | A61B 5/25 600/509 |
| 2006/0116599 A1* | 6/2006 | Davis | | A61B 5/0536 600/547 |
| 2007/0225585 A1* | 9/2007 | Washbon | | A61B 5/6803 600/393 |
| 2008/0275316 A1* | 11/2008 | Fink | | A61B 5/30 600/306 |
| 2009/0024017 A1* | 1/2009 | Ruffini | | A61B 5/296 600/395 |
| 2009/0054758 A1* | 2/2009 | Dunseath | | A61B 5/05 600/421 |
| 2009/0167205 A1* | 7/2009 | Petersen | | H05B 45/00 315/291 |
| 2013/0338529 A1* | 12/2013 | Ishijima | | A61B 5/24 600/547 |
| 2014/0200469 A1* | 7/2014 | Bocko | | A61B 5/0245 600/509 |
| 2014/0333332 A1 | 11/2014 | Matsumoto et al. | | |
| 2017/0049398 A1* | 2/2017 | Hirata | | A61B 5/291 |
| 2018/0206790 A1* | 7/2018 | Oehler | | G01R 27/02 |

FOREIGN PATENT DOCUMENTS

| | | |
|---|---|---|
| JP | 2011-161021 | 8/2011 |
| JP | 2012-095905 | 5/2012 |
| JP | 3183032 U | 4/2013 |
| WO | 2004/043252 | 5/2004 |
| WO | 2011/130291 | 10/2011 |
| WO | 2014/038212 | 3/2014 |

* cited by examiner

FIG. 18

| STATE | ELECTRODE | CONTACT IMPEDANCE | IMPEDANCE COMPENSATION AMOUNT | CONTROL SIGNAL | | | | | | | | | | | SYNTHETIC IMPEDANCE |
|---|---|---|---|---|---|---|---|---|---|---|---|---|---|---|---|
| | | | | Sa0 Sb0 | Sa1 Sb1 | Sa2 Sb2 | Sa3 Sb3 | Sa4 Sb4 | Sa5 Sb5 | Sa6 Sb6 | Sa7 Sb7 | Sa8 Sb8 | Sa9 Sb9 | Sa10 Sb10 | |
| FIRST STATE | MEASURING ELECTRODE (Ch1) | 10 kΩ | 0 kΩ | H | L | L | L | L | L | L | L | L | L | L | 10 kΩ |
| | REFERENCE ELECTRODE (Ref) | 10 kΩ | 0 kΩ | H | L | L | L | L | L | L | L | L | L | L | 10 kΩ |
| SECOND STATE | MEASURING ELECTRODE (Ch1) | 1000 kΩ | 0 kΩ | H | L | L | L | L | L | L | L | L | L | L | 1000 kΩ |
| | REFERENCE ELECTRODE (Ref) | 10 kΩ | 0 kΩ | H | L | L | L | L | L | L | L | L | L | L | 10 kΩ |
| THIRD STATE (FOURTH STATE) | MEASURING ELECTRODE (Ch1) | 1000 kΩ | 0 kΩ | H | H | L | L | L | L | L | L | L | L | L | 1000 kΩ |
| | REFERENCE ELECTRODE (Ref) | 10 kΩ | 990 kΩ | L | L | L | L | L | L | H | L | L | L | L | 1000 kΩ |

ELECTRONIC APPARATUS, INFORMATION PROCESSING APPARATUS, INFORMATION PROCESSING METHOD, AND RECORDING MEDIUM

BACKGROUND

1. Technical Field

The present disclosure relates to an electronic apparatus, an information processing system, and the like.

2. Description of the Related Art

As a conventional information processing system, an information processing system in which a user attaches an electrode to skin, a test signal (minute electric current) is passed through the user's body from the electrode, and biological information such as brain waves and electrocardiographic waves is obtained by measuring contact impedance of the electrode that is in contact with the user's skin is known (see, for example, Japanese Unexamined Patent Application Publication No. 10-28680).

However, according to the conventional art, commercial alternating current noise (hum noise) overlaps a bioelectric potential waveform obtained in the information processing system when the electrode is about to be detached from the user's skin. The hum noise cannot be completely eliminated when the obtained bioelectric potential waveform is amplified by an amplifier, and therefore a desired bioelectric potential waveform cannot be obtained in the conventional art. In order to measure a bioelectric potential waveform with certain signal quality, the user is undesirably forced to go to the trouble of attaching the electrode again.

SUMMARY

One non-limiting and exemplary embodiment provides an electronic apparatus, an information processing apparatus, an information processing method, and a recording medium that make it possible to measure a bioelectric potential of certain signal quality without forcing a user to go to the trouble of attaching an electrode again.

In one general aspect, the techniques disclosed here feature an electronic apparatus including: a measuring electrode to be made in contact with first skin of a user; a reference electrode to be made in contact with second skin of the user; a first amplifier circuit; a second amplifier circuit; a first compensation circuit including first short lines, first resistances, a first terminal coupled to the measuring electrode, and a second terminal coupled to the first amplifier circuit; a second compensation circuit including second short lines, second resistances, a third terminal coupled to the reference electrode, and a fourth terminal coupled to the second amplifier circuit; and a controller, wherein the first compensation circuit selects one or more third short lines from among the first short lines on a basis of first information, and thereby a first resistance value between the first terminal and the second terminal is determined, wherein the second compensation circuit selects one or more fourth short lines from among the second short lines on a basis of second information, and thereby a second resistance value between the third terminal and the fourth terminal is determined, wherein the first information specifies the one or more third short lines, and the second information specifies the one or more fourth short lines, wherein the controller calculates a first compensation value and a second compensation value so that a resulting value obtained by adding a third resistance value between the measuring electrode and the first skin to the first resistance value is equal to a resulting value obtained by adding a fourth resistance value between the reference electrode and the second skin to the second resistance value, wherein the controller determines the first information on a basis of the first compensation value, wherein the controller determines the second information on a basis of the second compensation value, and wherein the controller sends the first information to the first compensation circuit.

It should be noted that general or specific embodiments may be implemented as a system, a method, an integrated circuit, a computer program, a computer-readable recording medium, or any selective combination thereof. Examples of the computer-readable recording medium include a non-volatile recording medium such as a compact disc-read only memory (CD-ROM).

According to the present disclosure, it is possible to measure a bioelectric potential of certain signal quality without forcing a user to go to the trouble of attaching an electrode again.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 18 illustrates an operation table of the contact impedance compensator according to Embodiment 1;

DETAILED DESCRIPTION

Figure 1:
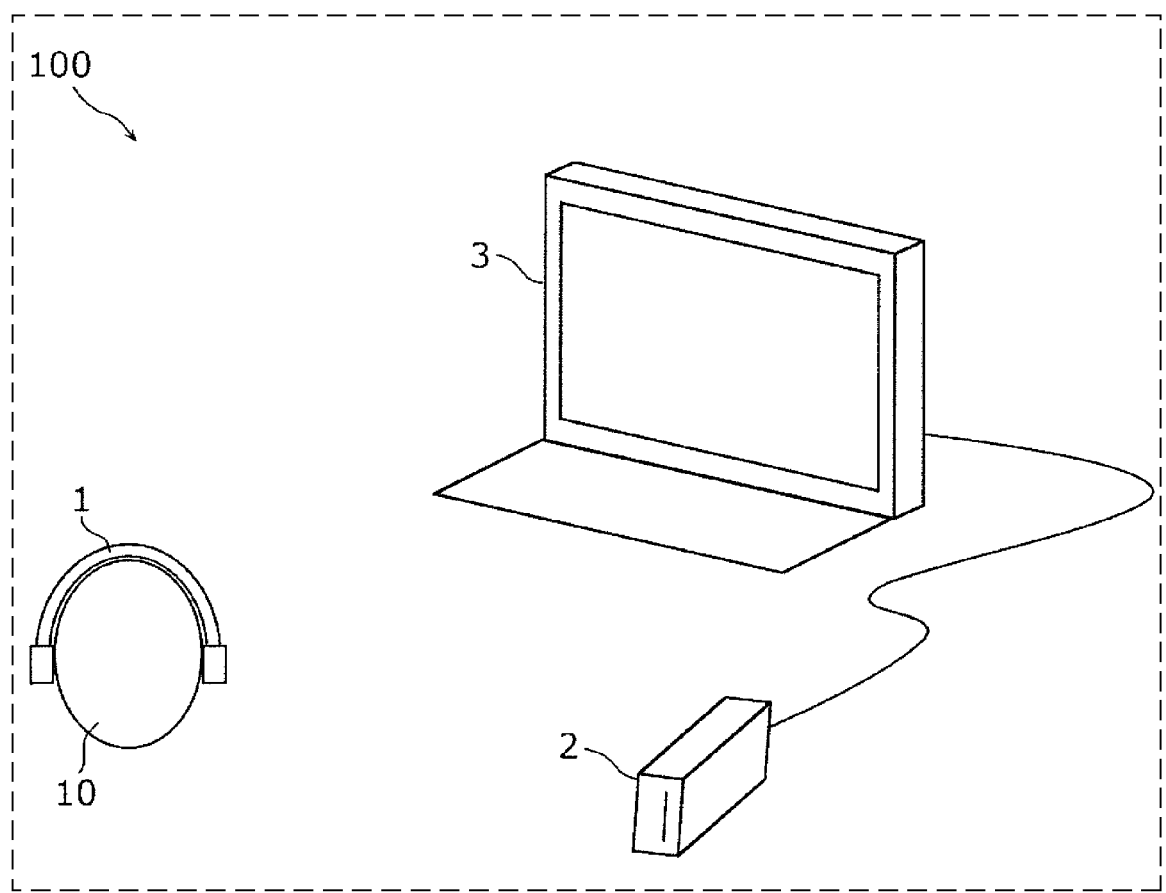
FIG. 1 illustrates a scene where an information processing system according to Embodiment 1 is used.

One aspect of the present disclosure is outlined below.

An electronic apparatus includes: a measuring electrode to be made in contact with first skin of a user; a reference electrode to be made in contact with second skin of the user; a first amplifier circuit; a second amplifier circuit; a first compensation circuit including first short lines, first resistances, a first terminal coupled to the measuring electrode, and a second terminal coupled to the first amplifier circuit; a second compensation circuit including second short lines, second resistances, a third terminal coupled to the reference electrode, and a fourth terminal coupled to the second amplifier circuit; and a controller, wherein the first compensation circuit selects one or more third short lines from among the first short lines on a basis of first information, and thereby a first resistance value between the first terminal and the second terminal is determined, wherein the second compensation circuit selects one or more fourth short lines from among the second short lines on a basis of second information, and thereby a second resistance value between the third terminal and the fourth terminal is determined, wherein the first information specifies the one or more third short lines, and the second information specifies the one or more fourth short lines, wherein the controller calculates a first compensation value and a second compensation value so that a resulting value obtained by adding a third resistance value between the measuring electrode and the first skin to the first resistance value is equal to a resulting value obtained by adding a fourth resistance value between the reference electrode and the second skin to the second resistance value, wherein the controller determines the first information on a basis of the first compensation value, wherein the controller determines the second information on a basis of the second compensation value, and wherein the controller sends the first information to the first compensation circuit.

The electronic apparatus may be arranged such that the first short lines correspond to the first resistances, respectively; the second short lines correspond to the second resistances, respectively; when the third short lines are selected from among the first short lines, both ends of terminals of the first resistances corresponding to the third short lines are short-circuited by the third short lines; and when the fourth short lines are selected from among the second short lines, both ends of terminals of the second resistances corresponding to the fourth short lines are short-circuited by the fourth short lines.

The electronic apparatus may be arranged to further include a first test circuit that is coupled to the measuring electrode and includes a first current source; and a second test circuit that is coupled to the reference electrode and includes a second current source, wherein the controller causes the first current source to output a first current, causes the first amplifier circuit measure a first voltage while the first current is being output, and calculates the third resistance value by using a current value of the first current and a voltage value of the first voltage, and wherein the controller causes the second current source to output a second current, causes the second amplifier circuit to measure a second voltage while the second current is being output, and calculates the fourth resistance value by using a current value of the second current and a voltage value of the second voltage.

The electronic apparatus may be arranged to further include a third compensation circuit that determines a coefficient of compensation of an amplitude of an bioelectric potential on a basis of the third resistance value and the fourth resistance value and compensates the amplitude of the bioelectric potential.

The electronic apparatus may be arranged to further include an operation input unit that receives, from an outside, a sum of the third resistance value and the first compensation value and/or a sum of the fourth resistance value and the second compensation value, wherein the third resistance value and/or the fourth resistance value are/is compensated by using the sum of the third resistance value and the first compensation value and/or the sum of the fourth resistance value and the second compensation value.

The electronic apparatus may be arranged such that the third compensation circuit determines the coefficient of compensation of the amplitude of the bioelectric potential on a basis of a common mode rejection ratio that is ability of removing a signal common to the second terminal and the fourth terminal.

The electronic apparatus may be arranged such that the measuring electrode is a first active electrode including the first amplifier circuit; the reference electrode is a second active electrode including the second amplifier circuit; the measuring electrode further includes a first test circuit and the first compensation circuit; and the reference electrode further includes a second test circuit and the second compensation circuit.

The electronic apparatus may be arranged such that the measuring electrode and the reference electrode each further include an A/D converter and the controller.

The electronic apparatus may be arranged such that the measuring electrode includes a coupling part that couples the measuring electrode to the first compensation circuit; the reference electrode includes a coupling part that couples the reference electrode to the second compensation circuit; the measuring electrode and the reference electrode each have a size surrounded by a first circle having a diameter D; the coupling part of the measuring electrode and the coupling part of the reference electrode each have a size surrounded by a second circle having a diameter P; and D≥P+T+C+A is satisfied where T is a length of the first test circuit and the second test circuit in a direction normal to the first circle, C is a length of the first compensation circuit and the second compensation circuit in the direction normal to the first circle, and A is a length of the first amplifier circuit and the second amplifier circuit in the direction normal to the first circle.

The electronic apparatus may be arranged such that the measuring electrode includes a coupling part that couples the measuring electrode to the first compensation circuit; the reference electrode includes a coupling part that couples the reference electrode to the second compensation circuit; the measuring electrode and the reference electrode each have a size surrounded by a first circle having a diameter D; the coupling part of the measuring electrode and the coupling part of the reference electrode each have a size surrounded by a second circle having a diameter P; and D≥P+T+C is satisfied where T is a length of the first test circuit and the second test circuit in a direction normal to the first circle, and C is a length of the first compensation circuit and the second compensation circuit in the direction normal to the first circle.

An information processing apparatus that receives and processes a bioelectric potential of a user from an electronic apparatus, the bioelectric potential being a first potential between a measuring electrode to be made in contact with first skin of the user and the first skin and a second potential between a reference electrode to be made in contact with second skin of the user and the second skin, the information processing apparatus including: an operation signal acquirer that receives an operation signal transmitted from the electronic apparatus; a bioelectric potential acquirer that acquires the first potential and the second potential; a bioelectric potential processor that compensates at least one of the first potential and the second potential acquired by the bioelectric potential acquirer; and an output unit that presents, to the user, information concerning compensation of the first potential and the second potential, wherein the bioelectric potential acquirer measures a first voltage while a first current is being output from a first current source of a first test circuit provided in the electronic apparatus and measures a second voltage while a second current is being output from a second current source of a second test circuit provided in the electronic apparatus, wherein the bioelectric potential processor calculates a fifth resistance value by using a current value of the first current and a voltage value of the first voltage, calculates a sixth resistance value by using a current value of the second current and a voltage value of the second voltage, calculates a first compensation value and a second compensation value so that a resulting value obtained by adding the fifth resistance value to a seventh resistance value between input and output terminals of a first compensation circuit of the electronic apparatus is equal to a resulting value obtained by adding the sixth resistance value and an eighth resistance value between input and output terminals of a second compensation circuit of the electronic apparatus, wherein the bioelectric potential processor determines first information on a basis of the first compensation value, and determines second information on a basis of the second compensation value, wherein the bioelectric potential processor sets a resistance value between the input and output terminals of the first compensation circuit to the seventh resistance value by sending the first information to the first compensation circuit, and sets a resistance value between the input and output terminals of the second compensation circuit to the eighth resistance value by sending the second information to the second compensation circuit, and wherein the output unit presents, to the user, the fifth resistance value, the sixth resistance value, the first information, and the second information.

Embodiments of an information processing system according to one aspect of the present disclosure are described below with reference to the attached drawings. Each of the embodiments described below illustrates a specific example of the present disclosure. Numerical values, shapes, materials, constituent elements, the way in which the constituent elements are disposed and coupled, steps, the order of steps, and the like in the embodiments below are examples and do not limit the present disclosure. Among constituent elements in the embodiment below, constituent elements that are not described in independent claims indicating highest concepts are described as optional constituent elements.

Each of the drawings is a schematic view and is not necessarily exact illustration. Constituent elements that are substantially identical are given identical reference signs, and repeated description thereof is omitted or simplified.

Embodiment 1

Outline of Information Processing System

An information processing system 100 illustrated in FIG. 1 includes a headset 1, an information processing apparatus 2, and a display unit 3. The headset 1, the information processing apparatus 2, and the display unit 3 are coupled through a wire or wirelessly and transmit and receive information to and from one another.

The headset 1 is configured to serve as an electroencephalograph that will be described later. A plurality of electrodes 51 (see FIGS. 2A and 2B) are attached to the head of a user 10. The plurality of electrodes 51 include a measuring electrode that measures a bioelectric potential and a reference electrode that measures a reference potential used to calculate a difference from the potential measured by the measuring electrode. Furthermore, the headset 1 includes an operation input device 1*a* (see FIG. 5) for input, from the user 10, of operation information for operating the information processing system and thus receives operation for realizing desired processing.

The information processing apparatus 2 receives operation input from the headset 1 and performs predetermined processing. For example, the information processing apparatus 2 may be a computer. The "predetermined processing" as used herein is a generic term for applications executed on a household computer such as game, health management, and educational applications.

The display unit 3 displays a result of processing performed by the information processing apparatus 2. The term "display" as used herein encompasses both output of an image on a display and audio output from a speaker. That is, the display unit 3 is a display and/or a speaker that displays image information or audio information.

Configuration of Headset

Figure 2A:
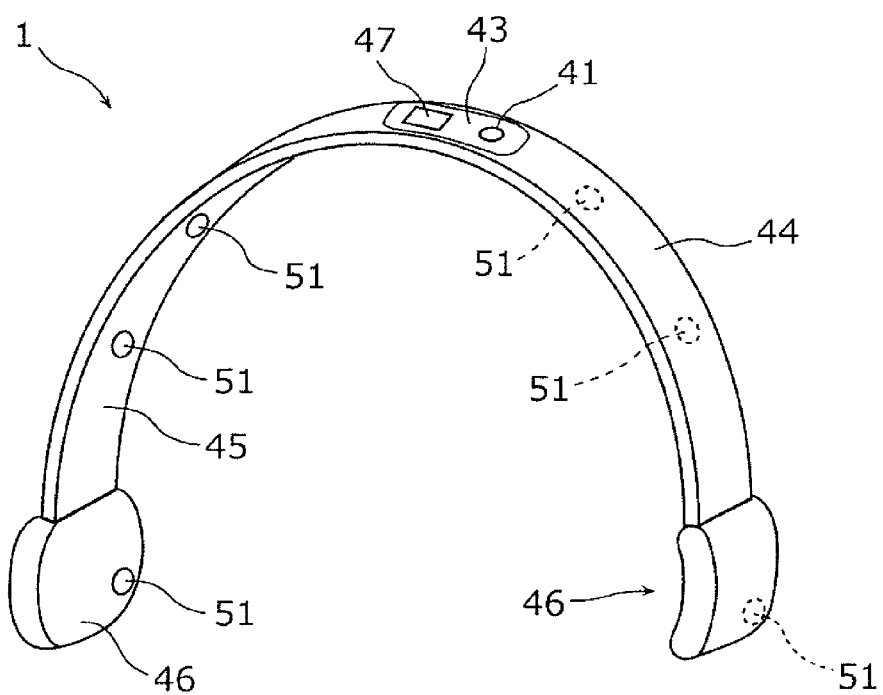
FIG. 2A schematically illustrates a shape and a configuration of a headphone-type headset according to Embodiment 1.
Figure 2B:
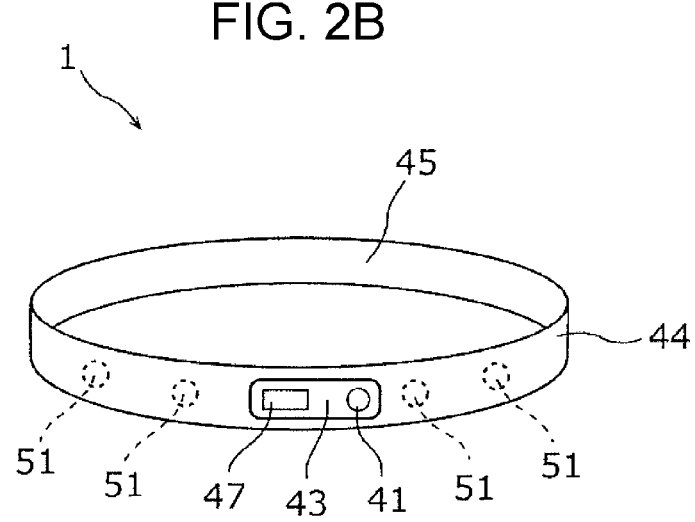
FIG. 2B schematically illustrates a shape and a configuration of a band-type headset.

FIGS. 2A and 2B illustrate an example of a shape and an outline configuration of the headset 1. For example, the user 10 wears the headset 1 on the head. An example of appearance of the headset 1 is a headphone-type in FIG. 2A and a band-type in FIG. 2B.

The headset 1 illustrated in FIG. 2A is a headphone-type headset arched along the head of the user 10. The headphone-type headset 1 illustrated in FIG. 2A includes a plurality of electrodes 51, an outer side surface 44, an attachment surface 45, ear pads 46, and an operation surface 43. The outer side surface 44 is a surface on a side opposite to the head of the user 10 when the user 10 wears the headset 1. The attachment surface 45 is a surface on the head side of the user 10 when the user 10 wears the headset 1. The operation surface 43 includes an operation button 41 and a display unit 47. The plurality of electrodes 51 are provided on the attachment surface 45 of the headset 1 and on ends of surfaces of the ear pads 46 on the same side as the attachment surface 45 of the headset 1.

The user 10 wears the headset 1 on his or her head after activating the headset 1 by operating the operation button 41 disposed on the operation surface 43. The headset 1 is attached to the head of the user 10 so that the ear pad 46 on the left of FIG. 2A is located on the right ear of the user 10 and the ear pad 46 on the right in FIG. 2A is located on the left ear of the user 10. The ear pads 46 are placed so as to cover the left and right ears of the user 10. The electrodes 51 provided on the attachment surface 45 are made in contact with skin (head skin) of the user 10. The electrodes 51 provided at the ends of the ear pads 46 are made in contact with portions behind the ears of the user 10. The electrode 51 provided at the end of the ear pad 46 on the left of FIG. 2A may be an earth electrode that will be described later, the electrode 51 provided at the end of the ear pad 46 on the right of FIG. 2A may be a reference electrode that will be described later, and the other electrodes 51 may be measuring electrodes. Positions where the earth electrode and the reference electrode are disposed are not limited to this example. Alternatively, the electrode 51 provided at the end of the ear pad 46 on the right of FIG. 2A may be an earth electrode, and the electrode 51 provided at the end of the ear pad 46 on the left of FIG. 2A may be a reference electrode.

The operation surface 43 displays, for example, a state of operation and a result of processing of an application on the display unit 47.

The headset 1 illustrated in FIG. 2B is a band-type headset that is wound around the head of the user 10. The band-type headset 1 illustrated in FIG. 2B includes a plurality of electrodes 51, an outer side surface 44, an attachment surface 45, and an operation surface 43. The configurations of the electrodes 51 and the operation surface 43 are similar to those of the headphone-type headset 1. The user 10 activates the headset 1 by operating the operation button 41 disposed on the operation surface 43 before wearing the headset 1 and wears the headset 1 so that a half (the operation surface 43 side) of the outer side surface 44 of the band-type headset 1 is located on the forehead of the user 10. The electrodes 51 are disposed on the attachment surface 45 and are made in contact with the forehead of the user 10. An electrode 51 that serves as an earth electrode and an electrode 51 that serves as a reference electrode among the plurality of electrodes 51 may be configured to be brought into contact with portions behind the ears by extending lead wires (not illustrated) from the attachment surface 45. The operation surface 43 further includes a display unit 47 and can display a state of operation and a result of processing of an application. Note that the earth electrode is not a commonly-acknowledged ground electrode (an electrode having a ground potential), but an electrode having a potential that serves as a reference potential of the user 10.

Electrode Shape

FIGS. 3A through 3E illustrate examples of a shape of a contact surface of each of the electrodes 51 that make contact with skin of the user 10. The electrodes 51 are made of an electrically conductive material. For example, the electrodes 51 are made of gold or silver. Alternatively, the electrodes 51 may be made of silver-silver chloride (Ag/AgCl). This is because silver-silver chloride that is less likely to be polarized when making contact with a biological body and has a stable polarization voltage.

Figure 3A:
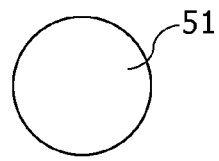
FIG. 3A is a conceptual diagram illustrating a shape of an electrode.
Figure 3B:
FIG. 3B is a conceptual diagram illustrating a shape of an electrode.
Figure 3C:
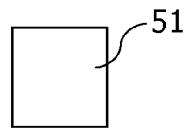
FIG. 3C is a conceptual diagram illustrating a shape of an electrode.

The shape of the contact surface of the electrodes 51 may be a circular shape (e.g., a diameter of 10 mm) illustrated in FIG. 3A, which is similar to an electrode for medical use or may be any one of other various shapes depending on use. For example, the shape of the contact surface of the electrodes 51 may be a triangular shape illustrated in FIG. 3B or may be a quadrangular shape or a square shape illustrated in FIG. 3C.

Figure 3D:
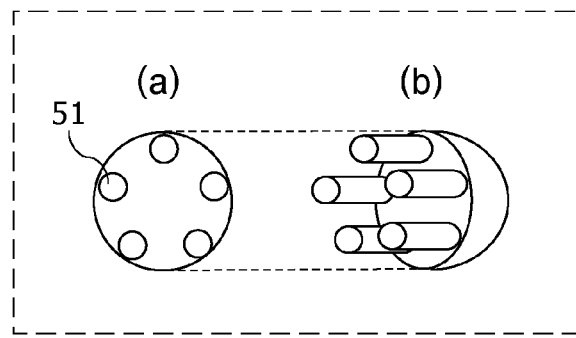
FIG. 3D is a conceptual diagram illustrating a shape of an electrode.

The electrodes 51 disposed on the attachment surface 45 of the headphone-type headset 1 illustrated in FIG. 1 may be electrodes 51 constituted by a plurality of (five in (a) and (b) of FIG. 3D) circular columns as illustrated in (a) and (b) of FIG. 3D. According to this configuration, the electrodes 51 can be made in contact with skin of the user 10 through hair. A contact surface of each circular column with skin may be a circular shape illustrated in (a) of FIG. 3D or may be a different shape such as an oval shape. The electrodes 51 are not limited to circular columns but may be rectangular columns. The number of circular columns or rectangular columns may be five as illustrated in (a) and (b) of FIG. 3D or may be changed. An end of each circular column illustrated in FIG. 3D may be rounded off on the side of the contact surface with skin. This makes it possible to increase the contact area with skin.

Figure 3E:
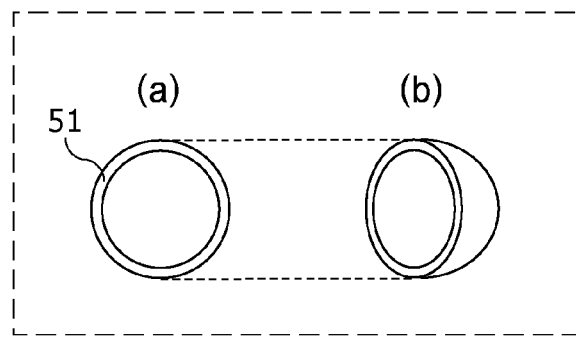
FIG. 3E is a conceptual diagram illustrating a shape of an electrode.

The electrodes 51 may have a concentric contact surface with skin of the user 10 as illustrated in FIG. 3E. The electrodes 51 having this shape are used, for example, for the ear pads 46 of the headphone-type headset 1 illustrated in FIG. 2A or for the band-type headset 1 illustrated in FIG. 2B and are made in contact with hairless portions such as a forehead or portions behind the ears. The electrodes 51 having the shape illustrated in FIG. 3E have less pressure on skin than the electrodes 51 having the shape illustrated in FIG. 3D and therefore cause less burden on the user 10.

Definition of Contact State and Contact Impedance

The contact impedance and contact state of each of the electrodes 51 as used herein are defined as follows. The contact impedance of an electrode as used herein is defined as "a sum of contact impedance of a contact part where the electrode or an electrically conductive object on the electrode is in contact with a skin surface of a body terminal part and body terminal tissue impedance around the contact part". The contact state of the electrode 51 is classified into three states illustrated in FIGS. 4A through 4C depending on a positional relationship between the user 10 and the electrode 51.

Figure 4A:
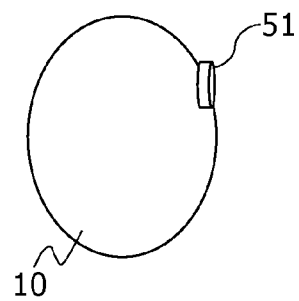
FIG. 4A illustrates a contact state of an electrode and definition of contact impedance.

FIG. 4A illustrates a state where the electrode 51 is "in contact with" the user 10. Typically, a value of contact impedance Rc may be not more than 30 kΩ or not more than 10 kΩ at a frequency of 10 Hz.

Figure 4B:
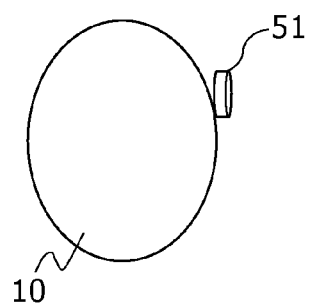
FIG. 4B illustrates a contact state of an electrode and definition of contact impedance.

FIG. 4B illustrates a state where the electrode 51 is "about to be detached from" (weakly in contact with) the user 10, for example, because of a body motion of the user 10. A value of contact impedance Rc of the electrodes 51 in the state illustrated in FIG. 4B is larger than 30 kΩ and smaller than 5 MΩ at a frequency of 10 Hz. The electrodes 51 used herein are dry electrodes that do not use electrically conductive paste, and therefore the state illustrated in FIG. 4B easily occurs, for example, because of a body motion of the user 10.

Figure 4C:
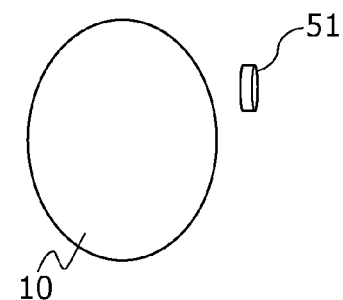
FIG. 4C illustrates a contact state of an electrode and definition of contact impedance.

FIG. 4C illustrates a state where the electrode 51 is "completely detached" from the user 10. Contact impedance in this state is not less than 5 MΩ at a frequency of 10 Hz. The electrode 51 is insulated from the user 10.

Configuration of Information Processing System

Figure 5:
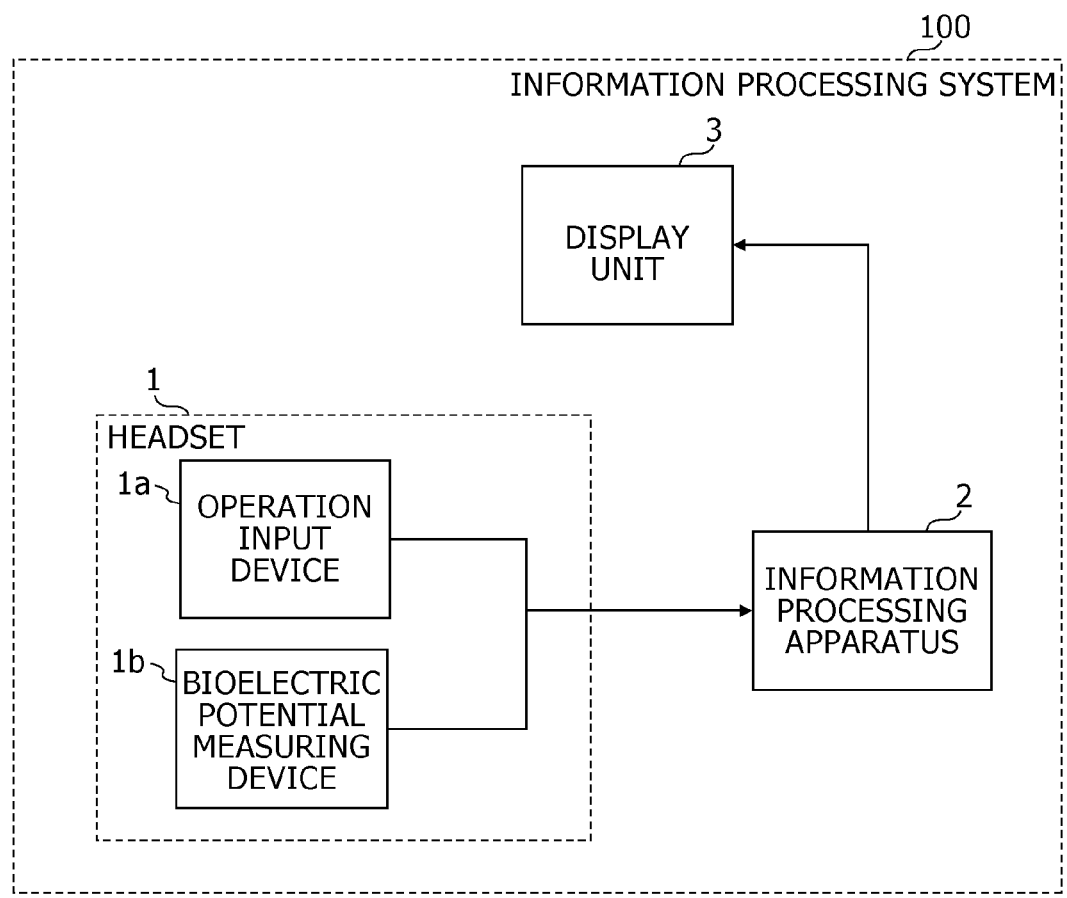
FIG. 5 is a block diagram illustrating an overall configuration of the information processing system according to Embodiment 1.

Next, a configuration of the information processing system 100 is described. FIG. 5 is a block diagram illustrating an overall configuration of the information processing system 100.

As described above, the information processing system 100 includes the headset 1, the information processing apparatus 2, and the display unit 3. The headset 1 includes the operation input device 1a and a bioelectric potential measuring device 1b.

The headset 1 causes the operation input device 1a to receive user 10's operation input and causes the bioelectric potential measuring device 1b to measure a bioelectric potential and contact impedance of the user 10 at the time of the operation. Information including the bioelectric potential measured by the headset 1 is transmitted to the information processing apparatus 2.

The information processing apparatus 2 performs predetermined processing upon receipt of input from the operation input device 1a or the bioelectric potential measuring device 1b and outputs a result of the processing on the display unit 3. The headset 1 and the information processing apparatus 2 are coupled to each other through a wire or wirelessly.

Figure 6:
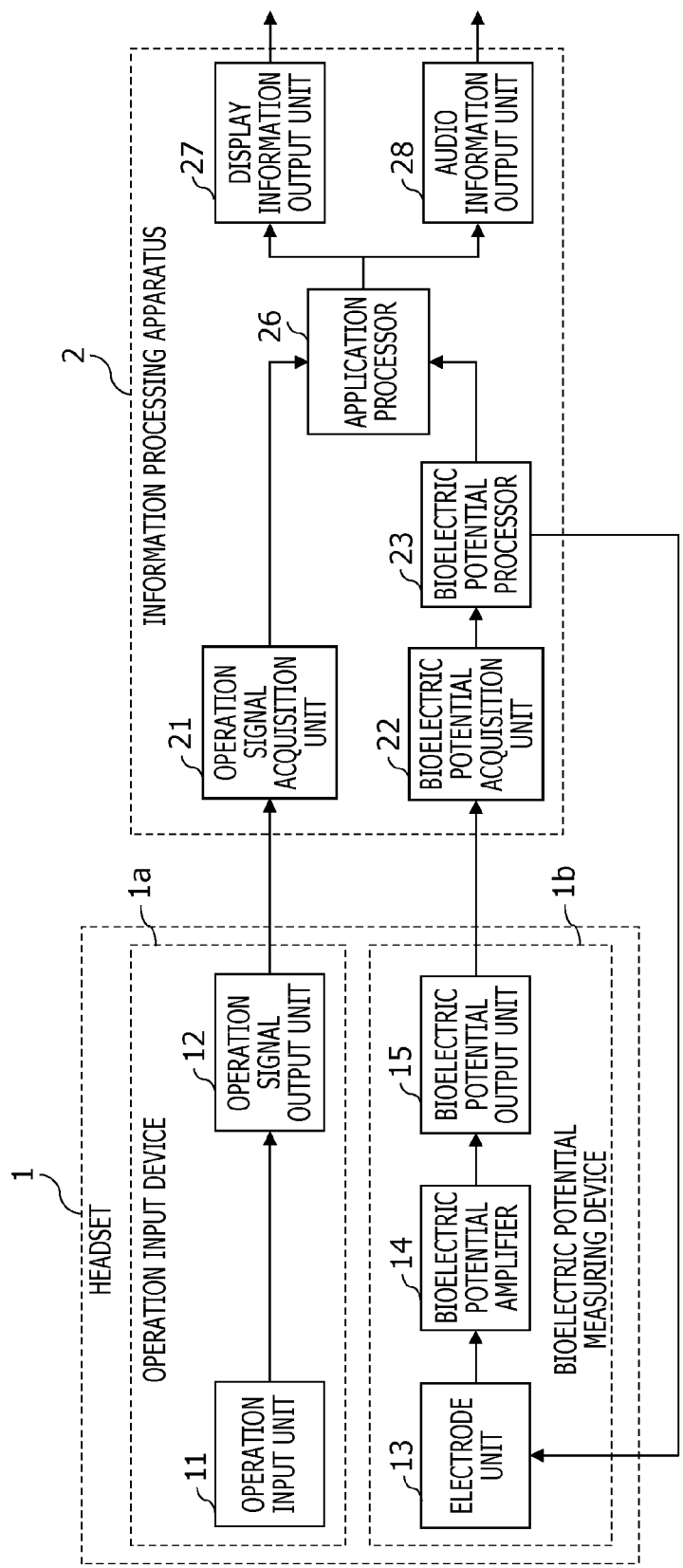
FIG. 6 is a block diagram illustrating detailed configurations of a headset and an information processing apparatus of the information processing system according to Embodiment 1.

FIG. 6 is a block diagram illustrating detailed configurations of the headset 1 and the information processing apparatus 2. The following describes an example in which the headset 1 and the information processing apparatus 2 are coupled to each other wirelessly.

The operation input device 1a included in the headset 1 includes an operation input unit 11 and an operation signal output unit 12.

The operation input unit 11 is an input unit that acquires operation input information input by using the operation button 41 (see FIGS. 2A and 2B) and determines contents of the operation. The operation signal output unit 12 is a transmitter that transmits the operation input information acquired by the operation input unit 11 to the information processing apparatus 2. The operation input information acquired by the operation input unit 11 is transmitted from the operation signal output unit 12 to the information processing apparatus 2.

The bioelectric potential measuring device 1b included in the headset 1 includes an electrode unit 13, a bioelectric potential amplifier 14, and a bioelectric potential output unit 15.

The electrode unit 13 is constituted by the plurality of electrodes 51. The plurality of electrodes 51 include a measuring electrode and a reference electrode as described above. The plurality of electrodes 51 are, for example, disposed so as to be in contact with user's skin.

The bioelectric potential amplifier 14 is an amplifier that amplifies a bioelectric potential corresponding to a potential difference between the plurality of electrodes 51. Specifically, the bioelectric potential amplifier 14 measures a potential difference between a measuring electrode 73a (see FIG. 7) disposed on skin of the user 10 and a reference electrode 73b (see FIG. 7) disposed behind an ear of the user 10 among the plurality of electrodes 51 and amplifies the measured potential difference. The amplified potential difference is, for example, converted into a digital signal by an A/D converter (not illustrated) provided in the bioelectric potential amplifier 14. The bioelectric potential output unit 15 is a transmitter that transmits the potential difference amplified by the bioelectric potential amplifier 14 to the information processing apparatus 2. The potential difference, i.e., the bioelectric potential that has been converted into a digital value by the bioelectric potential amplifier 14 is transmitted from the bioelectric potential output unit 15 to the information processing apparatus 2.

In a case where a bioelectric potential that is equal to or higher than a predetermined potential can be measured, the bioelectric potential amplifier 14 may measure potentials of the plurality of electrodes 51 without need to amplify the bioelectric potential. For this reason, the bioelectric potential amplifier 14 is hereinafter also referred to as a biological signal measuring unit.

The information processing apparatus 2 includes an operation signal acquisition unit 21, a bioelectric potential acquisition unit 22, a bioelectric potential processor 23, an application processor (app processor) 26, a display information output unit 27, and an audio information output unit 28.

The information processing apparatus 2 receives information from the headset 1 by causing the operation signal acquisition unit 21 to receive operation input information and causing the bioelectric potential acquisition unit 22 to receive a bioelectric potential.

The bioelectric potential is often unusable as information while in a recorded state, i.e., an original signal. For this reason, the bioelectric potential processor 23 extracts meaningful information from the original signal. For example, in a case where brain waves are to be measured, a signal of a specific frequency (e.g., 10 Hz) is extracted, and a power spectral density of the signal at this frequency is calculated. The bioelectric potential processor 23 may be disposed not in the information processing apparatus 2 but in the headset 1. In the present embodiment, the headset 1 and the bioelectric potential processor 23 may constitute an electronic apparatus.

The application processor 26 performs main application processing (app processing) of the information processing apparatus 2. The application processing is performed by performing predetermined processing upon receipt of input of a signal from the headset 1. The predetermined processing is, for example, moving a game forward in a game application, recording, data management, and display in a health management application, and questioning, rating, and result display in an educational application.

A result of the processing performed by the application processor 26 is supplied from the application processor 26 to the display information output unit 27 and the audio information output unit 28. The display information output unit 27 and the audio information output unit 28 supplies a visual or auditory signal to the display unit 3 in order to feed the result of the processing performed by the application processor 26 back to the user 10.

The display unit 3 displays the signal supplied from the display information output unit 27 and the audio information output unit 28. In this way, the signal is presented to the user. The display unit 3 is, for example, a television set, a display, or a speaker.

Hardware Configuration

Figure 7:
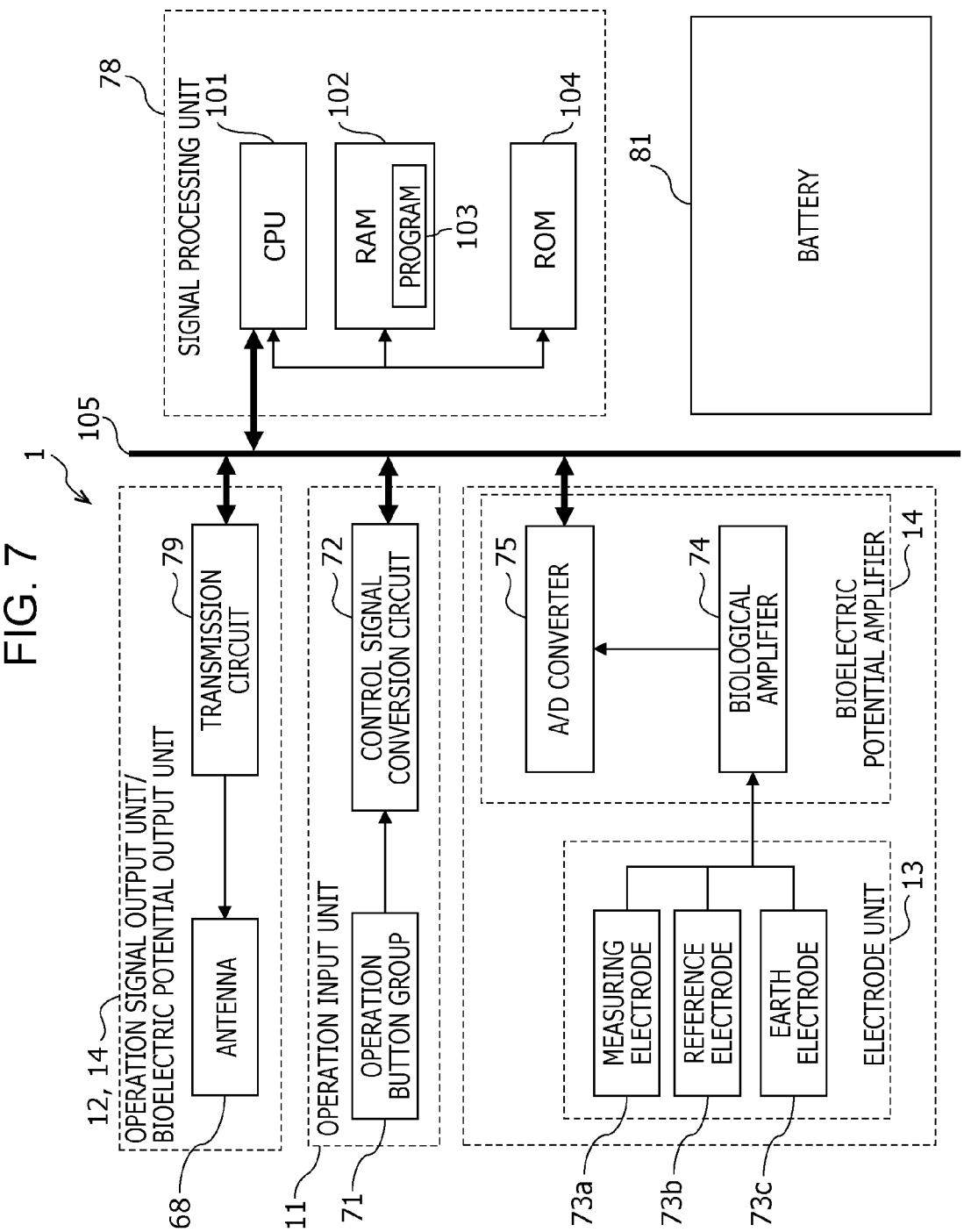
FIG. 7 is a block diagram illustrating a hardware configuration of the headset according to Embodiment 1.

FIG. 7 is a block diagram illustrating a hardware configuration of the headset 1. The headset 1 includes an operation button group 71, a control signal conversion circuit 72, a measuring electrode 73a, a reference electrode 73b, an earth electrode 73c, a biological amplifier 74, an A/D converter 75, a transmission circuit 79, a signal processing unit 78, an antenna 68, and a battery 81.

Among these constituent elements, the operation button group 71 and the control signal conversion circuit 72 correspond to the operation input unit 11 illustrated in FIG. 6. Each button of the operation button group 71 corresponds to the operation button 41. The measuring electrode 73a, the reference electrode 73b, and the earth electrode 73c correspond to the electrodes 51 illustrated in FIGS. 2A and 2B and the electrode unit 13 illustrated in FIG. 6. The biological amplifier 74 corresponds to the bioelectric potential amplifier 14 illustrated in FIG. 6. The A/D converter 75 may be included in the bioelectric potential amplifier 14.

The signal processing unit 78 includes a CPU 101, a RAM 102, a program 103, and a ROM 104. The transmission circuit 79 and the antenna 68 function as the bioelectric potential output unit 15 and/or the operation signal output unit 12 illustrated in FIG. 6. The transmission circuit 79 and the antenna 68 are sometimes referred to as an "output unit" or a "transmitter".

These constituent elements are coupled to one another by a bus 105 and can exchange data with one another. Furthermore, the headset 1 includes the battery 81. Electric power is supplied to each of the aforementioned circuits from the battery 81.

Information concerning pressing of each button of the operation button group 71 is converted into a control signal for controlling operation of the headset 1 by the control signal conversion circuit 72 and is then sent to the CPU 101 through the bus 105.

The measuring electrode 73a, the reference electrode 73b, and the earth electrode 73c are coupled to the biological amplifier 74. These electrodes are disposed at predetermined positions of the headset 1. A potential difference between the measuring electrode 73a and the reference electrode 73b is amplified by the biological amplifier 74 and is then converted from an analog bioelectric potential signal into a digital bioelectric potential signal by the A/D converter 75. The potential difference converted into the digital bioelectric potential signal is sent, as a bioelectric potential signal that can be processed or transmitted, to the CPU 101 through the bus 105.

The CPU 101 executes the program 103 stored in the RAM 102. The program 103 describes a signal processing procedure in the headset 1 illustrated in the flowchart of FIG. 9 that will be described later. The headset 1 converts the operation signal and the bioelectric potential signal into digital signals in accordance with the program 103 and transmits the digital signals from the antenna 68 via the transmission circuit 79. The program 103 may be stored in the ROM 104.

The signal processing unit 78, the control signal conversion circuit 72, the transmission circuit 79, the biological amplifier 74, and the A/D converter 75 may be mounted on a single semiconductor integrated circuit so as to be provided as hardware such as a digital signal processor (DSP) into which a computer program is incorporated. In a case where these constituent elements are mounted on a single semiconductor integrated circuit, it is possible to reduce a mounting area and reduce electric power consumption.

Alternatively, these constituent elements may be provided as hardware such as a DSP into which a computer program is incorporated by integrating the biological amplifier 74 and the A/D converter 75 on a single semiconductor integrated circuit, integrating the signal processing unit 78, the control signal conversion circuit 72, and the transmission circuit 79 on another semiconductor integrated circuit, and then unifying, in a single package, the two semiconductor integrated circuits as a system in package (SiP). By manufacturing the two semiconductor integrated circuits by different manufacturing processes, cost can be lowered as compared with a case where the constituent elements are mounted on a single semiconductor integrated circuit.

Figure 8:
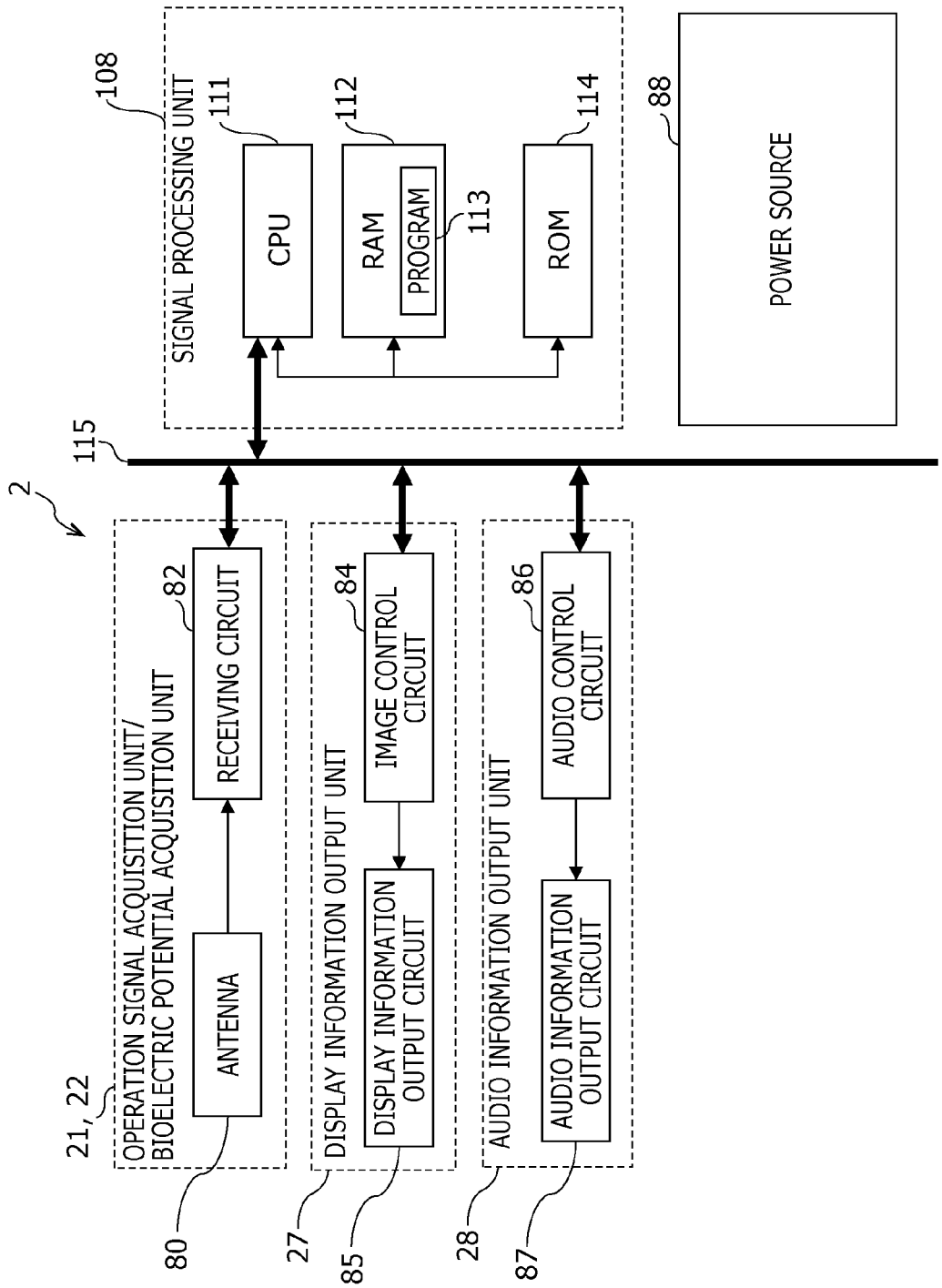
FIG. 8 is a block diagram illustrating a hardware configuration of the information processing apparatus according to Embodiment 1.

FIG. 8 is a block diagram illustrating a hardware configuration of the information processing apparatus 2. The information processing apparatus 2 includes an antenna 80, a receiving circuit 82, a signal processing unit 108, an image control circuit 84, a display information output circuit 85, an audio control circuit 86, an audio information output circuit 87, and a power source 88.

Among these constituent elements, the antenna 80 and the receiving circuit 82 correspond to the bioelectric potential acquisition unit 22 and/or the operation signal acquisition unit 21 illustrated in FIG. 6. The antenna 80 and the receiving circuit 82 are sometimes referred to as a "receiver".

The signal processing unit 108 includes a CPU 111, a RAM 112, a program 113, and a ROM 114. The signal processing unit 108 corresponds to the bioelectric potential processor 23 and/or the application processor 26 illustrated in FIG. 6. The image control circuit 84 and the display information output circuit 85 correspond to the display information output unit 27 illustrated in FIG. 6. The audio control circuit 86 and the audio information output circuit 87 correspond to the audio information output unit 28 illustrated in FIG. 6. These constituent elements are coupled to one another by the bus 115 and can exchange data with one another. Electric power is supplied to each of the circuits from the power source 88.

Operation information and biological information from the headset 1 are received by the receiving circuit 82 via the antenna 80 and is then sent to the CPU 111 through the bus 115.

The CPU 111 executes the program 113 stored in the RAM 112. The program 113 describes a signal processing procedure in the information processing apparatus 2 illustrated in the flowchart of FIG. 9 that will be described later. The information processing apparatus 2 converts an operation signal and a bioelectric potential signal in accordance with the program 113, performs processing for executing a predetermined application, and generates a signal for giving feedback to the user 10 by using an image and/or sound. The program 113 may be stored in the ROM 114.

The image feedback signal generated by the signal processing unit 108 is supplied from the display information output circuit 85 to the display unit 3 via the image control circuit 84. Similarly, the audio feedback signal generated by the signal processing unit 108 is supplied from the audio information output circuit 87 via the audio control circuit 86.

The signal processing unit 108, the receiving circuit 82, the image control circuit 84, and the audio control circuit 86 may be mounted on a single semiconductor integrated circuit so as to be provided as hardware such as a DSP into which a program is incorporated. In a case where these constituent elements are mounted on a single semiconductor integrated circuit, it is possible to reduce electric power consumption.

Outline of Processing Flow of Information Processing System

Figure 9:
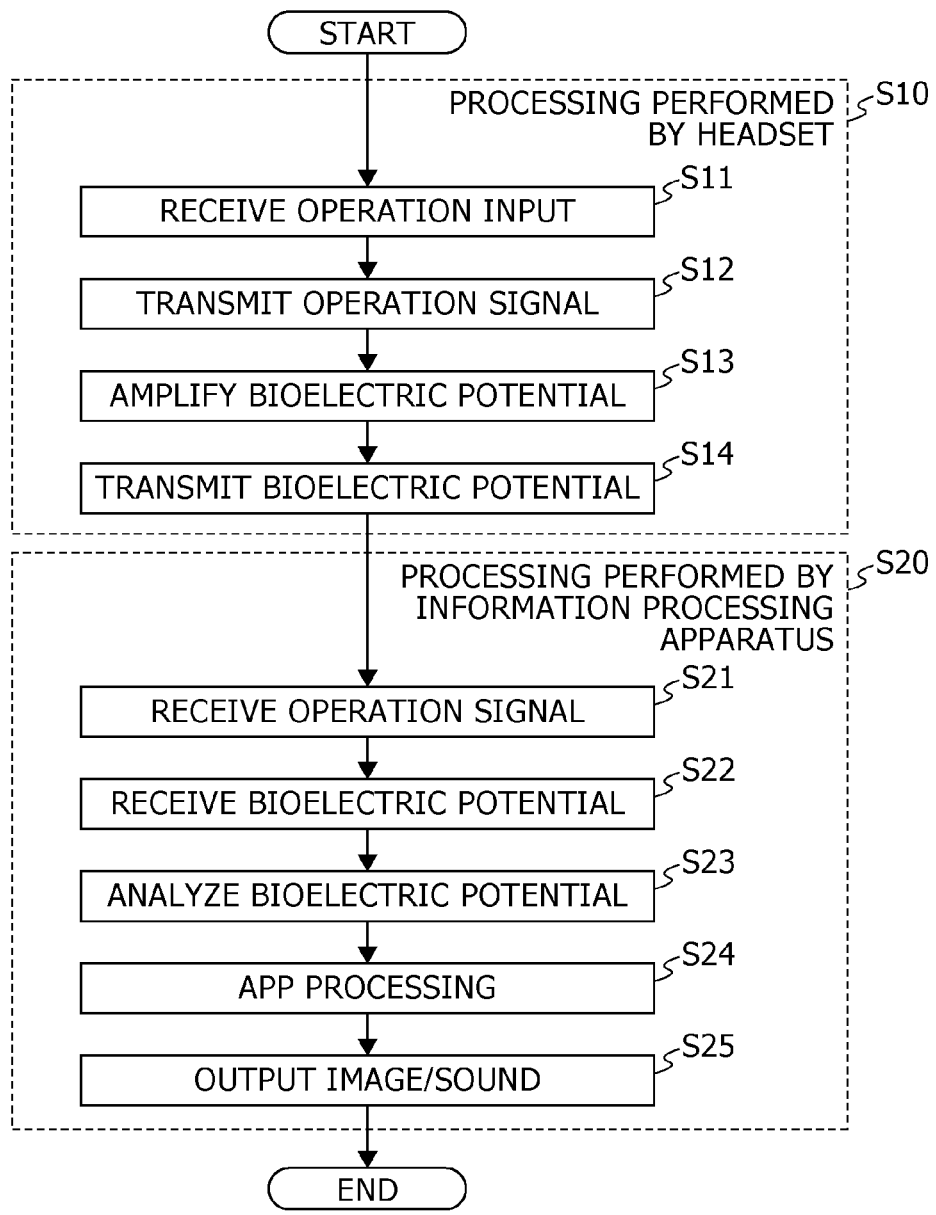
FIG. 9 is a flowchart illustrating a basic processing flow of the headset and the information processing apparatus according to Embodiment 1.

FIG. 9 is a flowchart illustrating flow of basic processing of the headset 1 and the information processing apparatus 2. Steps S11 through S14 are processes in the headset 1 (Step S10), and Steps S21 through S25 are processes in the information processing apparatus 2 (Step S20).

First, processing step S10 in the headset 1 is described.

Step S11

The operation input unit 11 receives user 10's operation input. Specifically, the operation input unit 11 detects which operation button 41 has been pressed at a time of the reception. An example of the time of the reception is a timing at which the operation button 41 is pressed. Whether or not the operation button 41 has been pressed is detected, for example, by detecting a mechanical change of a button position or a change of an electric signal that occurs when the operation button 41 is pressed. Furthermore, the operation input unit 11 detects a kind of operation input received by the operation input unit 11 on the basis of a kind of the pressed operation button 41 and transmits the kind of operation input to the operation signal output unit 12.

Step S12

The operation signal output unit 12 transmits an operation signal corresponding to the operation input received by the operation input unit 11 to the information processing apparatus 2.

Step S13

The bioelectric potential amplifier 14 measures and amplifies a bioelectric potential corresponding to a potential difference between the plurality of electrodes 51 of the electrode unit 13. For example, the bioelectric potential amplifier 14 measures a potential difference between the measuring electrode 73$a$ disposed on a right side of the head (an electrode position of C4 according to the ten-twenty electrode system) and the reference electrode 73$b$ among the plurality of electrodes 51 of the electrode unit 13. Furthermore, the bioelectric potential amplifier 14 amplifies the measured bioelectric potential. A signal of the amplified bioelectric potential (bioelectric potential signal) is transmitted from the bioelectric potential amplifier 14 to the bioelectric potential output unit 15.

Step S14

Furthermore, the bioelectric potential output unit 15 transmits the transmitted bioelectric potential signal to the information processing apparatus 2.

In processing step S10 performed in the headset 1, Step S11 and Step S12 may be performed in parallel with Step S13 and Step S14. The processes in Step S11 through Step S14 need not necessarily be performed in the aforementioned order.

Next, processing step S20 performed in the information processing apparatus 2 is described.

Step S21

In the information processing apparatus 2, the operation signal acquisition unit 21 receives an operation signal from the operation signal output unit 12. The operation signal acquisition unit 21 transmits the received operation signal to the application processor 26.

Step S22

The bioelectric potential acquisition unit 22 receives a bioelectric potential signal from the bioelectric potential output unit 15. The bioelectric potential acquisition unit 22 transmits the received bioelectric potential signal to the bioelectric potential processor 23.

Step S23

Meaningful information is extracted from the bioelectric potential signal received by the bioelectric potential acquisition unit 22 by subjecting the bioelectric potential signal to analysis in the bioelectric potential processor 23. For example, a bioelectric potential signal of a predetermined frequency component is extracted. The predetermined frequency component is, for example, 10 Hz in a case where brain waves are to be measured.

Step S24

The application processor 26 receives the operation signal from the operation signal acquisition unit 21 and receives the bioelectric potential signal from the bioelectric potential processor 23, and performs predetermined processing for executing an application that is currently running. The predetermined processing is, for example, moving a game forward in a game application, recording, data management, and display in a health management application, and questioning, rating, and result display in an educational application, as described above.

Step S25

In order to feed a result of the processing of the application processor 26 back to the user 10, the display information output unit 27 supplies image information to the display unit 3, and the audio information output unit 28 supplies audio information to the display unit 3. In this way, an image and sound that correspond to the processing result are output from the display unit 3.

In processing Step S20 performed in the information processing apparatus 2, Step S22 and Step S23 may be performed in parallel with Step S24. The application processor 26 need not perform the processing by using both of the operation signal received from the operation signal acquisition unit 21 and the bioelectric potential signal received from the bioelectric potential processor 23. The application processor 26 may perform the processing by using the bioelectric potential signal. In this case, Step S21 of receiving the operation signal can be omitted.

Through the above processing flow, the information processing system 100 can obtain biological information such as brain waves from the user 10.

Compensation of contact impedance in a case where contact impedance of the electrode 51 of the headset 1 has changed, i.e., in a case where a position of the headset 1 attached to the user 10 has shifted is described. Details of a configuration of the bioelectric potential measuring device 1$b$ that is most related to compensation of contact impedance and a contact impedance compensation method are described below.

Active Electrode and Contact Impedance Compensator

Figure 10:
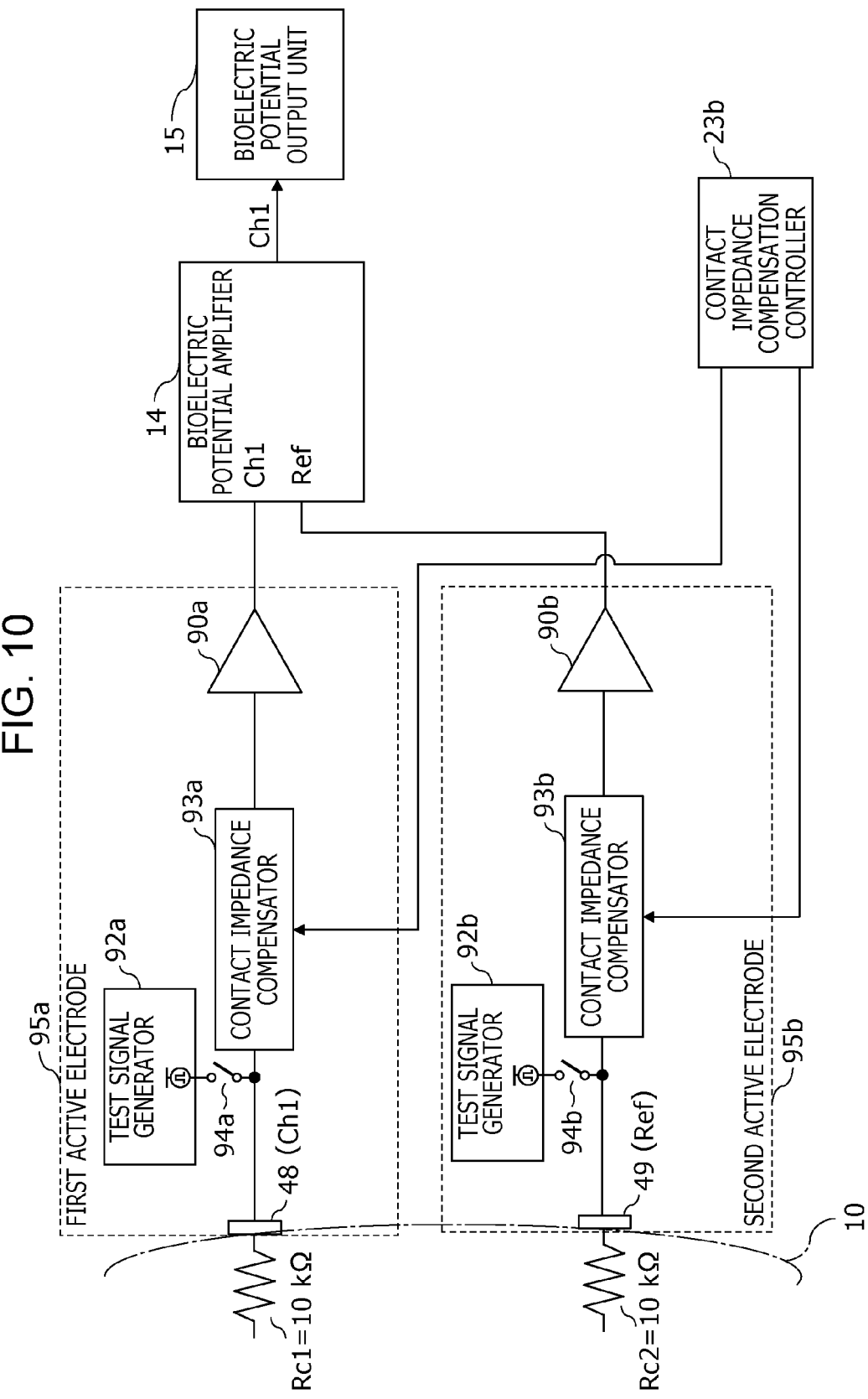
FIG. 10 is a block diagram illustrating a detailed configuration of a bioelectric potential measuring device according to Embodiment 1.

FIG. 10 is a block diagram illustrating a detailed configuration of the bioelectric potential measuring device 1b according to the present embodiment. FIG. 10 illustrates an example of electrical coupling in a case where the electrode unit 13 is disposed on the attachment surface 45 of the headset 1 of FIG. 2 and the headset 1 is attached to the head. In FIG. 10, an electrode used as a measuring electrode is referred to as an electrode 48, and an electrode used as a reference electrode is referred to as an electrode 49 among the plurality of electrodes 51 that constitute the electrode unit 13. In the following description, the electrode 48 may be referred to as Ch1, and the electrode 49 may be referred to as Ref.

The electrode unit 13 is disposed on a housing of the headset 1 and includes at least two electrodes, i.e., the electrode 48 (Ch1) and the electrode 49 (Ref). The electrode 48 is the measuring electrode 73a illustrated in FIG. 7 and corresponds to one channel (Ch1) among the plurality of electrodes 48.

The electrode 48 is at least one of the plurality of electrodes 51 provided on the attachment surface 45 illustrated in FIGS. 2A and 2B and makes contact with user's skin (an electrode position of C4 according to the ten-twenty electrode system). The skin with which the electrodes 48 are in contact is referred to as first skin. The electrode 49 is the electrode 51 provided at the end of the ear pad 46 on the right illustrated in FIG. 2A or at least one of the plurality of electrodes 51 provided on the attachment surface 45 illustrated in FIG. 2B and makes contact with skin behind the left ear of the user 10. The skin with which the electrodes 49 are in contact is referred to as second skin.

As illustrated in FIG. 10, a test signal generator 92a, a contact impedance compensator 93a, and a buffer 90a are coupled to the electrode 48. Similarly, a test signal generator 92b, a contact impedance compensator 93b, and a buffer 90b are coupled to the electrode 49. In general, a combination of an electrode and a buffer is referred to as an active electrode. In FIG. 10, a combination of the electrode 48 and the buffer 90a is referred to as a first active electrode 95a, and a combination of the electrode 49 and the buffer 90b is referred to as a second active electrode 95b. Use of an active electrode makes it possible to convert impedance of a signal source into a lower value (e.g., 1 kΩ) by output of a buffer even in a case where contact impedance of an electrode is high (30 kΩ at 10 Hz).

The buffer 90a corresponds to a first amplifier circuit according to the present disclosure. The buffer 90b corresponds to a second amplifier circuit according to the present disclosure. The test signal generator 92a corresponds to a first test circuit according to the present disclosure. The test signal generator 92b corresponds to a second test circuit according to the present disclosure. The contact impedance compensator 93a corresponds to a first compensation circuit according to the present disclosure. The contact impedance compensator 93b corresponds to a second compensation circuit according to the present disclosure.

The test signal generators 92a and 92b may share a single current source instead of a configuration in which each of the test signal generators 92a and 92b includes a current source. In this case, the single current source may be used by switching a switch coupled to a wire between the electrode 48 and the contact impedance compensator 93a and a switch coupled to a wire between the electrode 49 and the contact impedance compensator 93b.

The definition of a contact state of an electrode described with reference to FIG. 4 is applied to the bioelectric potential measuring device 1b of FIG. 10. As illustrated in FIG. 10, it can be considered that the electrodes 48 and 49 are in contact, from a positional relationship between the user 10 and the electrodes 48 and 49. Both of contact impedance Rc1 of the electrode 48 and contact impedance Rc2 of the electrode 49 are, for example, 10 kΩ.

Potentials detected by the electrodes 48 and 49 are sent to the bioelectric potential amplifier 14 through the contact impedance compensator 93a and 93b after buffering of a voltage in the buffers 90a and 90b, respectively, as illustrated in FIG. 10. Input impedance of the buffers 90a and 90b may be 500 MΩ or more at 10 Hz. Furthermore, gain and the input impedance of the buffer 90a may be equal to gain and the input impedance of the buffer 90b.

Each of the buffers 90a and 90b may be replaced with an operational amplifier circuit in which an absolute value of gain is 1 or more. In this case, amplification of a bioelectric potential in the bioelectric potential amplifier 14 is the second amplification next to amplification in the operational amplifier circuit. This mitigates requirements of input-referred noise as compared with a case where the buffers 90a and 90b are used, thereby allowing use of an amplifier that consumes less electric power.

The test signal generators 92a and 92b are alternating-current signal generators that are provided for the purpose of measuring contact impedance of the electrodes 48 and 49 in order to obtain information concerning contact states of the electrodes 48 and 49, respectively. For example, the test signal generators 92a and 92b output, as a test signal, a square-wave current having a frequency of 10 Hz and an amplitude of 10 nApp (peak-to-peak). The square-wave current flows to the human body (the user 10) side through the electrodes 48 and 49. The current that has flowed to the human body side returns to the headset 1 via an earth electrode (not illustrated). A voltage generated by measurement of contact impedance is expressed by a product of the square-wave current and the contact impedance.

A method for measuring contact impedance of the electrodes 48 and 49 is described below. The contact impedance of the electrode 48 is measured by a three-terminal method. More specifically, the three terminals are a potential (the electrode 48) of the + side input of the bioelectric potential amplifier 14 (the biological amplifier 74), a potential (the electrode 49) of the − side input of the bioelectric potential amplifier 14 (the biological amplifier 74), and the reference potential (the earth electrode). In principle, the contact impedance of the electrode 48 is obtained by measuring a difference between the potential (the electrode 48) of the + side input of the biological amplifier 74 and the potential (the electrode 49) of the − side input of the biological amplifier 74 while a square-wave current is being output, converting the measured voltage into an input voltage of the biological amplifier, and then dividing the input voltage by the square-wave current. More specifically, voltages of the electrodes 48 and 49 are buffered in the buffers 90a and 90b while a square-wave current is being output in the test signal generator 92a. Then, a difference value between the buffered voltages is amplified by predetermined gain in the biological amplifier 74. Furthermore, a difference between the amplified voltage and a reference voltage of output (signal ground: for example, when a power source voltage of the biological amplifier 74 is 1.8 V, the signal ground is 0.9 V, which is an intermediate voltage) is obtained, is divided by gain of the biological amplifier so as to be converted into an input voltage, and is then divided by a value of the square-wave current. In this way, the contact impedance Rc1 can be obtained. Note that the potential of the + side input and the potential of the − side input may be a reference potential of the earth electrode and a potential of the electrode 48, respectively.

Meanwhile, the contact impedance of the electrode 49 is measured by a two-terminal method. Specifically, in principle, the contact impedance of the electrode 49 is obtained by measuring an absolute value of a difference (voltage) between the potential (the potential of the electrode 49) of the + side input of the bioelectric potential amplifier 14 (the biological amplifier 74) and the potential (the reference potential of the earth electrode) of the − side input of the bioelectric potential amplifier 14 (the biological amplifier 74) while a square-wave current is being output and then dividing the measured voltage by the square-wave current. More specifically, the voltage of the electrode 49 is buffered in the buffer 90b while a square-wave current is being output in the test signal generator 92b. Next, a difference value between the buffered voltage and a voltage of the earth electrode (not illustrated) is amplified by predetermined gain in the biological amplifier 74. Then, the amplified voltage is converted into an input voltage of the biological amplifier and is then divided by a value of the square-wave current. In this way, the contact impedance Rc2 can be obtained. Note that the potential of the + side input and the potential of the − side input may be the reference potential of the earth electrode and the potential of the electrode 49, respectively.

Accuracy of contact impedance obtained by the above method is, for example, 1 kΩ or less.

Contact impedance values obtained by the test signal generators 92a and 92b are supplied to the bioelectric potential acquisition unit 22 of the information processing apparatus 2 through the bioelectric potential amplifier 14 and the bioelectric potential output unit 15 of the headset 1. Furthermore, the value of the contact impedance Rc2 is supplied from the bioelectric potential acquisition unit 22 to the bioelectric potential processor 23.

The test signal generator 92b may also function as the test signal generator 92a. In this case, the contact impedance Rc1 and Rc2 may be measured by switching coupling between the test signal generator 92b and the electrode 48 and coupling between the test signal generator 92b and the electrode 49 by using a switch (not illustrated).

The contact impedance compensators 93a and 93b give additional impedance (impedance compensation amount) to the wire between the electrode 48 and the buffer 90a and the wire between the electrode 49 and the buffer 90b, respectively. This will be described in detail later. Control signals for controlling opening or closing of switches SWa0 through SWa10 of the contact impedance compensator 93a and switches SWb0 through SWb10 of the contact impedance compensator 93b are generated by a contact impedance compensation controller 23b that will be described later. The switches SWa0 through SWa10 correspond to first short lines according to the present disclosure. The switches SWb0 through SWb10 correspond to second short lines according to the present disclosure.

The bioelectric potential amplifier 14 of FIG. 10 obtains a difference between a potential of the electrode 48 and a potential of the electrode 49 and then amplifies the potential difference (voltage) (differential amplification). The amplified voltage is filtered by a low-pass filter (not illustrated) and is then converted into a digital signal at a predetermined resolution (e.g., 12 bits) and a sampling frequency (e.g., 1 kHz) by an A/D converter (not illustrated). Data (digital data) thus converted into the digital signal is supplied to the bioelectric potential output unit 15. The digital data supplied to the bioelectric potential output unit 15 is digital data corresponding to contact impedance obtained at Ch1.

The electrode unit 13 and the bioelectric potential amplifier 14 illustrated in FIG. 10 may be coupled so that the buffers 90a and 90b are not provided on a path between the electrode 48 and the bioelectric potential amplifier 14 and on a path between the electrode 49 and the bioelectric potential amplifier 14, respectively. In this case, input impedance of the bioelectric potential amplifier 14 may be 500 MΩ (a value at a frequency of 10 Hz) or more.

Configuration of Contact Impedance Compensator

Figure 11:
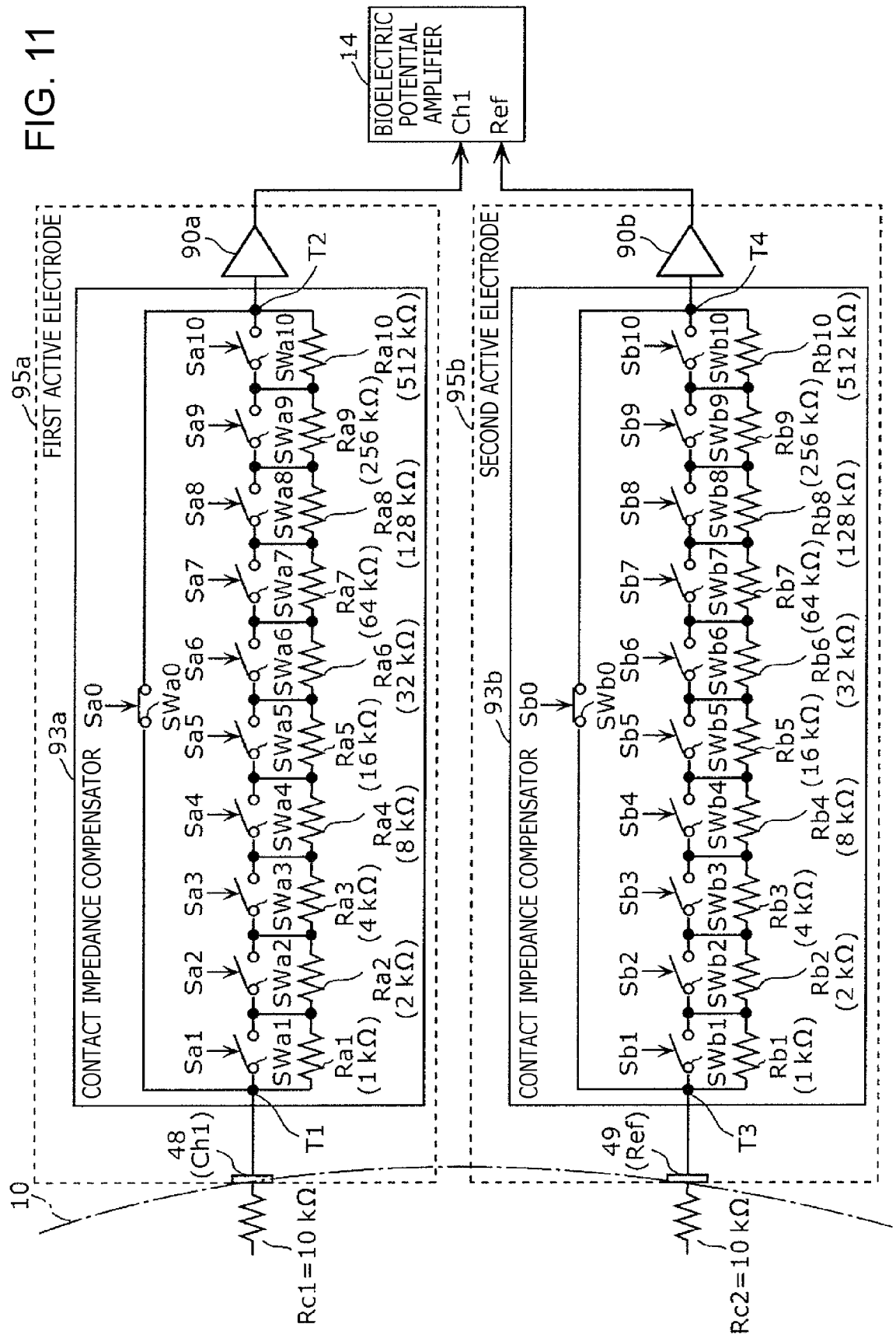
FIG. 11 is a circuit diagram illustrating a configuration of a contact impedance compensator according to Embodiment 1.

FIG. 11 is a circuit diagram illustrating an example of configurations of the contact impedance compensators 93a and 93b. The contact impedance compensator 93a that relays the electrode 48 and the buffer 90a and the contact impedance compensator 93b that relays the electrode 49 and the buffer 90b have resistance elements Ra1 to Ra10 and resistance elements Rb1 to Rb10 that are weighted by resistance values, respectively. Since the contact impedance compensators 93a and 93b have an identical configuration, the contact impedance compensator 93a is taken as an example in the following description.

As illustrated in FIG. 11, the resistance values of the resistance elements Ra1 to Ra10 are, for example, 1 kΩ, 2 kΩ, 4 kΩ, 8 kΩ, 16 kΩ, 32 kΩ, 64 kΩ, 128 kΩ, 256 kΩ, and 512 kΩ, respectively. Similarly, the resistance values of the resistance elements Rb1 to Rb10 are, for example, 1 kΩ, 2 kΩ, 4 kΩ, 8 kΩ, 16 kΩ, 32 kΩ, 64 kΩ, 128 kΩ, 256 kΩ, 512 kΩ, respectively. The resistance elements Ra1 to Ra10 correspond to first resistances according to the present disclosure. The resistance elements Rb1 to Rb10 correspond to second resistances according to the present disclosure.

As illustrated in FIG. 11, the contact impedance compensator 93a is configured such that the resistance elements Ra1 to Ra10 are serially coupled between a first terminal T1 and a second terminal T2 that are input and output terminals of the contact impedance compensator 93a, and thereby an impedance compensation amount is added. The first terminal T1 is coupled to the electrode 48, and the second terminal T2 is coupled to the buffer 90a. The resistance elements Ra1 to Ra10 have, at both ends thereof, switches SWa1 to SWa10 in parallel with the resistance elements Ra1 to Ra10 so as to be switchable, respectively. That is, resistance elements coupled in parallel with switches that are off among the switches SWa1 to SWa10 and switch (short lines) that are on among the switches SWa1 to SWa10 are coupled in series between the first terminal T1 and the second terminal T2. That is, an impedance compensation amount is a value obtained by adding resistance values of the resistance elements that are coupled in parallel with switches that are off among the switches SWa1 to SWa10. The value obtained by adding resistance values of the resistance elements that are coupled in parallel with switches that are off among the switches SWa1 to SWa10 correspond to a first resistance value and a seventh resistance value according to the present disclosure. The switches that are on among the switches SWa1 to SWa10 correspond to third short lines according to the present disclosure.

The contact impedance compensator 93a includes a switch SWa0 that is coupled between the first terminal T1 and the second terminal T2 in parallel with the resistance elements Ra1 to Ra10 and short-circuits a path from the electrode 48 to the buffer 90a.

The switches SWa0 to SWa10 are on (closed) when control signals Sa0 to Sa10 have an H (high) level and are off (opened) when the control signals Sa0 to Sa10 have an L (low) level. On resistance and off-leak current of the switches SWa0 to SWa10 may be 10Ω (a value in the case of DC) or less and 1 nA or less, respectively. The resistance elements Ra1 to Ra10 may have high accuracy (e.g., metal-coated chip resistances having accuracy of ±0.1%).

Immediately after activation of the headset or in a case where contact impedance is not compensated, the control signal Sa0 of the switch SWa0 is controlled to an H level (ON) so that the contact impedance compensator 93a is bypassed. In this case, a contact impedance compensation amount is 0 kΩ.

The contact impedance compensator 93b has a configuration similar to the configuration of the contact impedance compensator 93a. A value obtained by adding resistance values of the resistance elements that are coupled in parallel with switches that are off among the switches SWb1 to SWb10 correspond to a second resistance value and an eighth resistance value according to the present disclosure. Switches that are on among the switches SWb1 to SWb10 correspond to fourth short lines according to the present disclosure. A resistance value between the first terminal T1 and the second terminal T2 corresponds to a third resistance value and a fifth resistance value according to the present disclosure. A resistance value between the third terminal T3 and the fourth terminal T4 correspond to a fourth resistance value and a sixth resistance value according to the present disclosure. The control signals Sa0 to Sa10 correspond to first information according to the present disclosure. The control signals Sb0 to Sb10 correspond to second information according to the present disclosure.

In a case where contact impedance is compensated (described later), the contact impedance compensation controller 23b controls the switches SWa0 to SWa10 and the switches SWb0 to SWb10 in accordance with control signal Sa0 to Sa10 for the contact impedance compensator 93a and control signals Sb0 to Sb10 for the contact impedance compensator 93b so that desired impedance compensation amounts R1a and R2a are obtained, respectively. The control signals Sa0 to Sa10 for the contact impedance compensator 93a are first signals according to the present disclosure. The control signals Sb0 to Sb10 for the contact impedance compensator 93b are second signals according to the present disclosure.

The resistance elements Ra1 to Ra10 of the contact impedance compensator 93a may have a resistance value ladder-type (R-2R ladder-type) configuration instead of the configuration in which the resistance elements Ra1 to Ra10 are weighted by 1 kΩ, 2 kΩ, 4 kΩ, 8 kΩ, 16 kΩ, 32 kΩ, 64 kΩ, 128 kΩ, 256 kΩ, and 512 kΩ, respectively. The same applies to the resistance elements Rb1 to Rb10 of the contact impedance compensator 93b. In a case where the contact impedance compensators 93a and 93b are provided by a semiconductor process, a mounting area can be reduced.

In a case where weights of the resistance elements Ra1 to Ra10 and resistance elements Rb1 to Rb10 are to be changed, at least one of the resistance elements Ra1 to Ra10 and the resistance elements Rb1 to Rb10 may be an analog-control-type potentiometer (semi-fixed resistor).

Figure 12:
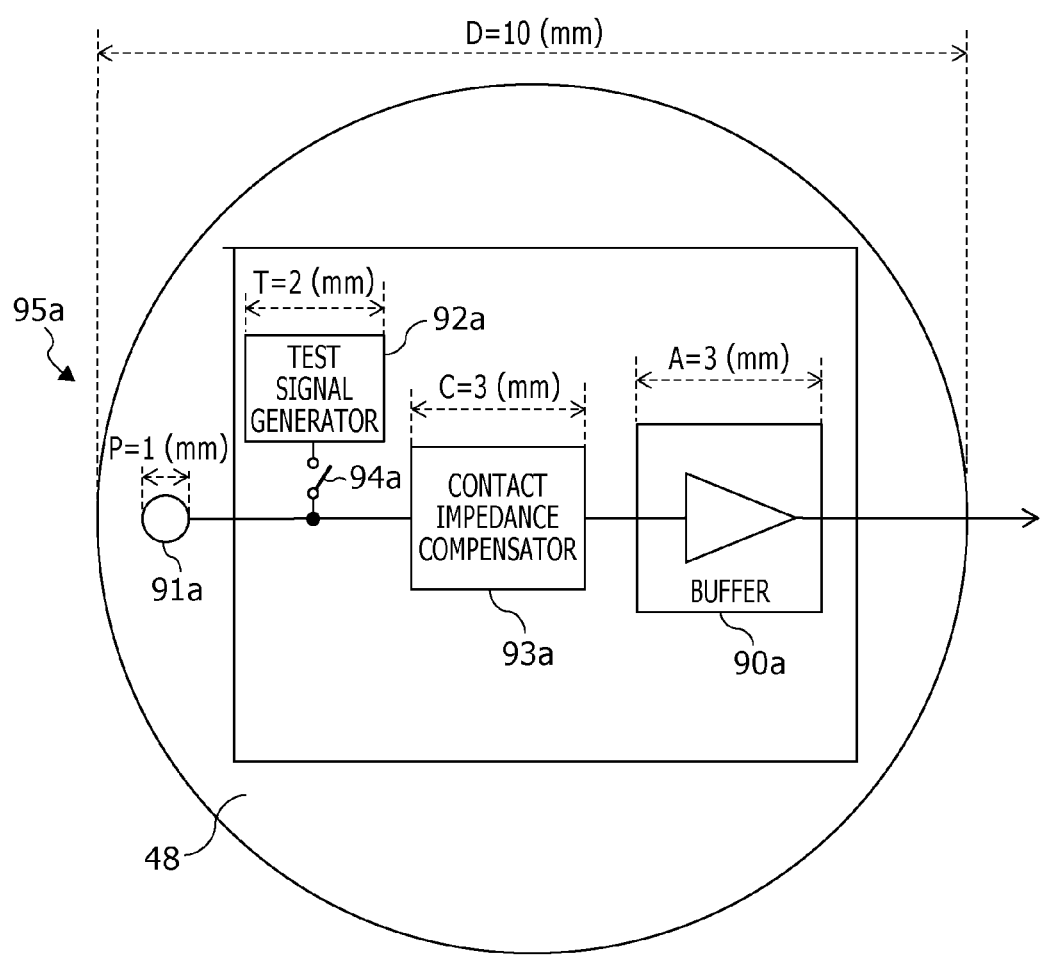
FIG. 12 illustrates a positional relationship in an active electrode according to Embodiment 1.

In a case where digital-control-type potentiometers are used as the contact impedance compensators 93a and 93b, the control signals may be controlled by using a digital control interface (e.g., 120 that is a two-wire type or SPI that is a three-wire/four-wire type). A resistance value per digital code 1 LSB (minimum bit) in the digital-control-type potentiostat may be 100Ω (0.1 kΩ) or less. Positional Relationship among Electrode, Contact Impedance Compensator, and Amplifier Next, a positional relationship among the electrode 48, the contact impedance compensator 93a, and the buffer 90a that are disposed in the first active electrode 95a of FIG. 12 is described. Since the second active electrode 95b is similar to the first active electrode 95a, detailed description of the second active electrode 95b is omitted.

In FIG. 12, it is assumed that a contact surface of the electrode 48 with skin (first skin) of the user 10 is circular. A diameter of the electrode 48 in plan view of the electrode 48 viewed from the contact surface side is defined as D (mm). In a case where the electrode 48 has the shape illustrated in FIGS. 3D and 3E, the dimension of the electrode 48 is defined by the diameter D (mm) of a circumscribed circle by surrounding the electrode 48 in plan view of the electrode 48 viewed from the contact surface side by the circumscribed circle having the diameter D (mm).

The relationship expressed by the following formula (1) may be satisfied:

$$D \geq T + C + A \qquad \text{formula (1)}$$

where D (mm) is the diameter of the electrode 48, P (mm) is a diameter of a soldering coupling part 91a provided between the electrode 48 and a lead wire in order to couple the electrode 48 to the lead wire, C (mm) is a length in a longitudinal direction of the contact impedance compensator 93a, and A (mm) is a length in a longitudinal direction of the buffer 90a.

For example, in a case where the diameter D of the electrode 48 is 10 mm, the relationship expressed by the following formula (1) is satisfied by designing P, T, C, and A to 1 mm, 2 mm, 3 mm, and 3 mm, respectively. In this case, the first active electrode 95a falls within the range of the diameter D=10 mm of the electrode 48, and influence of hum noise is limited to the contact surface between the electrode 48 and skin. That is, even in a case where the contact impedance compensator 93a is disposed in the electrode 48, contact impedance can be compensated without influence of extra hum noise.

The size of the electrode 48 may be determined on the basis of an actual contact range with skin so as to be similar to the shape of the electrode 48 illustrated in FIG. 12.

The test signal generator 92a, the contact impedance compensator 93a, and the buffer 90a may be integrated onto a semiconductor integrated circuit. By integrating the test signal generator 92a, the contact impedance compensator 93a, and the buffer 90a onto a semiconductor integrated circuit, a mounting area can be reduced. This makes it possible to acquire a bioelectric potential with high signal quality since there is no influence of extra hum noise.

In a case where the buffer 90a is not provided in FIG. 12, the relationship expressed by the following formula (2) may be satisfied:

$$D \geq P + T + C \qquad \text{formula (2)}$$

where D (mm) is the diameter of the electrode 48, P (mm) is a diameter of the soldering coupling part 91a, and C (mm) is a length in a longitudinal direction of the contact impedance compensator 93a.

For example, in a case where the diameter D of the electrode 48 is 10 mm, P, T, and C need just be designed to 1 mm, 2 mm, and 3 mm, respectively. This makes it possible to compensate contact impedance without influence of extra hum noise even in a case where the contact impedance compensator 93a is disposed in the electrode 48.

The aforementioned positional relationship among the electrode 48, the test signal generator 92a, the contact impedance compensator 93a, and the buffer 90a also applies to the positional relationship among the electrode 49, the test signal generator 92b, the contact impedance compensator 93b, and the buffer 90b in the second active electrode 95b.

Connection from Electrode Unit to Bioelectric Potential Amplifier

Connection from the electrode unit 13 of the headset 1 to the bioelectric potential amplifier 14 is described with reference to FIG. 10. Output terminals of the first active electrode 95a and the second active electrode 95b are coupled to a terminal for Ch1 and a terminal for Ref of the bioelectric potential amplifier 14, respectively. In the bioelectric potential amplifier 14, a difference of a signal of Ch1 from a signal of Ref is obtained and is then amplified (differential amplification). The amplified signal is filtered by a low-pass filter (not illustrated) and is then converted into a digital signal by an A/D converter (not illustrated). Data of the digital signal (digital data) thus converted is supplied to the bioelectric potential output unit 15.

Bioelectric Potential Processor

Figure 13:
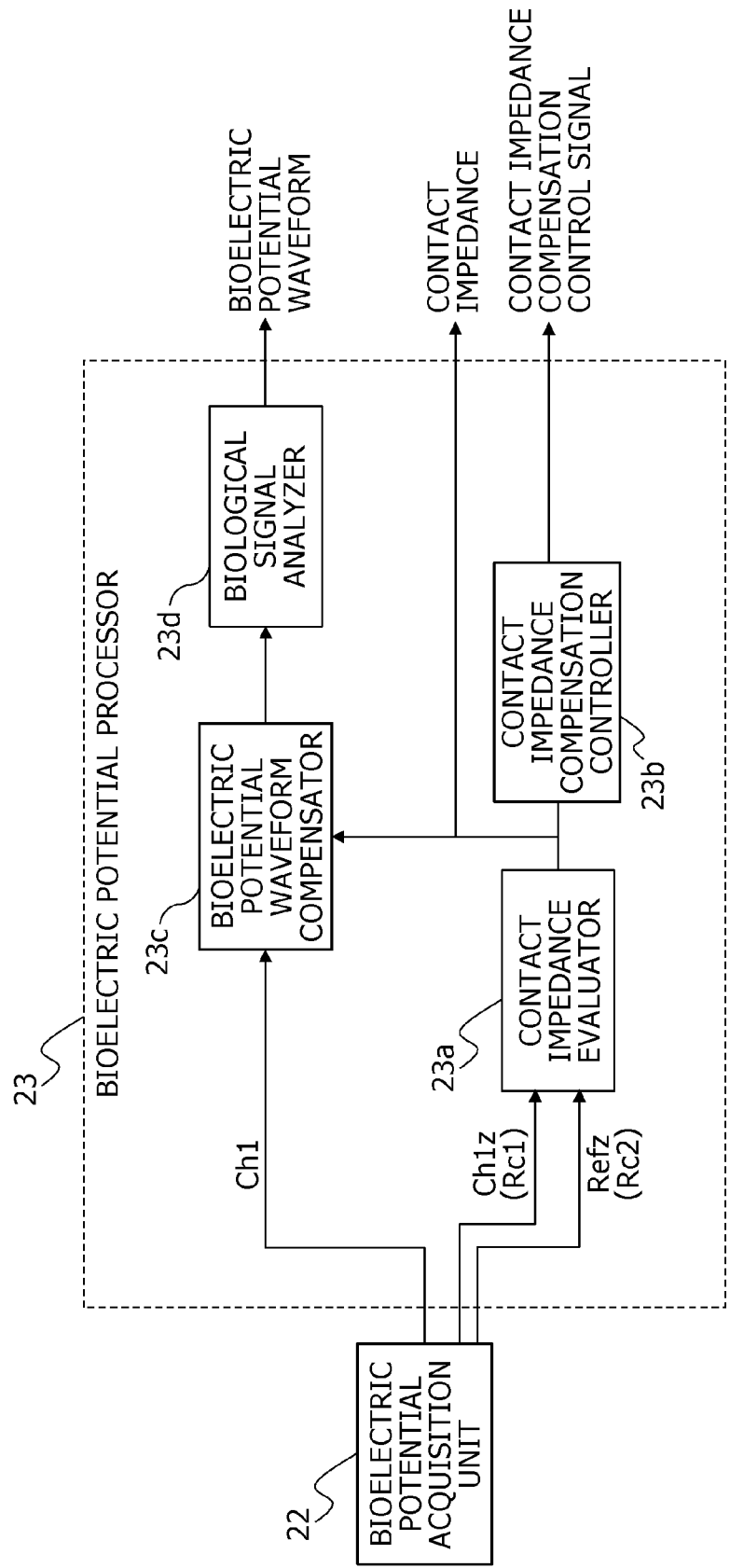
FIG. 13 illustrates a configuration of a bioelectric potential processor according to Embodiment 1.

FIG. 13 illustrates a configuration of the bioelectric potential processor 23. The bioelectric potential processor 23 includes a contact impedance evaluator 23a, a contact impedance compensation controller 23b, a bioelectric potential waveform compensator 23c, and a biological signal analyzer 23d.

In the information processing apparatus 2, the bioelectric potential processor 23 need just include at least the contact impedance evaluator 23a, the contact impedance compensation controller 23b, and the bioelectric potential waveform compensator 23c.

The contact impedance evaluator 23a analyzes contact states of the electrode 48 and the electrode 49 on the basis of values of contact impedance Ch1z and Refz of the electrode 48 and the electrode 49 acquired by the bioelectric potential acquisition unit 22. The contact impedance evaluator 23a determines whether or not the electrode 48 and the electrode 49 are in contact with skin of the user 10. Specifically, the contact impedance evaluator 23a determines whether or not the contact impedance of the electrode 48 and the electrode 49 is equal to or lower than a predetermined value on the basis of an output result of the bioelectric potential acquisition unit 22. The predetermined value is 5 MΩ, for example, in a case where a frequency of a test signal output from the test signal generators 92a and 92b is 10 Hz (500 kΩ in a case where the frequency of the test signal is 1 kHz). The contact impedance evaluator 23a determines that the electrode 48 or the electrode 49 is in contact with skin of the user 10 in a case where the contact impedance value of the electrode 48 or the electrode 49 is equal to or lower than the predetermined value (for example, even in a case where the contact impedance value is 30 kΩ or more at 10 Hz). In a case where the contact impedance value is larger than the predetermined value, the contact impedance evaluator 23a determines that the electrode is completely separate from the skin of the user 10.

The contact impedance evaluator 23a transmits, to the application processor 26, a result of the determination as to whether or not the electrode 48 and the electrode 49 are in contact with skin of the user 10. The application processor 26 notifies the user 10 about the contact states of the electrode 48 and the electrode 49 through the display information output unit 27 and the audio information output unit 28 on the basis of the result of the determination in the contact impedance evaluator 23a.

In a case where it is determined that the electrode 48 and the electrode 49 are in contact with skin of the user 10, the contact impedance evaluator 23a adopts, as contact impedance values of the electrode 48 and the electrode 49, values of contact impedance Rc1 and Rc2 acquired by the bioelectric potential acquisition unit 22. Furthermore, the contact impedance evaluator 23a determines which of the contact impedance values of the electrode 48 and the electrode 49 is higher and evaluates a difference between the contact impedance Rc1 of the electrode 48 and the contact impedance Rc2 of the electrode 49.

The contact impedance compensation controller 23b determines impedance compensation amounts of the electrode 48 and the electrode 49 on the basis of the relationship between the contact impedance Rc1 and the contact impedance Rc2 and the difference between the contact impedance Rc1 and the contact impedance Rc2 that are determined and evaluated by the contact impedance evaluator 23a and generates control signals Sa0 to Sa10 and control signals Sb1 to Sb10 for contact impedance compensation to be supplied to the contact impedance compensators 93a and 93b so that the impedance compensation amounts become predetermined values. Furthermore, the contact impedance compensation controller 23b transmits the generated control signals Sa0 to Sa10 and control signals Sb1 to Sb10 to the contact impedance compensators 93a and 93b, respectively. In this way, in the contact impedance compensators 93a and 93b, the switches SWa0 to SWa10 and the switches SWb1 to SWb10 are controlled by the control signals Sa0 to Sa10 and the control signals Sb1 to Sb10, respectively, and thereby impedance is compensated. The contact impedance compensation controller 23b may also transmit the generated control signals Sa0 to Sa10 and control signals Sb1 to Sb10 to the application processor 26. The application processor 26 may perform application processing on the basis of the transmitted control signals Sa0 to Sa10 and control signals Sb1 to Sb10.

The contact impedance evaluator 23a and the contact impedance compensation controller 23b correspond to a controller according to the present disclosure.

The bioelectric potential waveform compensator 23c determines an amplitude compensation coefficient Ca for a bioelectric potential on the basis of a bioelectric potential waveform of Ch1 acquired from the bioelectric potential acquisition unit 22 and a difference in amplitude between the contact impedance Rc1 and Rc2 evaluated by the contact impedance evaluator 23b and compensates an amplitude of the bioelectric potential waveform of Ch1 obtained by the electrode 48. The bioelectric potential waveform compensator 23c corresponds to a third compensation circuit according to the present disclosure.

The biological signal analyzer 23d includes, for example, a high-pass filter and a low-pass filter having a cutoff frequency that can be set. The biological signal analyzer 23d may include a notch filter that blocks a frequency (50 Hz or 60 Hz) of hum noise. The biological signal analyzer 23d performs signal processing by using these filters and the like and generates a bioelectric potential waveform to be displayed on the display unit 3 by the display information output unit 27.

Common Mode Rejection Ratio Taking Contact Impedance into Consideration

Next, a common mode rejection ratio (CMRR) of a bioelectric potential measurement system taking contact impedance into consideration is described. The common mode rejection ratio is also called a discrimination factor and represents an ability of removing a signal (common-mode signal) that is common to two inputs of a differential amplifier or the like. The common mode rejection ratio is a ratio of gain of a differential signal to gain of a common-mode signal. In the present embodiment, the common mode rejection ratio is used to determine a compensation coefficient that is used for compensation of an amplitude of a bioelectric potential in the bioelectric potential waveform compensator 23c.

Figure 14:
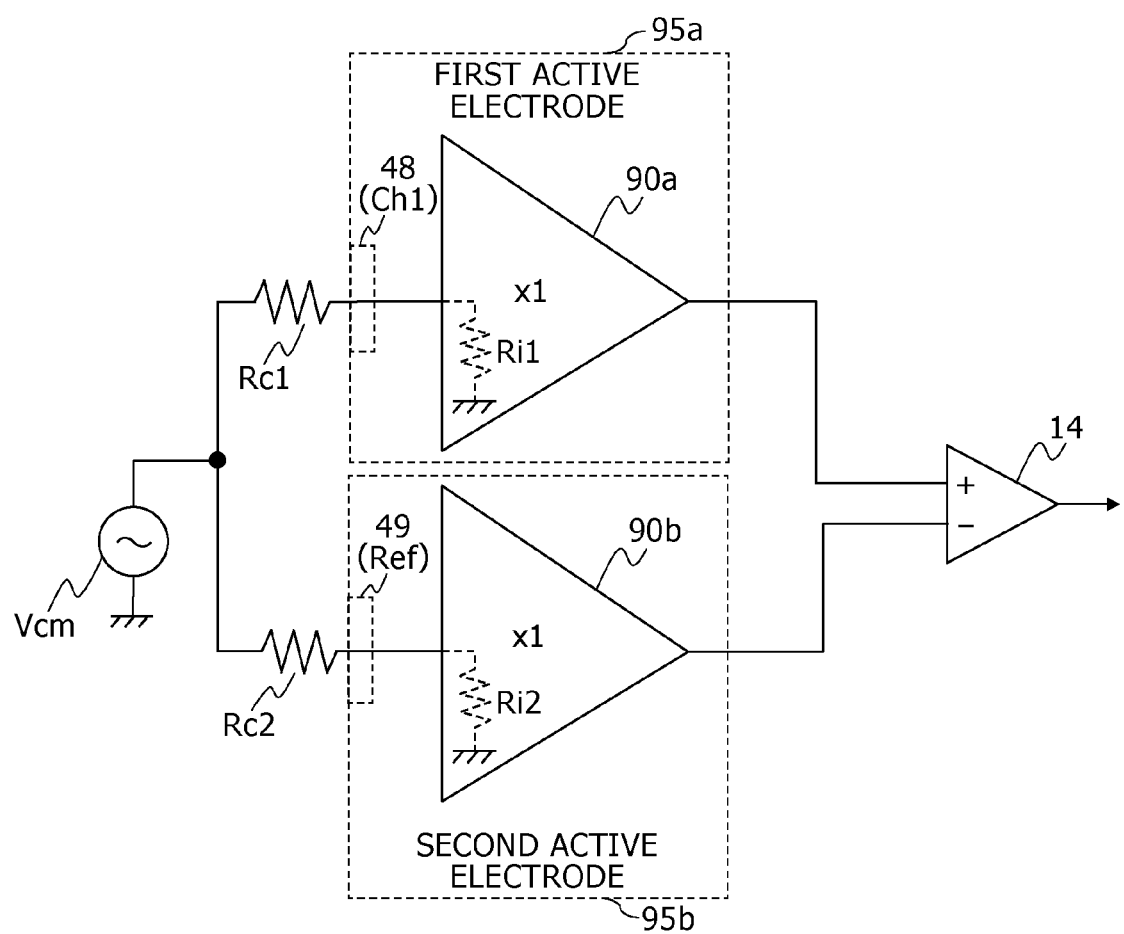
FIG. 14 is a circuit diagram illustrating a model for calculating a common mode rejection ratio of a bioelectric potential measurement system according to Embodiment 1.
Figure 15:
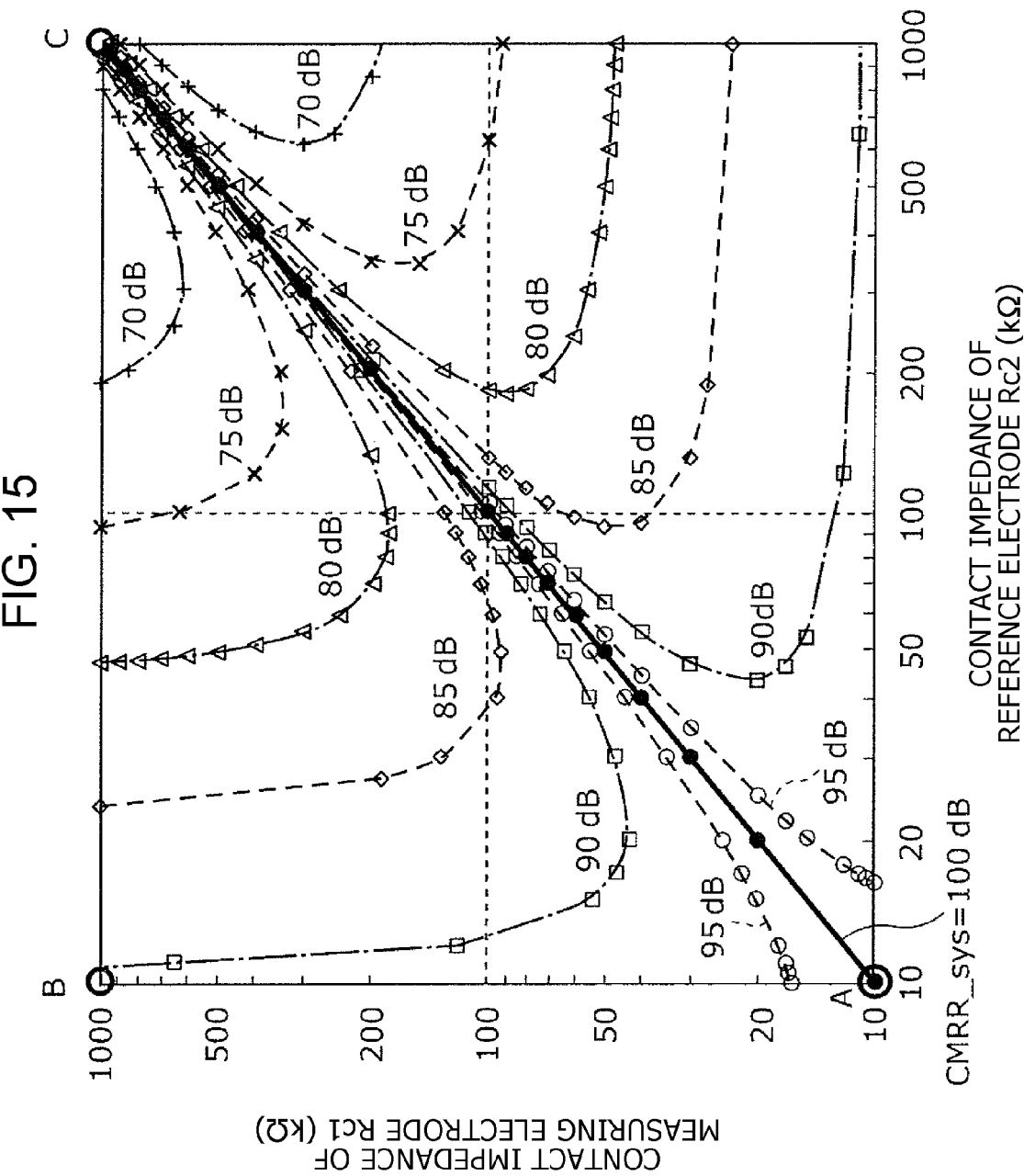
FIG. 15 illustrates common mode rejection ratio characteristics of the bioelectric potential measurement system according to Embodiment 1.

FIG. 14 is a circuit diagram illustrating a model of calculation of a common mode rejection ratio of a bioelectric potential measurement system. The electrode 48 and the electrode 49 constitute the first active electrode 95a and the second active electrode 95b having the buffer 90a and the buffer 90b, respectively, and a potential of Ch1 obtained by the electrode 48 and a reference potential obtained by the electrode 49 are subjected to differential amplification in the bioelectric potential amplifier 14. The contact impedance of the electrode 48 and the contact impedance of the electrode 49 are referred to as Rc1 and Rc2, respectively. The input impedance of the buffer 90a and the input impedance of the buffer 90b are referred to as Ri1, and Ri2, respectively. A common mode rejection ratio CMRR_sys of the bioelectric potential measurement system illustrated in FIG. 15 is approximately given by the following formula (3):

$$\text{CMRR\_sys} \approx \frac{\left(\frac{1}{2}\right)\left(\frac{Rc1 \cdot Ri2}{Rc2 \cdot Ri1} + \frac{2 \cdot Ri2}{Rc2} + 1\right)}{\left(\frac{1}{2}\right)\left(\frac{1}{\text{CMRR\_amp}}\right)\left(\frac{Rc1 \cdot Ri2}{Rc2 \cdot Ri1} + \frac{2 \cdot Ri2}{Rc2} + 1\right) + \left(1 - \frac{Rc1 \cdot Ri2}{Rc2 \cdot Ri1}\right)} \quad \text{formula (3)}$$

where CMRR_amp is a common mode rejection ratio of the bioelectric potential amplifier 14.

In general, the input impedance of the buffer 90a and the input impedance of the buffer 90b are equal to each other since the buffer 90a and the buffer 90b are identical to each other. Therefore, the relationship expressed by the following formula (4) is obtained:

$$Ri1 = Ri2 \quad \text{formula (4)}$$

In a case where the contact impedance Rc1 of the electrode 48 and the contact impedance Rc2 of the electrode 49 are equal to each other, the relationship expressed by the following formula (5) is obtained:

$$Rc1 = Rc2 \quad \text{formula (5)}$$

When the formula (4) and the formula (5) are substituted into the formula (3), the common mode rejection ratio CMRR_sys of the biological signal measurement system in a case where the contact impedance Rc1 of the electrode 48 and the contact impedance Rc2 of the electrode 49 are equal to each other is expressed by the following formula (6):

$$\text{CMRR\_sys} \approx \text{CMRR\_amp} \quad \text{formula (6)}$$

The formula (6) shows that the ability of removing a common-mode signal (e.g., hum noise) in the bioelectric potential amplifier 14 can be exercised and thus a bioelectric potential of high quality can be acquired by equalizing the contact impedance Rc1 and Rc2 so that the compensated contact impedance of the electrode 49 and the compensated contact impedance of the electrode 48 are always equal to each other.

FIG. 15 is a diagram plotting, on the basis of the formula (3), common mode rejection ratios CMRR_sys of the bioelectric potential measurement system obtained by changing the contact impedance Rc1 of the electrode 48 and the contact impedance Rc2 of the electrode 49. In this example, the input impedance of the buffer 90a and the buffer 90b is Ri1=Ri2=500 MΩ, and the common mode rejection ratio of the bioelectric potential amplifier 14 is CMRR_amp=100 dB. For example, at the point A (first state) of FIG. 15, the contact impedance Rc1 of the electrode 48 and the contact impedance Rc2 of the electrode 49 are equal to each other, specifically, 10 kΩ. In this case, the common mode rejection ratio CMRR_sys of the bioelectric potential measurement system is 100 dB, which is equal to the common mode rejection ratio CMRR_amp of the bioelectric potential amplifier 14 when the formula (6) is referred to. Next, the point changes to the point B (second state) of FIG. 15. In this case, the contact impedance Rc1 of the electrode 48 deteriorates to 1000 kΩ, the contact impedance Rc2 of the electrode 49 keeps 10 kΩ, and the common mode rejection ratio CMRR_sys of the bioelectric potential measurement system deteriorates to 91 dB when calculated on the basis of the formula (3). Accordingly, in the second state, the ability of removing hum noise of the bioelectric potential measurement system deteriorates.

In the present embodiment, the contact impedance is compensated so that the point changes from the point B (second state) to the point C (third state) of FIG. 15. An impedance compensation amount added to the electrode 48 by the contact impedance compensator 93a is referred to as Ra1, and an impedance compensation amount added to the electrode 49 by the contact impedance compensator 93b is referred to as Ra2. The impedance compensation amount Ra1 corresponds to a first compensation value according to the present disclosure, and the impedance compensation amount Ra2 corresponds to a second compensation value according to the present disclosure. Synthetic impedance obtained after impedance compensation is defined as a sum of contact impedance and an impedance compensation amount. The following formulas (7) and (8) are established:

$$Rt1 = Rc1 + Ra1 \quad \text{formula (7)}$$

$$Rt2 = Rc2 + Ra2 \quad \text{formula (8)}$$

where Rt1 and Rt2 are synthetic impedance of the electrode 48 and synthetic impedance of the electrode 49, respectively.

In the present embodiment, contact impedance compensation is to make the synthetic impedance Rt1 and the synthetic impedance Rt2 equal to each other. This means that the impedance compensation amounts Ra1 and Ra2 are determined so that the following formula (9) is established:

$$Rt1 = Rt2 \quad \text{formula (9)}$$

For example, in a case where contact impedance is compensated so that the point changes from the point B (second state) to the point C (third state) in FIG. 15, the synthetic impedance Rt1 and Rt2 are set to 1000 kΩ so that the formula (7) is established since Rc1=1000 kΩ and Rc2=10 kΩ. That is, the contact impedance of the electrode 48 is not compensated, and therefore Ra1=0 kΩ. Meanwhile, the contact impedance of the electrode 49 is compensated, and the impedance compensation amount Ra2 is set to 990 kΩ.

The common mode rejection ratio CMRR_sys of the bioelectric potential measurement system taking the above contact impedance compensation into consideration is described. The following formula (10) is obtained by assigning the synthetic impedance Rt1 to the contact impedance Rc1 and assigning the synthetic impedance Rt2 to the contact impedance Rc2 in the formula (3):

$$\text{CMRR\_sys} \approx \frac{\left(\frac{1}{2}\right)\left(\frac{Rt1 \cdot Ri2}{Rt2 \cdot Ri1} + \frac{2 \cdot Ri2}{Rt2} + 1\right)}{\left(\frac{1}{2}\right)\left(\frac{1}{\text{CMRR\_amp}}\right)\left(\frac{Rt1 \cdot Ri2}{Rt2 \cdot Ri1} + \frac{2 \cdot Ri2}{Rt2} + 1\right) + \left(1 - \frac{Rt1 \cdot Ri2}{Rt2 \cdot Ri1}\right)} \quad \text{formula (10)}$$

The formula (9) is established after contact impedance compensation. The following formula (11) is established when the formula (9) is substituted into the formula (10):

CMRR_sys≈CMRR_amp formula (11)

The formula (11) shows that at the point C (third state) of FIG. 15, the common mode rejection ratio CMRR_sys of the bioelectric potential measurement system is 100 dB, which is equal to the common mode rejection ratio CMRR_amp of the bioelectric potential amplifier 14. The contact impedance compensation of the present embodiment makes it possible to prevent a deterioration of the ability of common mode rejection caused by hum noise, thereby making it possible to acquire a bioelectric potential of high quality.

Compensation of Contact Impedance

Figure 19:
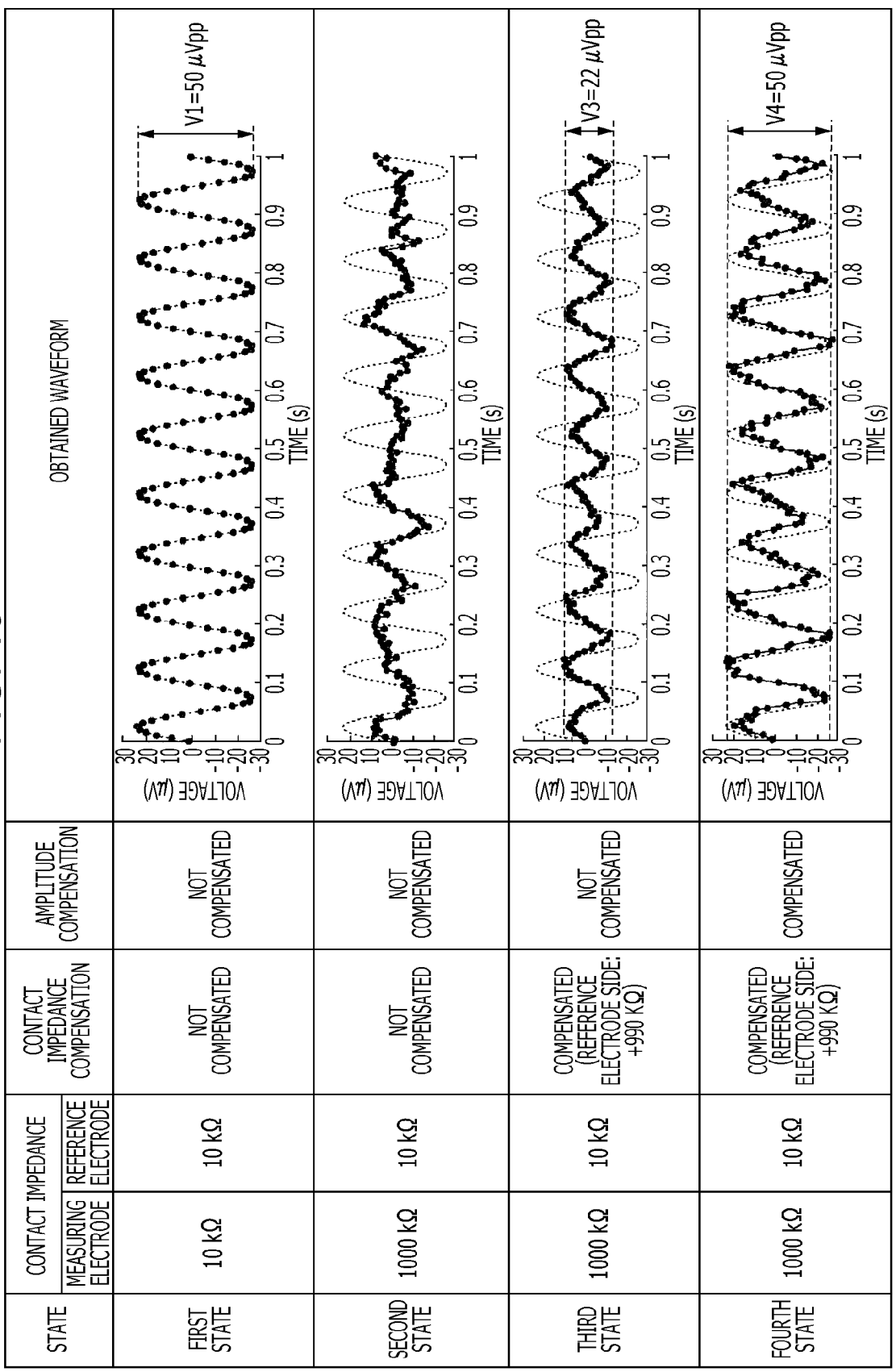
FIG. 19 illustrates an example of contact impedance compensation and amplitude compensation according to Embodiment 1.

An example of an operation of the contact impedance compensators 93a and 93b is described with reference to FIGS. 11, 16, 17, an operation table (FIG. 18), and obtained bioelectric potential waveforms (FIG. 19). Operations of the contact impedance compensators 93a and 93b in the first state (A), the second state (B), and the third state (C) of FIG. 15 correspond to FIGS. 11, 16, and 17, respectively. The voltage waveforms illustrated in FIG. 19 are bioelectric potential waveforms obtained in the first through third states and a fourth state (described later), i.e., waveforms of bioelectric potentials output from the contact impedance compensators 93a and 93b in the first through third states and the fourth state (described later). In the present embodiment, an obtained waveform is a waveform of an amplitude converted into an input waveform of the electrode 48 that is the measuring electrode (Ch1) and the electrode 49 that is the reference electrode (Ref). In any of the first through fourth states, the input waveform is a sinusoidal wave having 10 Hz and 50 μVpp that simulates a bioelectric potential waveform.

Initially, the switches SWa0 to SWa10 of the contact impedance compensator 93a and the switches SWb0 to SWb10 of the contact impedance compensator 93b are in the first state illustrated in FIG. 11. In the first state, the contact impedance Rc1 of the electrode 48 and the contact impedance Rc2 of the electrode 49 are equal, specifically, Rc1=Rc2=10 kΩ. The control signals Sa0 to Sa10 for the contact impedance compensator 93a and the control signals Sb0 to Sb10 for the contact impedance compensator 93b are set so that the control signals Sa0 and Sb0 are H and the control signal Sa1 to Sa10 and Sb1 to Sb10 are L, as illustrated in FIG. 18. That is, in the contact impedance compensators 93a and 93b, the switches SWa0 and SWb0 are closed. Therefore, impedance compensation is not performed, and the impedance compensation amounts Ra1 and Ra2 are Ra1=Ra2=0 kΩ. The synthetic impedance Rt1 of the electrode 48 and the synthetic impedance Rt2 of the electrode 49 are Rt1=Rt2=10 kΩ when the formulas (7) and (8) are referred to. As illustrated in FIG. 19, a waveform obtained in the first state of the contact impedance compensators 93a and 93b is a sinusoidal waveform having a frequency of 10 Hz and an amplitude of V1=50 μVpp and overlaps an input waveform indicated by the dotted line in FIG. 19.

Figure 16:
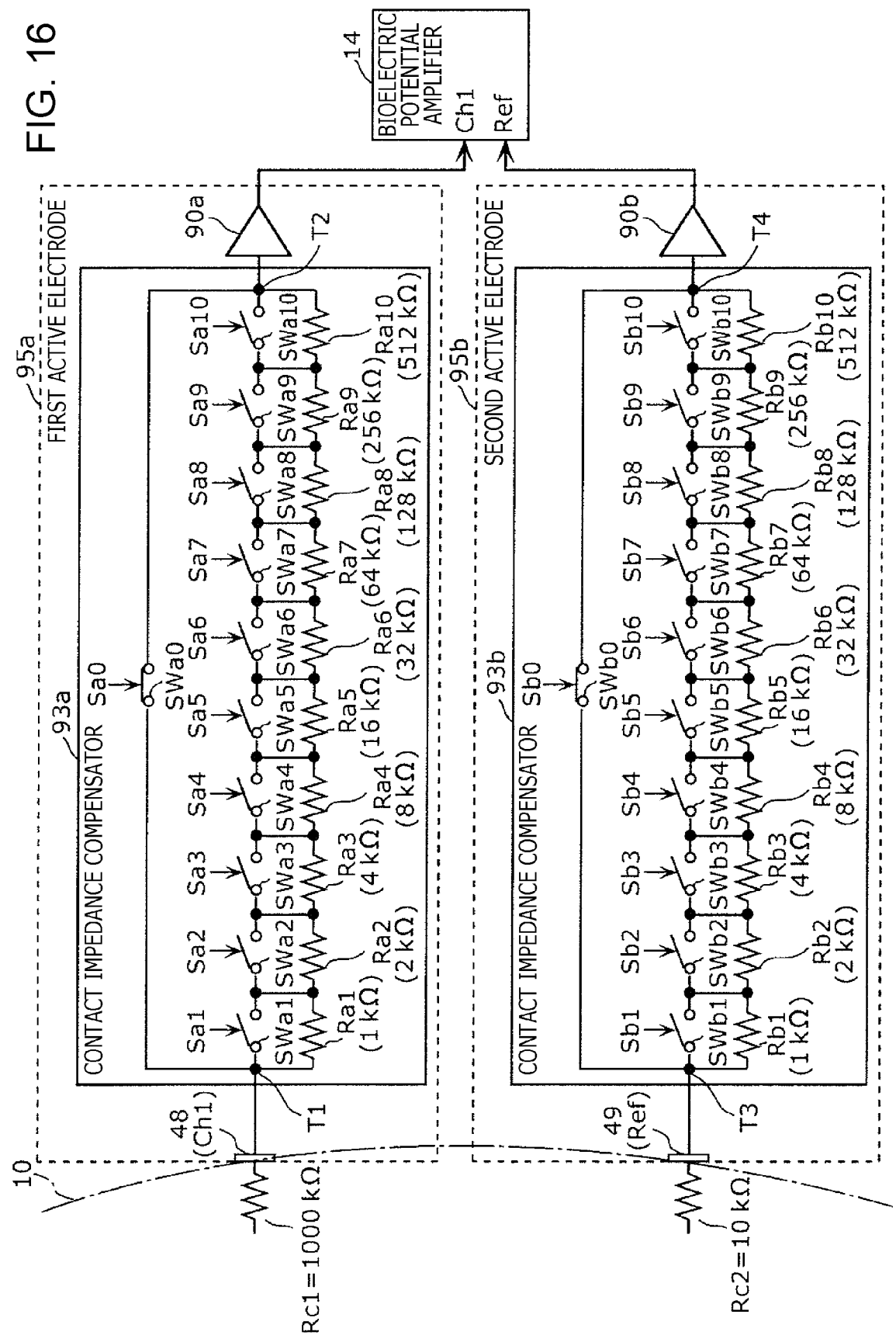
FIG. 16 illustrates an example of an operation of the contact impedance compensator according to Embodiment 1.
Figure 17:
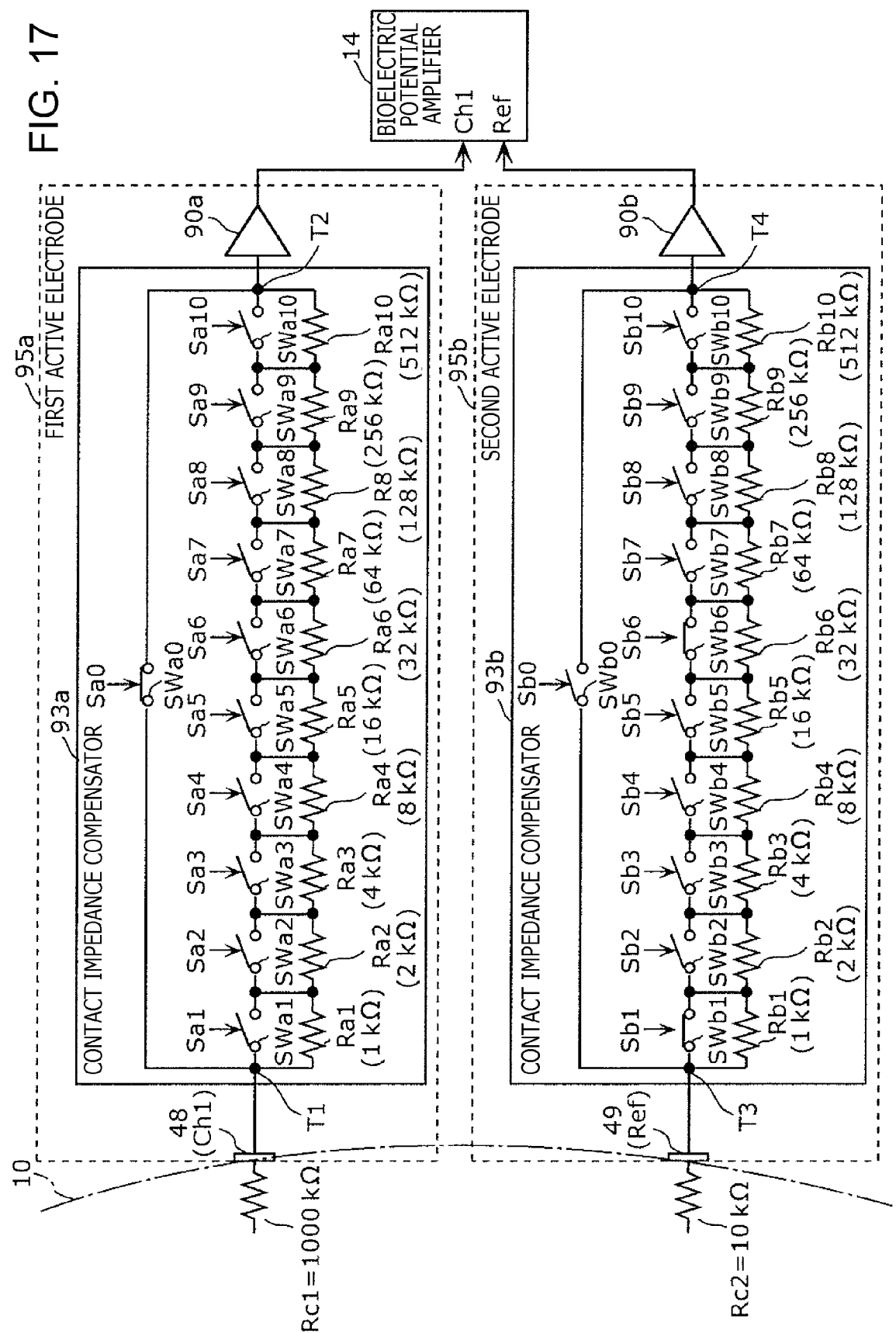
FIG. 17 illustrates an example of an operation of the contact impedance compensator according to Embodiment 1.

As illustrated in FIG. 16, when the state changes from the first state to the second state, for example, because of a body motion of a user, the contact impedance Rc1 of the electrode 48 deteriorates to 1 MΩ (1000 kΩ). In the operation table of FIG. 18, the control signals Sa0 to Sa10 for the contact impedance compensator 93a and the control signals Sb0 to Sb10 for the contact impedance compensator 93b are the same as those in the first state since contact impedance compensation is not performed, and the impedance compensation amounts Ra1 and Ra2 are Ra1=Ra2=0 kΩ. The synthetic impedance Rt1 of the electrode 48 and the synthetic impedance Rt2 of the electrode 49 in this state are not equal to each other, specifically, Rt1=1000 kΩ and Rt2=10 kΩ. Therefore, an obtained waveform deteriorates due to influence of hum noise.

FIG. 19 illustrates a waveform in the second state. When the waveform is superimposed on the sinusoidal wave (plotted in the dotted line) of the input waveform having 10 Hz and 50 μVpp, a most part of the sinusoidal waveform has a crushed shape (the amplitude V2 is not constant). This shows that signal quality of the bioelectric potential has been remarkably impaired.

The third state is a state where the contact impedance compensation according to the present embodiment is performed. FIG. 17 is a circuit diagram of the contact impedance compensators 93a and 93b in the third state. As illustrated in the third state of the operation table illustrated in FIG. 18, the impedance compensation amount Ra1 of the electrode 48 is adjusted to 0 kΩ and the impedance compensation amount Ra2 of the electrode 49 is adjusted to 990 kΩ, and the control signals Sa0 to Sa10 for the contact impedance compensator 93a and the control signals Sb0 to Sb10 for the contact impedance compensator 93b are set. Both of the synthetic impedance Rt1 of the electrode 48 and the synthetic impedance Rt2 of the electrode 49 are equalized to 1000 kΩ. An output waveform in this state is illustrated in FIG. 19.

As illustrated in FIG. 19, in the third state, a waveform close to a sinusoidal wave having a frequency 10 Hz is observed as an obtained waveform. An amplitude V3 of the obtained waveform is 22 μVpp, which is lower by 28 μVpp than an amplitude Vdiff (=50 μVpp) of the input waveform.

Compensation of Amplitude of Bioelectric Potential Waveform

In the present embodiment, the amplitude of the bioelectric potential waveform that has attenuated in the third state is further compensated. A state where the amplitude of the bioelectric potential waveform has been compensated is the fourth state. The amplitude of the bioelectric potential waveform is compensated by the bioelectric potential waveform compensator 23c illustrated in FIG. 13.

As illustrated in FIG. 18, setting of the control signals Sa0 to Sa10 input to the contact impedance compensator 93a and the control signals Sb0 to Sb10 input to the contact impedance compensator 93b in the fourth state is the same as that in the third state. FIG. 19 illustrates an example of a waveform obtained in the fourth state. An amplitude V4 of the waveform obtained after amplitude compensation is 50 μVpp. This shows that the amplitude of the input waveform is reproduced.

A formula expressing the amplitude V4 obtained after amplitude compensation is described. The amplitude V4 is expressed by the following formula (12) by using the amplitude V3 obtained before amplitude compensation (in the third state) and a value of the common mode rejection ratio CMRR_sys of the biological signal measurement system of the contact impedance Rc1 of the electrode 48 and the contact impedance Rc2 of the electrode 49:

$$V4 = V3 \times \frac{1}{1-\left(\frac{V_{in\_cm}}{V_{in\_diff}}\right) \times 10^{\left(-\frac{CMRR\_sys}{20}\right)}} = V3 \times Ca \quad \text{formula (12)}$$

The right side of the formula (12) is expressed by using the amplitude compensation coefficient Ca calculated by the bioelectric potential waveform compensator 23c illustrated in FIG. 13. The amplitude compensation coefficient Ca is expressed by the following formula (13) when the coefficient of the amplitude V3 is extracted by comparing the middle and right sides of the formula (12):

$$C_a = \frac{1}{1-\left(\frac{V_{in\_cm}}{V_{in\_diff}}\right) \times 10^{\left(-\frac{CMRR\_sys}{20}\right)}} \quad \text{formula (13)}$$

For example, the amplitude compensation coefficient Ca=2.29 is calculated by using the common mode rejection ratio CMRR_sys=91 dB of the biological signal measurement system, the amplitude of the differential signal Vin_diff=50 µVpp, and the amplitude Vin_cm=1 Vpp of the common-mode signal on the basis of the amplitude V3=22 µVpp, the contact impedance Rc1 of the electrode 48=1000 kΩ, and the contact impedance Rc2 of the electrode 49=10 kΩ. Accordingly, the amplitude obtained after compensation is V4=50 µVpp. This shows that the input waveform is reproduced in the bioelectric potential waveform compensator 23c. The amplitude in the first state may be used instead of the amplitude of the differential signal Vin_diff.

In a case where the amplitude is compensated without using values of the contact impedance Rc1 and Rc2, the amplitude compensation coefficient Ca may be determined by using an amplitude of an obtained waveform measured by inputting a known signal. For example, in a case where an amplitude V3=22 µV is obtained in the third state by inputting a sinusoidal wave having a frequency of 10 Hz and an amplitude Vin_diff of 50 µVpp, the amplitude compensation coefficient Ca used in the bioelectric potential waveform compensator 23c may be calculated as follows: Ca=50 µVpp/22 µVpp=50/22.

As described above, even in a case where contact impedance of the electrode 48 that is the measuring electrode and contact impedance of the electrode 49 that is a reference electrode are not equal to each other, a deterioration of an amplitude of an obtained waveform is improved by amplitude compensation. This makes it possible to measure a bioelectric potential of high signal quality.

Figure 20A:
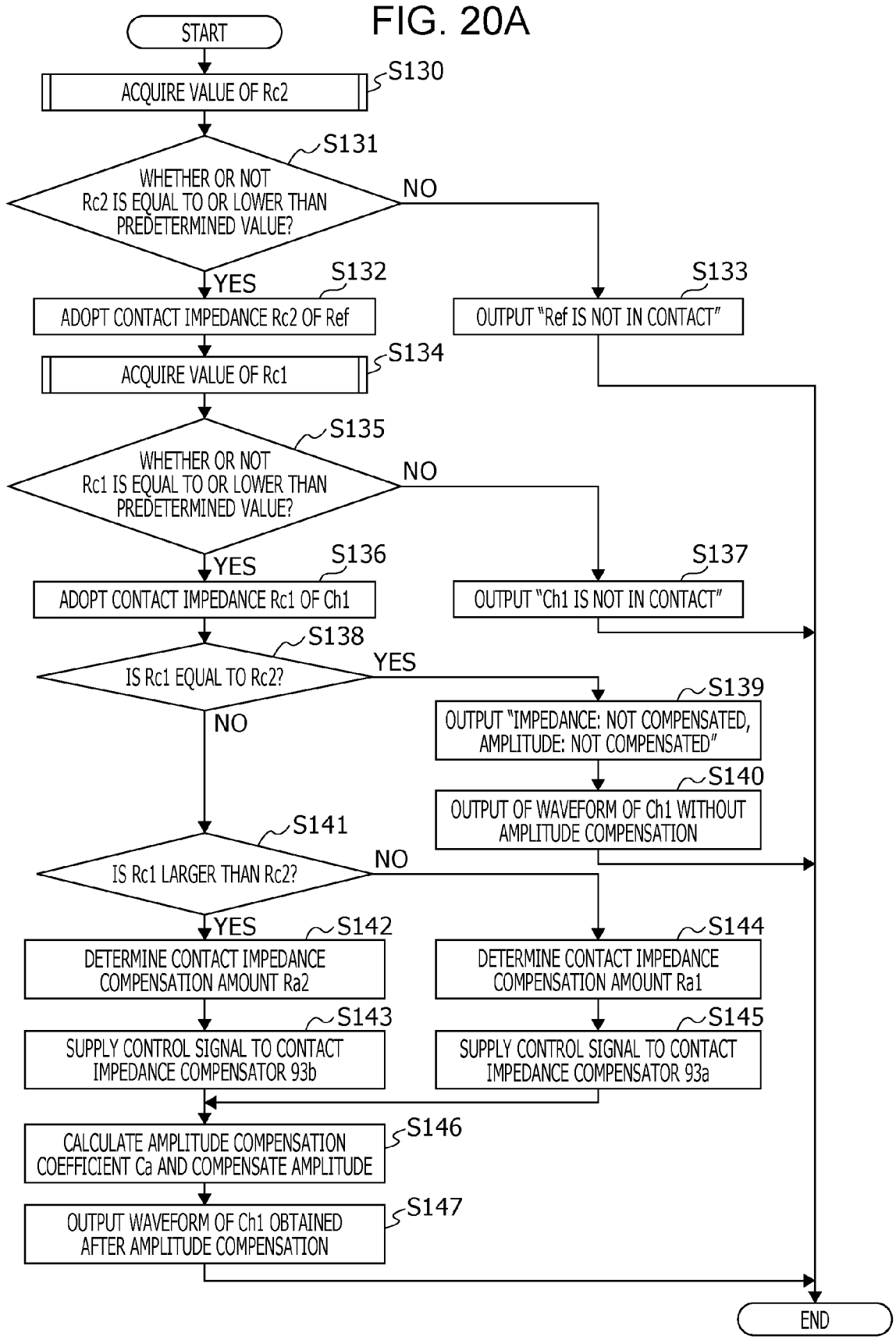
FIG. 20A is a flowchart illustrating a procedure of the contact impedance compensation and amplitude compensation according to Embodiment 1.
Figure 20B:
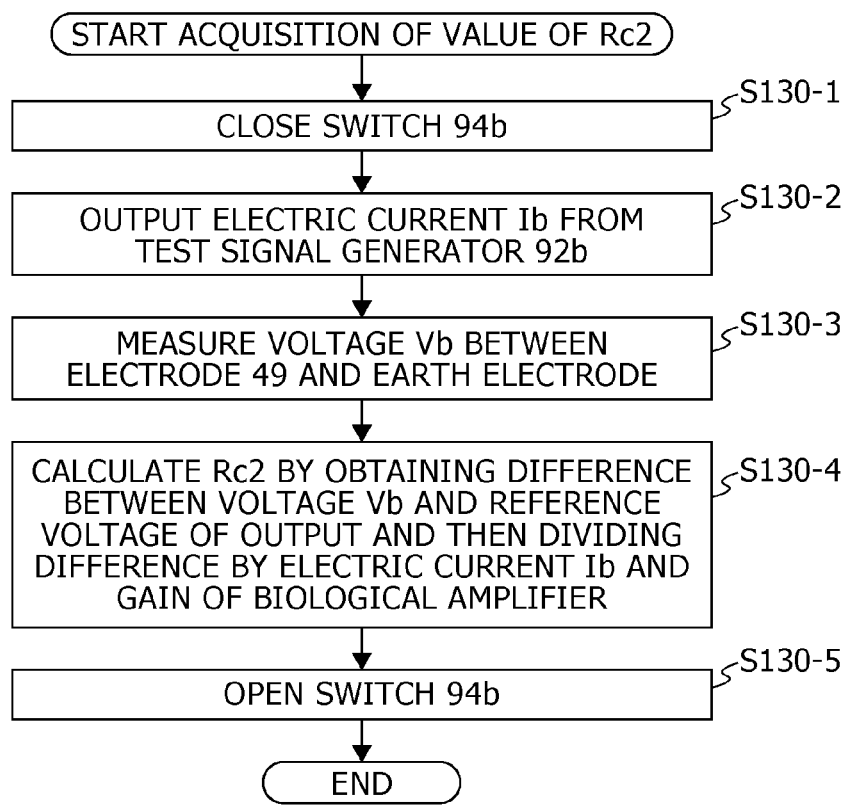
FIG. 20B is a flowchart illustrating a procedure for acquiring contact impedance according to Embodiment 1.
Figure 20C:
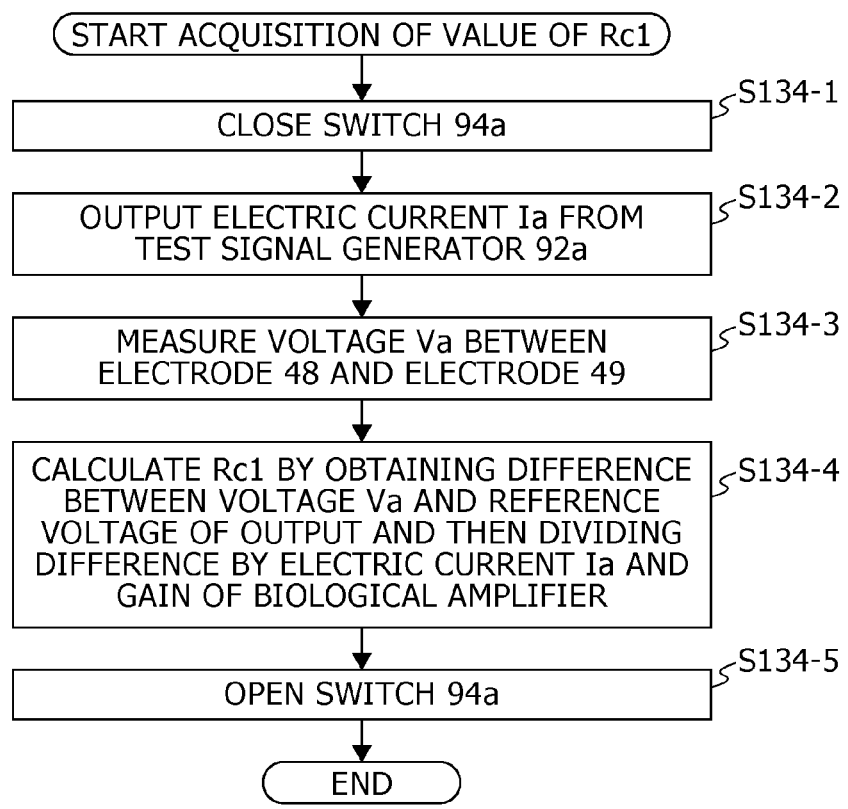
FIG. 20C is a flowchart illustrating a procedure for acquiring contact impedance according to Embodiment 1.

Processing Procedure of Contact Impedance Compensation and Amplitude Compensation FIG. 20A is a flowchart illustrating a procedure of contact impedance compensation and amplitude compensation. FIGS. 20B and 20C are flowcharts illustrating a procedure for acquiring contact impedance.

The processing procedure for acquiring contact impedance and the processing procedure for compensating contact impedance and compensating amplitude are described below with reference to the flowcharts illustrated in FIGS. 20A, 20B, and 20C. Steps S130 through S147 illustrated in FIG. 20A are processes performed by the bioelectric potential processor 23 of FIG. 13.

Step S130

First, a value of contact impedance Rc2 of the electrode 49 that is a reference electrode is acquired. The contact impedance Rc2 is measured by using the test signal generator 92b. FIG. 20B is a flowchart illustrating a procedure for acquiring the contact impedance Rc2.

First, as illustrated in FIG. 20B, a switch 94b provided between a wire coupling the electrode 49 and the contact impedance compensator 93b and the test signal generator 92b is closed by the contact impedance compensation controller 23b (Step S130-1). This causes a test signal to be output from the test signal generator 92b. For example, the test signal generator 92b outputs, as the test signal, a square-wave current Ib having a frequency of 10 Hz and an amplitude of 10 nApp (peak-to-peak) (Step S130-2). Then, a voltage Vb between the electrode 49 and the earth potential is measured by differential amplification of a potential of the electrode 49 and a potential of the earth electrode in the bioelectric potential amplifier 14 while the square-wave current Ib is being output (Step S130-3). Then, a difference between the measured voltage Vb and a reference voltage of output (signal ground) is obtained and is then divided by gain of the biological amplifier and the square-wave current Ib, and thus the contact impedance Rc2 is obtained (Step S130-4). Then, the obtained value of the contact impedance Rc2 is supplied to the bioelectric potential acquisition unit 22 of the information processing apparatus 2 through the bioelectric potential amplifier 14 and the bioelectric potential output unit 15 of the headset 1. Furthermore, the value of the contact impedance Rc2 is supplied from the bioelectric potential acquisition unit 22 to the bioelectric potential processor 23. Then, the switch 94b is opened by the contact impedance compensation controller 23b (Step S130-5). This stops output of the test signal from the test signal generator 92b.

The voltage Vb corresponds to a second voltage according to the present disclosure, and the current Ib corresponds to a second current according to the present disclosure. The contact impedance Rc2 corresponds to a fourth resistance value according to the present disclosure.

Step S131

Next, as illustrated in FIG. 20A, the contact impedance evaluator 23a of the bioelectric potential processor 23 determines whether or not the contact impedance Rc2 (Refz) of the electrode 49 is equal to or lower than a predetermined value on the basis of an output result of the bioelectric potential acquisition unit 22. The predetermined value is, for example, 5 MΩ in a case where the frequency of the test signal is 10 Hz (500 kΩ in a case where the frequency of the test signal is 1 kHz). The contact impedance evaluator 23b determines that the electrode 49 is in contact with skin of the user 10 in a case where the value of the contact impedance Rc2 is equal to or lower than the predetermined value. Meanwhile, the contact impedance evaluator 23b determines that the electrode 49 is completely separated from the skin of the user 10 in a case where the value of the contact impedance Rc2 is larger than the predetermined value.

Step S132

In a case where the contact impedance evaluator 23b determines that the electrode 49 is in contact with skin of the user 10, the contact impedance evaluator 23a uses the value of the contact impedance Rc2 as contact impedance of the electrode 49.

Step S133

In a case where the contact impedance evaluator 23b determines that the electrode 49 is not in contact with skin of the user 10, i.e., in a case where the contact impedance evaluator 23b determines that the electrode 49 is completely separated from the skin of the user 10, a message "Ref is not in contact" is output on the display unit 3 in order to notify the user 10 that the electrode 49 that is a reference electrode is not correctly in contact with the user 10. Display on the display unit 3 will be described later.

Step S134

Next, a value of contact impedance Rc1 of the electrode 48 that is a measuring electrode is acquired. The contact impedance Rc1 is measured by using the test signal generator 92a. A procedure for acquiring the value of the contact impedance Rc1 is similar to the aforementioned procedure for acquiring the value of the contact impedance Rc2. FIG. 20C is a flowchart illustrating the procedure for acquiring the contact impedance Rc1.

First, as illustrated in FIG. 20C, a switch 94a provided between a wire coupling the electrode 49 and the contact impedance compensator 93a and the test signal generator 92a is closed by the contact impedance compensation controller 23a (Step S134-1). This causes a test signal to be output from the test signal generator 92a. For example, the test signal generator 92a outputs, as the test signal, a square-wave current Ia having a frequency of 10 Hz and an amplitude of 10 nApp (peak-to-peak) as in the case of the test signal generator 92b (Step S134-2). Then, a voltage Va between the electrode 48 and the electrode 49 is measured by differential amplification of a potential of the electrode 48 and a potential of the electrode 49 while the square-wave current Ia is being output (Step S134-3). Then, a difference between the measured voltage Va and the reference voltage (signal ground) is obtained and is then divided by gain of the biological amplifier and the square-wave current Ia, and thus the contact impedance Rc1 is obtained (Step S134-4). Then, the obtained value of the contact impedance Rc1 is supplied to the bioelectric potential acquisition unit 22 of the information processing apparatus 2 through the bioelectric potential amplifier 14 and the bioelectric potential output unit 15 of the headset 1. Furthermore, the value of the contact impedance Rc1 is supplied from the bioelectric potential acquisition unit 22 to the bioelectric potential processor 23. Then, the switch 94a is opened by the contact impedance compensation controller 23a (Step S134-5). This stops output of the test signal from the test signal generator 92a.

The voltage Va corresponds to a first voltage according to the present disclosure, and the current Ia corresponds to a first current according to the present disclosure. The contact impedance Rc1 corresponds to a third resistance value according to the present disclosure.

Step S135

Next, as illustrated in FIG. 20A, the contact impedance evaluator 23a of the bioelectric potential processor 23 determines whether or not the contact impedance Rc1 (Ch1z) of the electrode 48 is equal to or lower than a predetermined value (e.g., 5 MΩ) on the basis of an output result of the bioelectric potential acquisition unit 22, as in the case of the electrode 49. The contact impedance evaluator 23b determines that the electrode 48 is in contact with skin of the user 10 in a case where the value of the contact impedance Rc1 is equal to or lower than the predetermined value. Meanwhile, the contact impedance evaluator 23b determines that the electrode 48 is completely separated from the skin of the user 10 in a case where the value of the contact impedance Rc1 is larger than the predetermined value.

Step S136

In a case where the contact impedance evaluator 23b determines that the electrode 48 is in contact with skin of the user 10, the contact impedance evaluator 23a uses the value of the contact impedance Rc1 as contact impedance of the electrode 48.

Step S137

In a case where the contact impedance evaluator 23b determines that the electrode 48 is not in contact with skin of the user 10, i.e., in a case where the contact impedance evaluator 23b determines that the electrode 48 is completely separated from the skin of the user 10, a message "Ch1 is not in contact" is output on the display unit 3 in order to notify the user 10 that the electrode 48 that is a measuring electrode is not correctly in contact with the user 10.

Step S138

In a case where the contact impedance evaluator 23b determines that the electrode 48 and the electrode 49 are in contact with skin of the user 10, the contact impedance evaluator 23a determines whether or not the contact impedance Rc1 of the electrode 48 and the contact impedance Rc2 of the electrode 49 are equal to each other.

Step S139

In a case where the contact impedance evaluator 23a determines that the contact impedance Rc1 of the electrode 48 and the contact impedance Rc2 of the electrode 49 are equal to each other, it is unnecessary to compensate the contact impedance Rc1 of the electrode 48 and the contact impedance Rc2 of the electrode 49. Therefore, a message "impedance: not compensated, amplitude: not compensated" is output on the display unit 3.

Step S140

Furthermore, the bioelectric potential processor 23 outputs a bioelectric potential waveform of the electrode 48 evaluated by the contact impedance evaluator 23a as a bioelectric potential waveform of Ch1 without performing amplitude compensation.

Step S141

In a case where the contact impedance evaluator 23a determines that the contact impedance Rc1 of the electrode 48 and the contact impedance Rc2 of the electrode 49 are not equal to each other, the contact impedance evaluator 23a determines whether or not the contact impedance Rc1 of the electrode 48 is larger than the contact impedance Rc2 of the electrode 49.

Step S142

In a case where the contact impedance Rc1 of the electrode 48 is larger than the contact impedance Rc2 of the electrode 49, the synthetic impedance Rt1 of the electrode 48 and the synthetic impedance Rt2 of the electrode 49 are determined so that Rt1=Rt2=Rc1 is satisfied. The impedance compensation amount Ra2 of the electrode 49 is calculated by Ra2=Rc1−Rc2, and the impedance compensation amount Ra1 of the electrode 48 is determined to be 0 kΩ.

Step S143

When the impedance compensation amount Ra2 of the electrode 49 is determined, the contact impedance compensation controller 23b supplies the control signals Sb0 to Sb10 to the contact impedance compensator 93b for the electrode 49 in accordance with the impedance compensation amount Ra2. This switches the switches SWb0 to SWb10 in the contact impedance compensator 93b. The impedance compensation amount Ra2 is thus given, and the synthetic impedance of the electrode 49 becomes Rc1.

Step S144

In a case where the contact impedance Rc2 of the electrode 49 is larger than the contact impedance Rc1 of the electrode 48, the synthetic impedance Rt1 of the electrode 48 and the synthetic impedance Rt2 of the electrode 49 are determines so that Rt1=Rt2=Rc2 is satisfied. The impedance compensation amount Ra1 of the electrode 48 is calculated by Rc2−Rc1, and the impedance compensation amount Ra2 of the electrode 49 is determined to be 0 kΩ.

Step S145

When the impedance compensation amount Ra1 of the electrode 48 is determined, the contact impedance compensation controller 23a supplies the control signals Sa0 to Sa10 to the contact impedance compensator 93a for the electrode 48 in accordance with the impedance compensation amount Ra1. This switches the switches SWa0 to SWa10 in the contact impedance compensator 93a. The impedance compensation amount Ra1 is thus given, and the synthetic impedance of the electrode 48 becomes Rc2.

Step S146

After impedance compensation, the bioelectric potential processor 23 causes the bioelectric potential waveform compensator 23c to calculate a coefficient for amplitude compensation (amplitude compensation coefficient) Ca on the basis of the formula (13) by using the contact impedance Rc1 of the electrode 48 and the contact impedance Rc2 of the electrode 49. Then, the bioelectric potential waveform compensator 23c compensates the amplitude of a bioelectric potential by using the amplitude compensation coefficient Ca.

Step S147

The bioelectric potential waveform of the electrode 48 obtained after amplitude compensation is processed by the biological signal analyzer 23d and is output. The processing is thus finished.

Patterns of Contact Impedance Compensation

In contact impedance compensation, the synthetic impedance Rt1 of the electrode 48 and the synthetic impedance Rt2 of the electrode 49 need not necessarily strictly satisfy the relationship expressed by the formula (9). Actually, it is necessary to take into consideration accuracy of the resistance elements Ra1 to Ra10 used in the contact impedance compensator 93a and resistance elements Rb1 to Rb10 used in the contact impedance compensator 93b of FIG. 17 and on-resistances of the switches SWa0 to SWa10 and the switches SWb0 to SWb10. Therefore, an allowable error may be set for the synthetic impedance Rt1 of the electrode 48 and the synthetic impedance Rt2 of the electrode 49 (i.e., the impedance compensation amounts Ra1 and Ra2). An allowable error of the synthetic impedance Rt1 and the synthetic impedance Rt2 is set in the following three patterns. For convenience of description, it is assumed that the contact impedance Rc1 of the electrode 48 and the contact impedance Rc2 of the electrode 49 satisfy Rc1=Rc2=10 kΩ in the first state, and the contact impedance Rc1 of the electrode 48 deteriorates in the second state, and setting of the synthetic impedance Rt1 of the electrode 48 and the synthetic impedance Rt2 of the electrode 49 in the third state is described below in the following three patterns.

Figure 21:
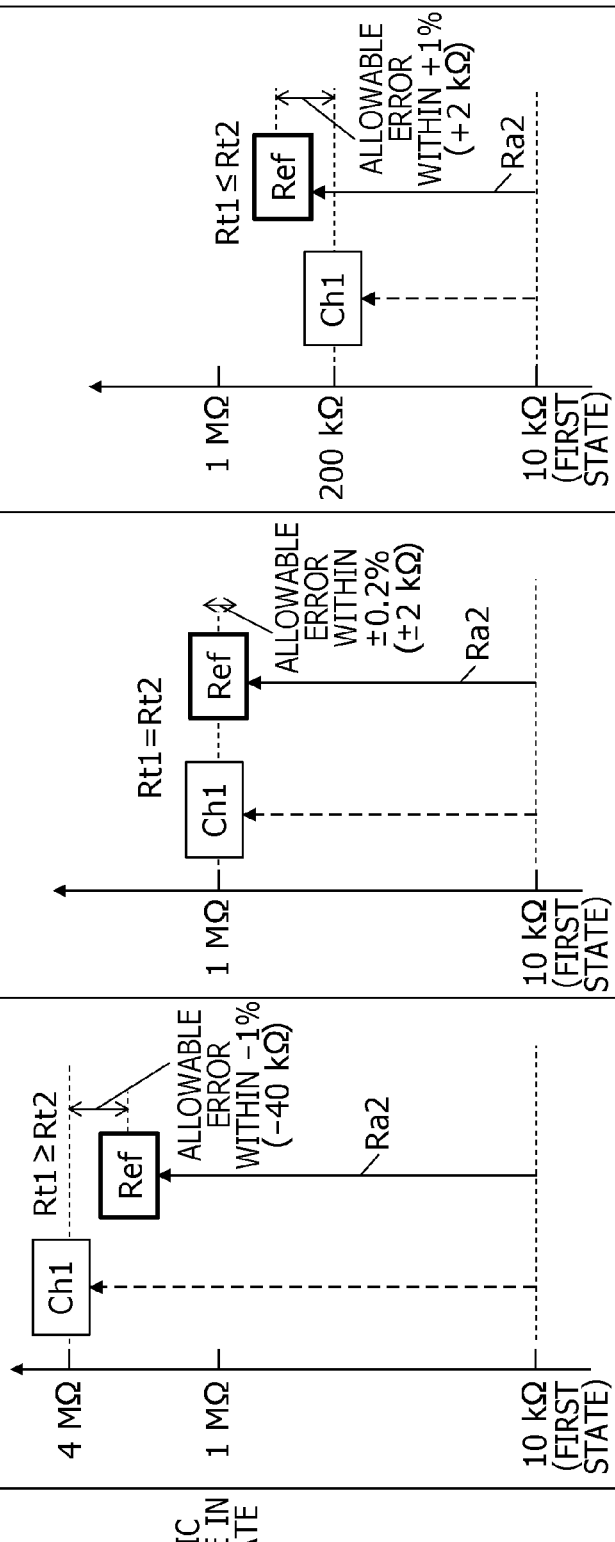
FIG. 21 illustrates a pattern of compensation of contact impedance according to Embodiment 1.

Pattern 1 illustrated in FIG. 21 is a case where the contact impedance Rc1 of the electrode 48 is higher than 1 MΩ (for example, 4 MΩ). Since thermal noise of resistance of 4 MΩ is approximately several μV a temperature of 27° C. and cannot be ignored relative to an amplitude of a biological signal to be obtained, a resistance value (e.g., Rt2=3.96 MΩ to 4.00 MΩ and Ra2=3.95 MΩ to 3.99 MΩ) that is lower by 0% to 1% than the synthetic impedance Rt1 (i.e., Rc1=4 MΩ) of the electrode 48 may be allowed in setting of the synthetic impedance Rt2 of the electrode 49.

Pattern 2 illustrated in FIG. 21 is a most preferable case. Even in this case, an allowable error of the synthetic impedance Rt2 of the electrode 49 is set. In a case where the contact impedance Rc1 of the electrode 48 in the second state is equal to 1 MΩ, the impedance compensation amount Ra2 of the electrode 49 is set to 990 kΩ, and a setting value of the synthetic impedance Rt2 is adjusted to 1 MΩ, which is equal to the synthetic impedance Rt1 of the electrode 48. In this case, an error of 0.2% or less (e.g., Ra2=988 kΩ and Rt2=998 kΩ) may be allowed as to the synthetic impedance Rt2.

Pattern 3 illustrated in FIG. 21 is a case where the contact impedance Rc1 of the electrode 48 is lower than 1 MΩ (for example, 200 kΩ). In this case, thermal noise of resistance is small enough to be ignored, and therefore the synthetic impedance Rt2 of the electrode 49 may be a resistance value (e.g., Rt2=200 kΩ to 202 kΩ and Ra2=190 kΩ to 192 kΩ) that is higher by 0% to 1% than the synthetic impedance Rt1 (i.e., Rt1=200 kΩ) of the electrode 48.

As described above, by setting allowable accuracy of the synthetic impedance Rt1 and the synthetic impedance Rt2 after determining which of Patterns 1 to 3 is applied depending on a value of contact impedance that has deteriorated, a bioelectric potential of high quality can be measured while simplifying the configuration of the contact impedance compensators 93a and 93b and reducing a mounting area of the contact impedance compensators 93a and 93b.

Timing of Measurement of Bioelectric Potential and Contact Impedance

Figure 22:
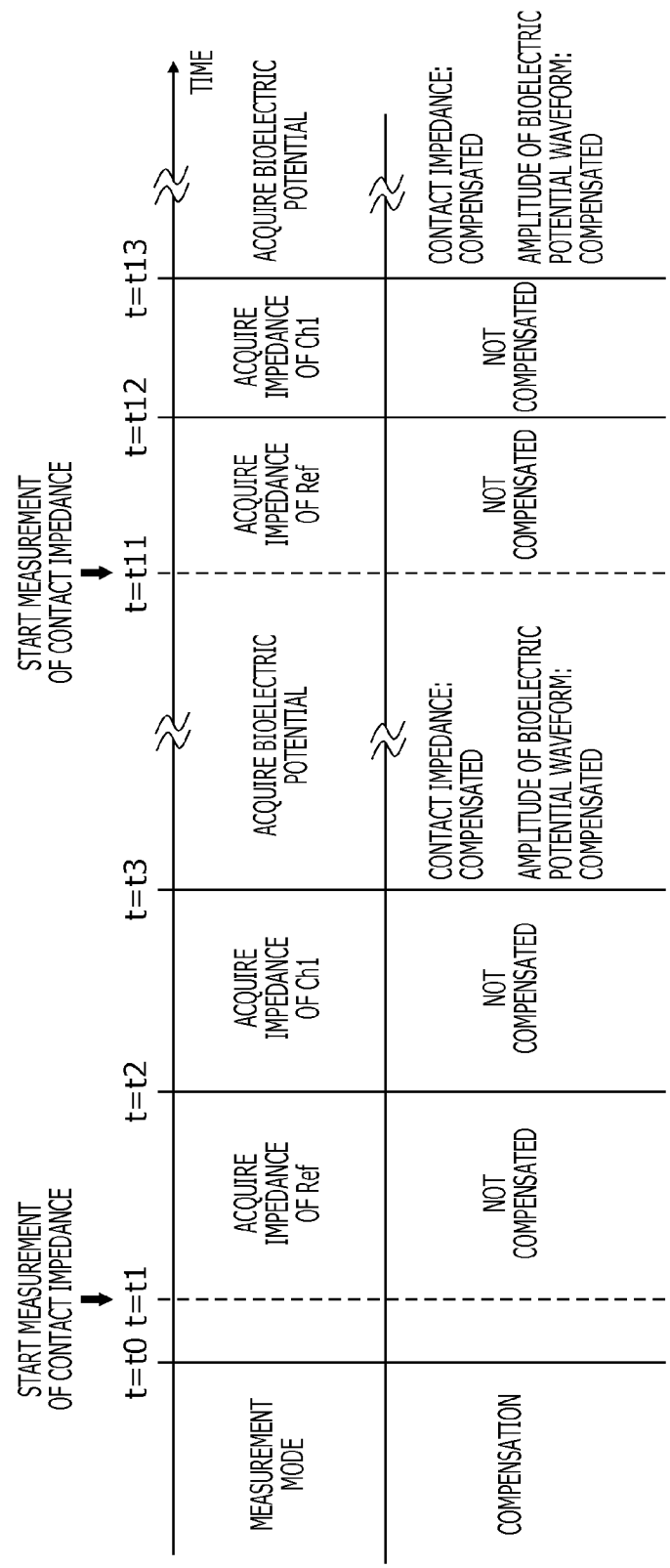
FIG. 22 illustrates an example of a timing of contact impedance compensation according to Embodiment 1.

FIG. 22 illustrates an example of a timing diagram of measurement of a bioelectric potential and contact impedance. FIG. 22 illustrates a case where the contact impedance of the electrode 48 is intermittently measured.

The user 10 wearing the headset 1 activates the headset 1 at a time t=t0 (a time at which the headset is attached may be used as a standard). Then, as illustrated in FIG. 22, the headset 1 starts measurement of contact impedance of the electrode 49 at a time t=t1, and thus the contact impedance Rc2 is obtained. Next, contact impedance of the electrode 48 is measured at a time t=t2, and thus the contact impedance Rc1 is obtained. Then, at a time t=t3, compensation of contact impedance and compensation of an amplitude of a bioelectric potential waveform are performed on the basis of the values of the contact impedance Rc1 and contact impedance Rc2. In this way, a bioelectric potential of the electrode 48 is obtained.

When a contact state of the electrode 48 and the electrode 49 changes thereafter, measurement of contact impedance of the electrode 49 starts again, and the aforementioned measurement is repeated. That is, the contact impedance Rc2 of the electrode 49 is obtained at a time t=t11, the contact impedance Rc1 of the electrode 48 is obtained at a time t=t12, and a bioelectric potential is obtained at a time t=t13.

Figure 23:
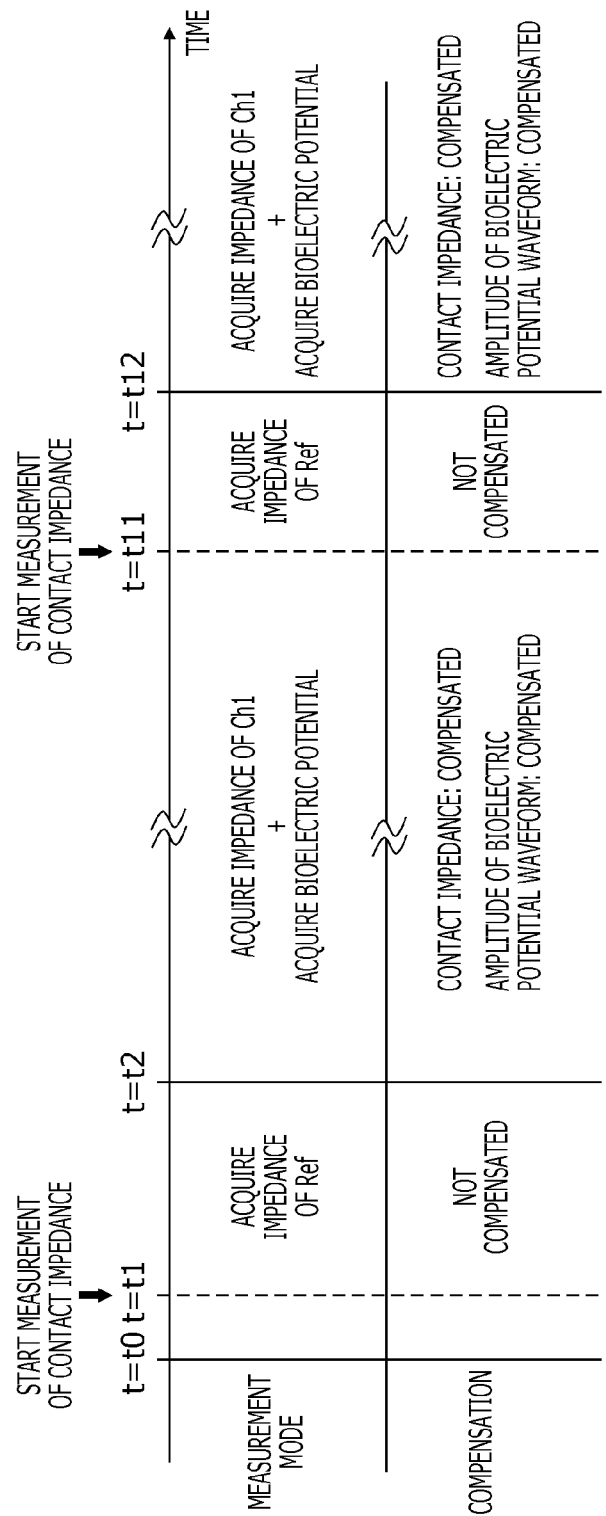
FIG. 23 illustrates another example of a timing of contact impedance compensation according to Embodiment 1.

FIG. 23 illustrates another example of a timing diagram of measurement of a bioelectric potential and contact impedance. FIG. 23 illustrates an example of a case where the contact impedance Rc1 of the electrode 48 and a bioelectric potential are concurrently measured.

The measurement of a bioelectric potential and contact impedance illustrated in FIG. 23 is different from the measurement (intermittent measurement) of contact impedance illustrated in FIG. 22 in that the test signal generator 92a of FIG. 10 outputs, as a test signal, a square-wave current having a frequency of 1 kHz (a value within a frequency band that is different from a frequency band of 0.5 Hz to 100 Hz of a bioelectric potential is selected) and an amplitude of 10 nApp and in that a bioelectric potential is obtained by compensation of the contact impedance Rc1 and compensation of an amplitude of a bioelectric potential waveform concurrently with measurement of the contact impedance Rc1 of the electrode 48 (Ch1) at a time t=t2. Since contact impedance and a bioelectric potential are not concurrently measured by the test signal generator 92b of FIG. 10, a frequency of a square-wave current may be, for example, 10 Hz or 1 kHz as long as the frequency is within a frequency band different from a frequency band of 0.5 Hz to 100 Hz of a bioelectric potential. From a time t=t2 to a time t=t11, the compensation amounts Ra1 and Ra2 of contact impedance and the amplitude compensation coefficient Ca for a bioelectric potential waveform are sequentially updated when the contact impedance Rc1 of the electrode 48 changes, and thus a bioelectric potential can be measured. Concurrent measurement of contact impedance and a bioelectric potential illustrated in FIG. 23 makes it possible to perform more accurate measurement of a bioelectric potential that follows a small fluctuation of the contact impedance Rc1 of the electrode 48 caused, for example, by a change of an ambient environment.

Application Processing

Figure 24:
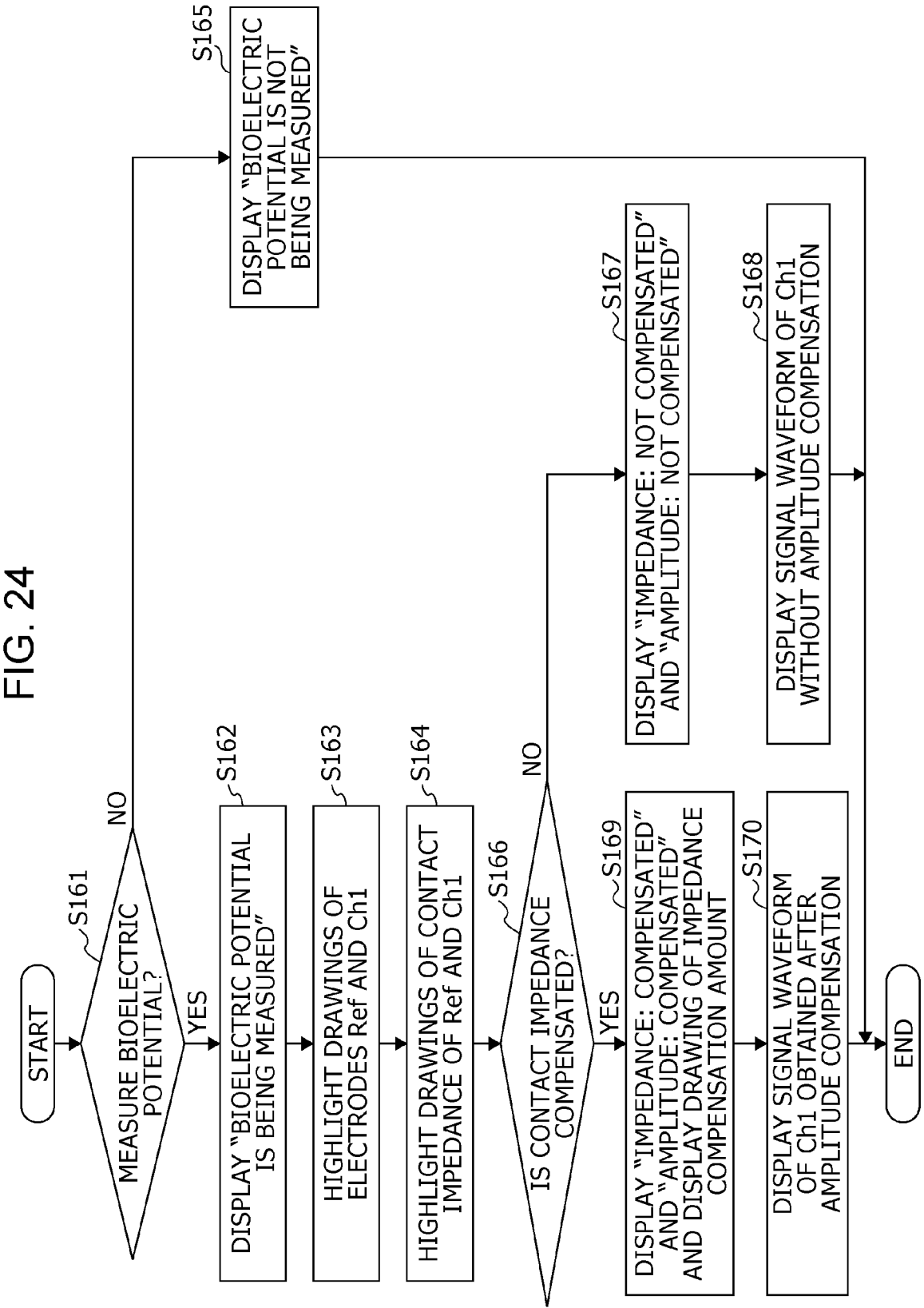
FIG. 24 illustrates a flow of an application processor according to Embodiment 1.

Application processing in measurement of a bioelectric potential using the information processing system 100 is described below. FIG. 24 is a flowchart illustrating a procedure of application processing of biological information by the application processor 26.

As illustrated in FIG. 24, the application processor 26 performs processes in Steps S161 to S170. Steps S161 to Step S170 will be described in detail later. Information processed by the application processor 26 is displayed on display unit 3 as illustrated in FIGS. 25, 26, and 27 after being sent via the display information output unit 27 and the audio information output unit 28 as illustrated in FIG. 6.

Figure 25:
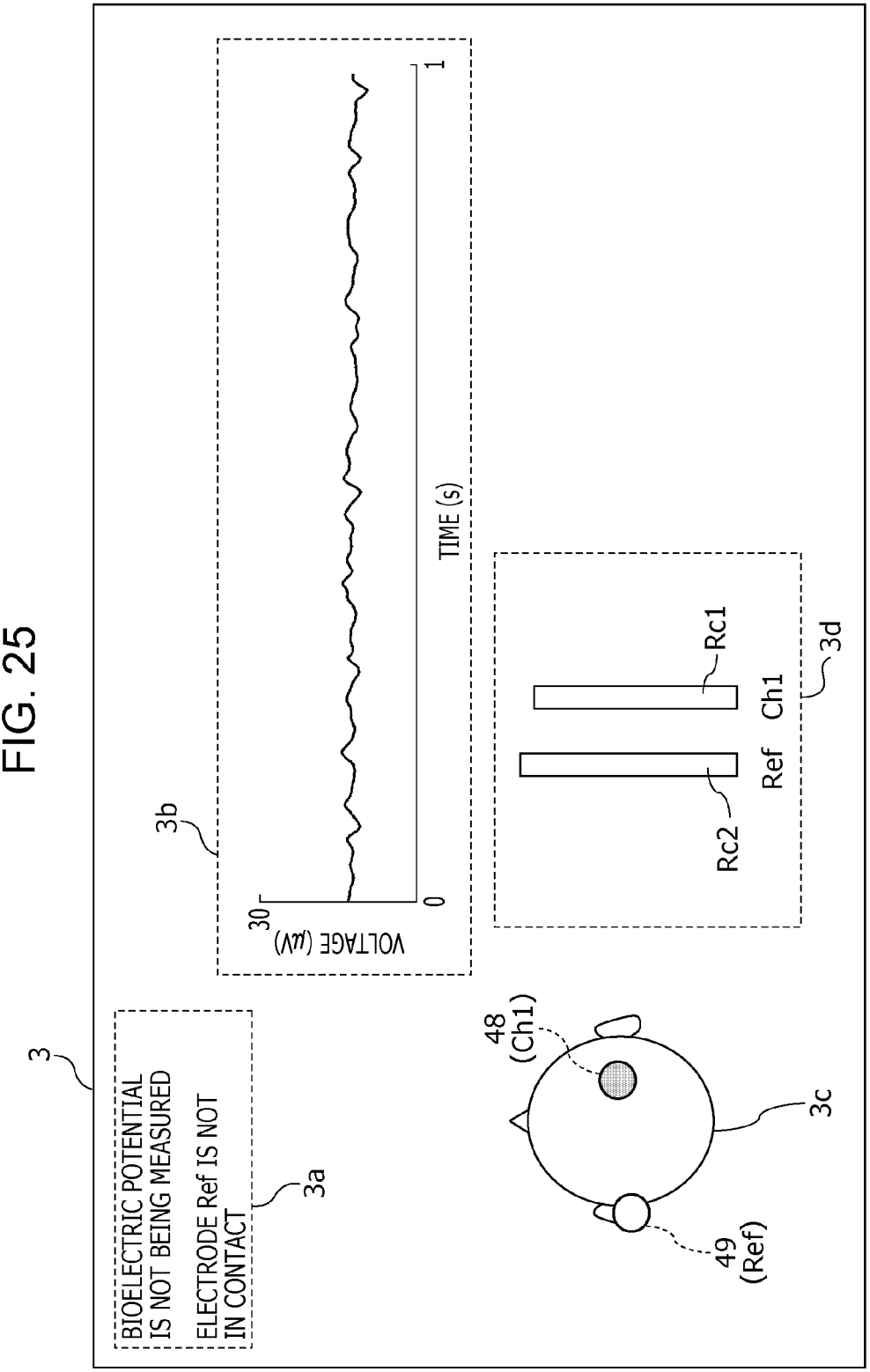
FIG. 25 illustrates information displayed on a screen according to Embodiment 1.
Figure 26:
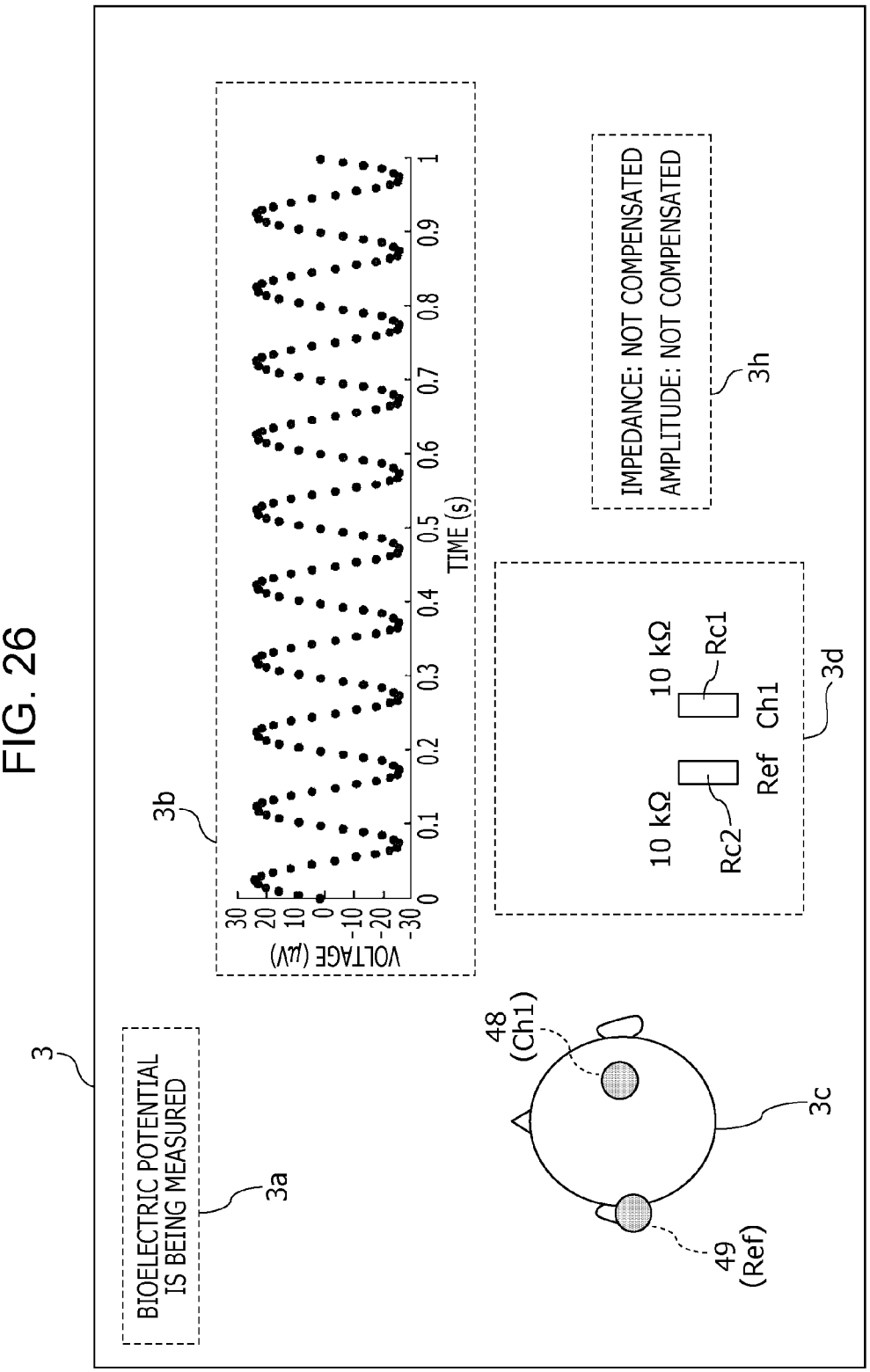
FIG. 26 illustrates information displayed on a screen according to Embodiment 1.
Figure 27:
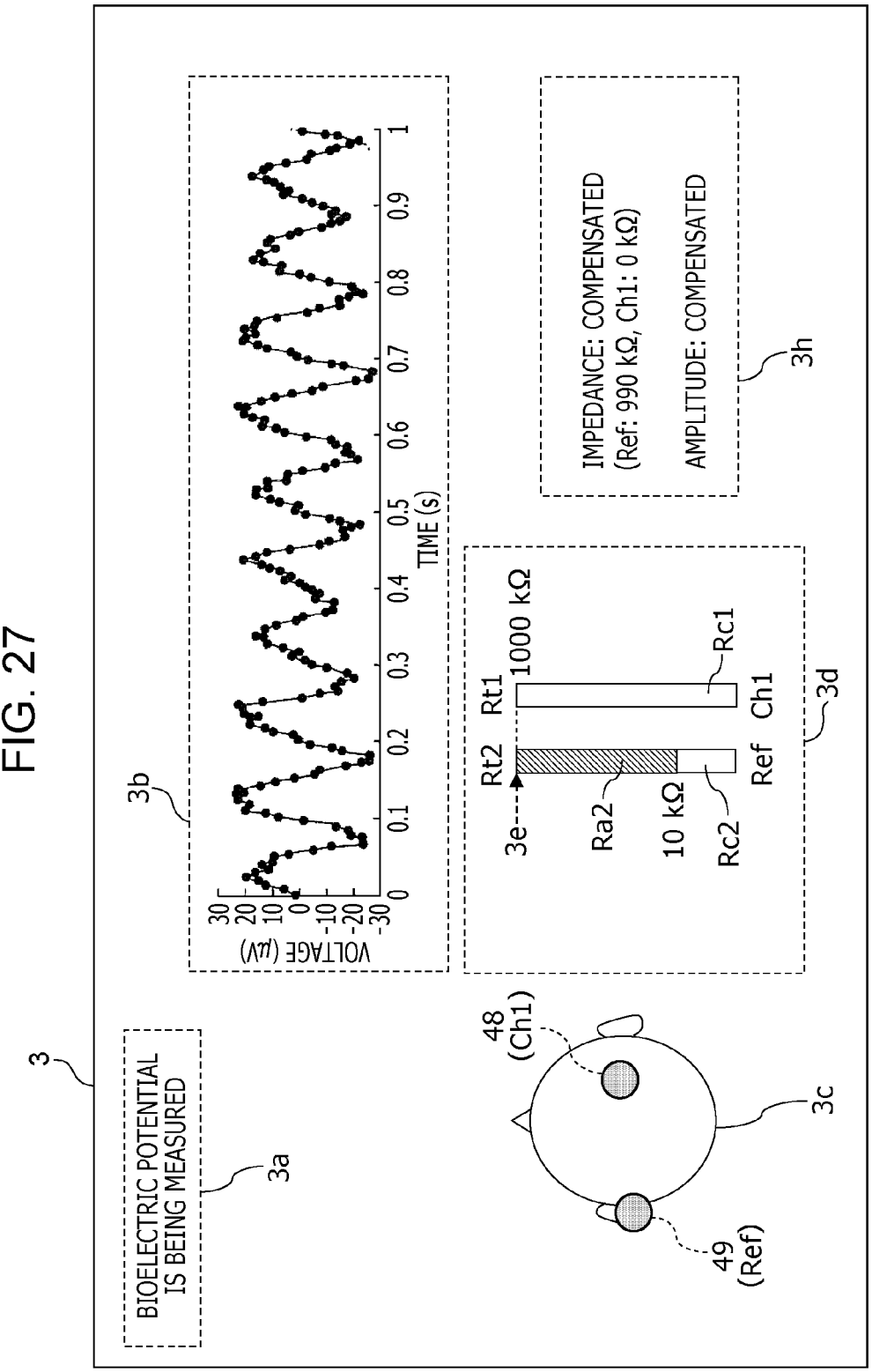
FIG. 27 illustrates information displayed on a screen according to Embodiment 1.

FIGS. 25, 26, and 27 illustrate information displayed on a screen of the information processing system 100.

In FIGS. 25, 26, and 27, information is displayed on the display unit 3. The display unit 3 includes a measurement information display unit 3a, a bioelectric potential waveform display unit 3b, an electrode illustration part 3c, a contact impedance illustration part 3d, and a compensation information display unit 3h.

The measurement information display unit 3a displays a current measurement state of the electrode 48 that is a measuring electrode (Ch1). For example, in a case where the electrode 48 is completely separated from skin of the user 10 and a bioelectric potential is not being measured, messages "bioelectric potential is not being measured" and "electrode Ref is not in contact" are displayed as illustrated in FIG. 25. This makes it possible to notify the user 10 that the electrode 49 is not in contact with skin of the user 10, thereby prompting the user 10 to correctly attach the headset 1.

In the bioelectric potential waveform display unit 3b, a measured bioelectric potential is displayed in chronological order. This allows the user 10 to visually recognize a change in bioelectric potential.

In the electrode illustration part 3c, the electrode 48 and the electrode 49 are displayed in order to show a state of the electrode 48 that is a measuring electrode (Ch1) and a state of the electrode 49 that is a reference electrode (Ref). The electrode illustration part 3c illustrates the headset 1 viewed from the top of the head of the user 10. In the electrode illustration part 3c, contact states of the electrode 48 and the electrode 49 are displayed together with positions of the electrode 48 and the 49 on the body of the user 10. This allows the user 10 to visually recognize which electrode has been displaced, thereby allowing the user 10 to attach the headset 1 at a correct position.

In a case where a bioelectric potential is being measured, not only a bioelectric potential waveform that is currently being measured is displayed in the bioelectric potential waveform display unit 3b, but also corresponding electrode 48 and electrode 49 on the screen may be colored, as illustrated in FIG. 27. In a case where a bioelectric potential is not being measured, the electrode 49 may be displayed in white in the electrode illustration part 3c as illustrated in FIG. 25. A way in which an item is displayed not in white but in color or blinked so as to be distinguishable from others is hereinafter referred to as "highlighted".

In the contact impedance illustration part 3d, contact impedance of the electrode 48 and contact impedance of the electrode 49 are displayed. Furthermore, in the contact impedance illustration part 3d, an impedance compensation amount and synthetic impedance of the electrode 48 and an impedance compensation amount and synthetic impedance of the electrode 49 may be displayed together with the contact impedance. For example, the contact impedance and the impedance compensation amount may be displayed in a continuous graph so that a sum thereof becomes synthetic impedance, as illustrated in FIG. 27. In this case, contact impedance, an impedance compensation amount, and synthetic impedance of the electrode 48 and contact impedance, an impedance compensation amount, and synthetic impedance of the electrode 49 can be displayed in a manner easy to compare by displaying such information concerning the electrode 48 and information concerning the electrode 49 side by side.

In the compensation information display unit 3h, whether or not impedance compensation and amplitude compensation are performed. For example, in a case where impedance compensation is performed, "impedance: compensated" is displayed, and values of impedance compensation amounts of the electrode 48 and the electrode 49 are displayed together, as illustrated in FIGS. 26 and 27. In a case where amplitude compensation is performed, "amplitude: compensated" is displayed. This allows the user 10 to visually recognize whether compensation is performed, the kind of compensation, and a compensation amount of each electrode. The compensation information display unit 3h is useful especially in a case where the user 10 manually compensates impedance.

Steps of the application processing performed by the application processor 26 are described below with reference to display images illustrated in FIGS. 25, 26, and 27.

Step S161

First, the application processor 26 determines whether or not a bioelectric potential is being measured on the basis of an output result of the bioelectric potential processor 23. Specifically, the application processor 26 receives a result of determination as to whether or not the electrode 48 and the electrode 49 are in contact with skin of the user 10 from the contact impedance evaluator 23a of the bioelectric potential processor 23 and determines whether or not a bioelectric potential is being measured by the electrode unit 13 on the basis of the received result of determination.

Step S162

In a case where a bioelectric potential is being measured by the electrode unit 13, the application processor 26 causes the display information output unit 27 to display a message "bioelectric potential is being measured" on the display unit 3. The message "bioelectric potential is being measured" is displayed in the measurement information display unit 3a of the display unit 3.

Step S163

Furthermore, the display information output unit 27 causes the electrodes that are being used for measurement, i.e., the electrode 48 (Ch1) and the electrode 49 (Ref) that is a reference electrode to be displayed in the electrode illustration part 3c in a highlighted manner. For example, drawings of the electrode 48 and the electrode 49 are displayed in the electrode illustration part 3c.

Step S164

In the contact impedance illustration part 3d, drawings of contact impedance are displayed in Rc2 and Rc1 in a highlighted manner in gauge sizes corresponding to a value of the contact impedance Rc1 of the electrode 48 and a value of the contact impedance Rc2 of the electrode 49. For example, in the first state illustrated in FIG. 19, the contact impedance of the electrode 49 (Ref) is 10 kΩ and the contact impedance of the electrode 48 (Ch1) is 10 kΩ, and drawings indicative of these values of contact impedance are displayed in the contact impedance illustration part 3d (Rc2 and Rc1) of FIG. 26.

Step S165

In a case where a bioelectric potential is not being measured by the electrode unit 13, the application processor 26 causes the display information output unit 27 to display a message "bioelectric potential is not being measured" in the measurement information display unit 3a of the display unit 3. In a case where the electrode 49 (Ref) is not in contact with skin of the user 10, a message "electrode Ref is not in contact" is displayed in the measurement information display unit 3a as illustrated in FIG. 25, and then the processing is finished.

Step S166

In a case where a bioelectric potential is being measured by the electrode unit 13, the application processor 26 determines whether or not contact impedance is compensated by the bioelectric potential processor 23, after the contact impedance Rc1 of the electrode 48 and the contact impedance Rc2 of the electrode 49 are displayed. This determination is made on the basis of the control signals Sa0 to Sa10 and the control signals Sb0 to Sb10 generated by the contact impedance compensation controller 23b. For example, it may be determined that contact impedance is compensated in a case where the control signal Sa0 or Sb0 is at an L level, and it may be determined that contact impedance is not compensated in a case where the control signals Sa0 and Sb0 are at an H level.

Step S167

In a case where contact impedance is not compensated by the bioelectric potential processor 23, the application processor 26 causes the display information output unit 27 to display texts "impedance: not compensated" and "amplitude: not compensated" in the compensation information display unit 3h as illustrated in FIG. 26.

Step S168

Next, the application processor 26 causes the display information output unit 27 to display a biological signal waveform of the electrode 48 (Ch1) without amplitude compensation in the bioelectric potential waveform display unit 3b.

Step S169

In a case where contact impedance is compensated by the bioelectric potential processor 23, the application processor 26 causes the display information output unit 27 to display texts "impedance: compensated" and "amplitude: compensated" in the compensation information display unit 3h as illustrated in FIG. 27. In the compensation information display unit 3h, values of the impedance compensation amounts Ra1 and Ra2 are displayed. In the example of FIG. 27, a value of the synthetic impedance Rt2 of the electrode 49 (Ref) is displayed by indicating a position of 1000 kΩ by using the dotted-line arrow in a synthetic impedance illustration part 3e. The impedance compensation amount Ra2=990 kΩ of the electrode 49 (Ref) is displayed in a highlighted manner in the synthetic impedance illustration part 3e.

Step S170

Furthermore, the application processor 26 causes the display information output unit 27 to display a biological signal waveform of the electrode 48 (Ch1) obtained after amplitude compensation in the bioelectric potential waveform display unit 3b.

Effects

As described above, in the information processing system 100 according to the present embodiment, even in a case where the contact impedance Rc1 of the electrode 48 (Ch1) and the contact impedance Rc2 of the electrode 49 (Ref) are not equal to each other, a bioelectric potential of high signal quality can be measured without forcing the user 10 to go to the trouble of attaching the electrodes again, i.e., the trouble of attaching the headset 1 again since compensation of the contact impedance Rc1 and Rc2 and compensation of an amplitude of a bioelectric potential waveform are performed on the basis of the values of the contact impedance Rc1 and Rc2.

Modification 1 of Embodiment 1

Figure 28:
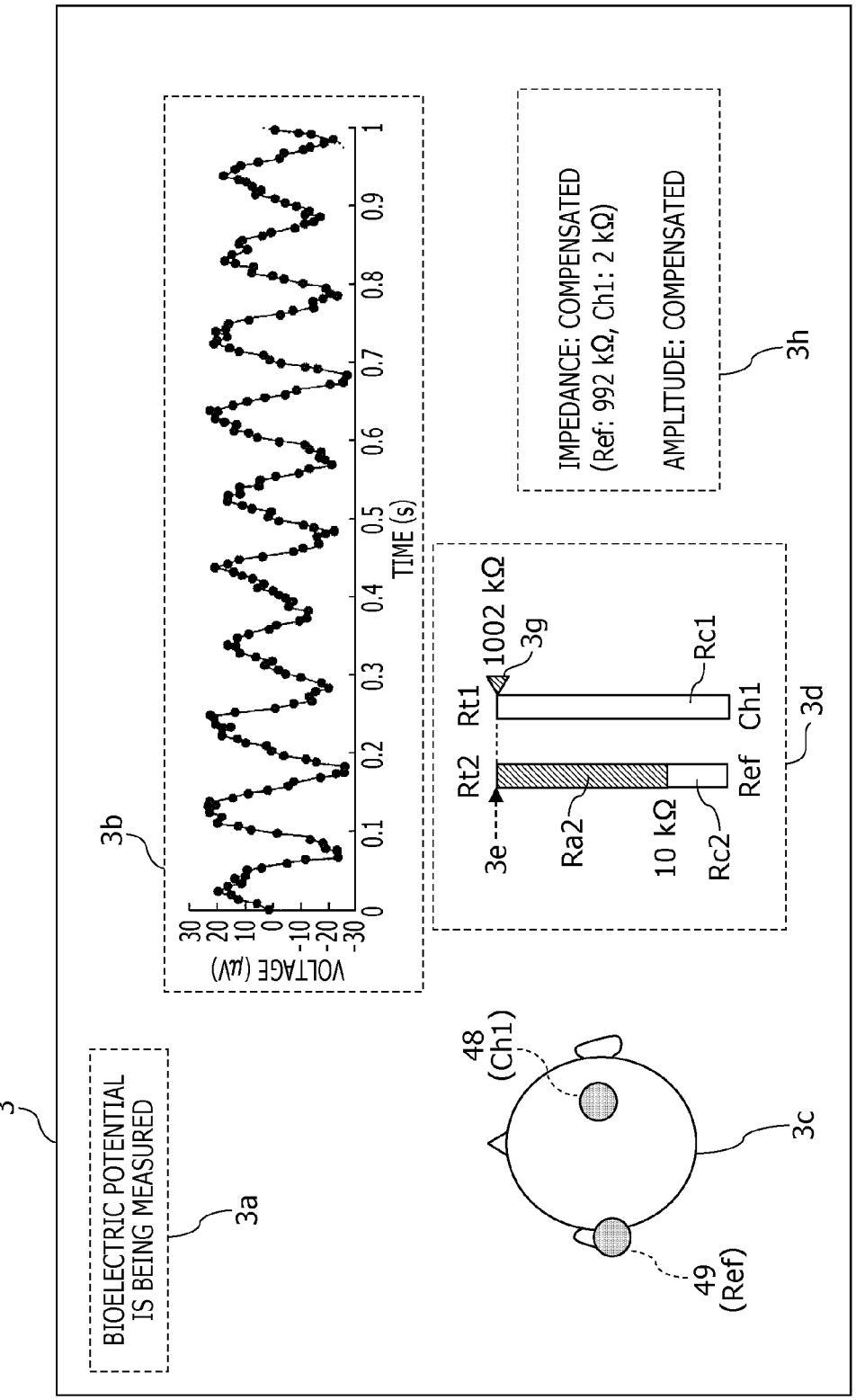
FIG. 28 illustrates information displayed on a screen according to Modification 1 of Embodiment 1.

Next, Modification 1 of Embodiment 1 is described. FIG. 28 illustrates information displayed on the screen of the information processing system 100 according to the present modification.

In the information processing system 100 according to the present modification, a synthetic impedance value can be changed by inputting a value by using the operation input unit 11 of the headset 1, as described above. In a case where the user 10 changes a synthetic impedance value by manually inputting a value by using the operation input unit 11, it is possible to cope with a temporal fluctuation of contact impedance of the electrode 48 (Ch1) and contact impedance of the electrode 49 (Ref).

For example, the operation input unit 11 has a knob 3g for changing synthetic impedance displayed on the display unit 3. The user 10 can change synthetic impedance by adjusting the knob 3g for changing synthetic impedance displayed on the display unit 3 so that a gauge size corresponding to a desired impedance value is displayed.

Specifically, the user 10 changes the synthetic impedance Rt1 of the electrode 48 and the synthetic impedance Rt2 of the electrode 49 by using the knob 3g for changing synthetic impedance as illustrated on the display unit 3 of FIG. 28 in Pattern 2 of contact impedance compensation illustrated in FIG. 21. For example, the user 10 sets the synthetic impedance Rt1 of the electrode 48 and the synthetic impedance Rt2 of the electrode 49 so that Rt1=Rt2=1002 kΩ (the ideal setting value 1000 kΩ of the synthetic impedance with an error of +0.2%). In this example, the impedance compensation amount Ra1 of the electrode 48 (Ch1) is set to 2 kΩ, and the impedance compensation amount Ra2 of the electrode 49 (Ref) is set to 992 kΩ.

In this way, the synthetic impedance can be set higher in advance in consideration of a fluctuation of contact impedance after impedance compensation depending on an actual use situation. This makes it possible to improve user friendliness.

Modification 2 of Embodiment 1

Figure 29:
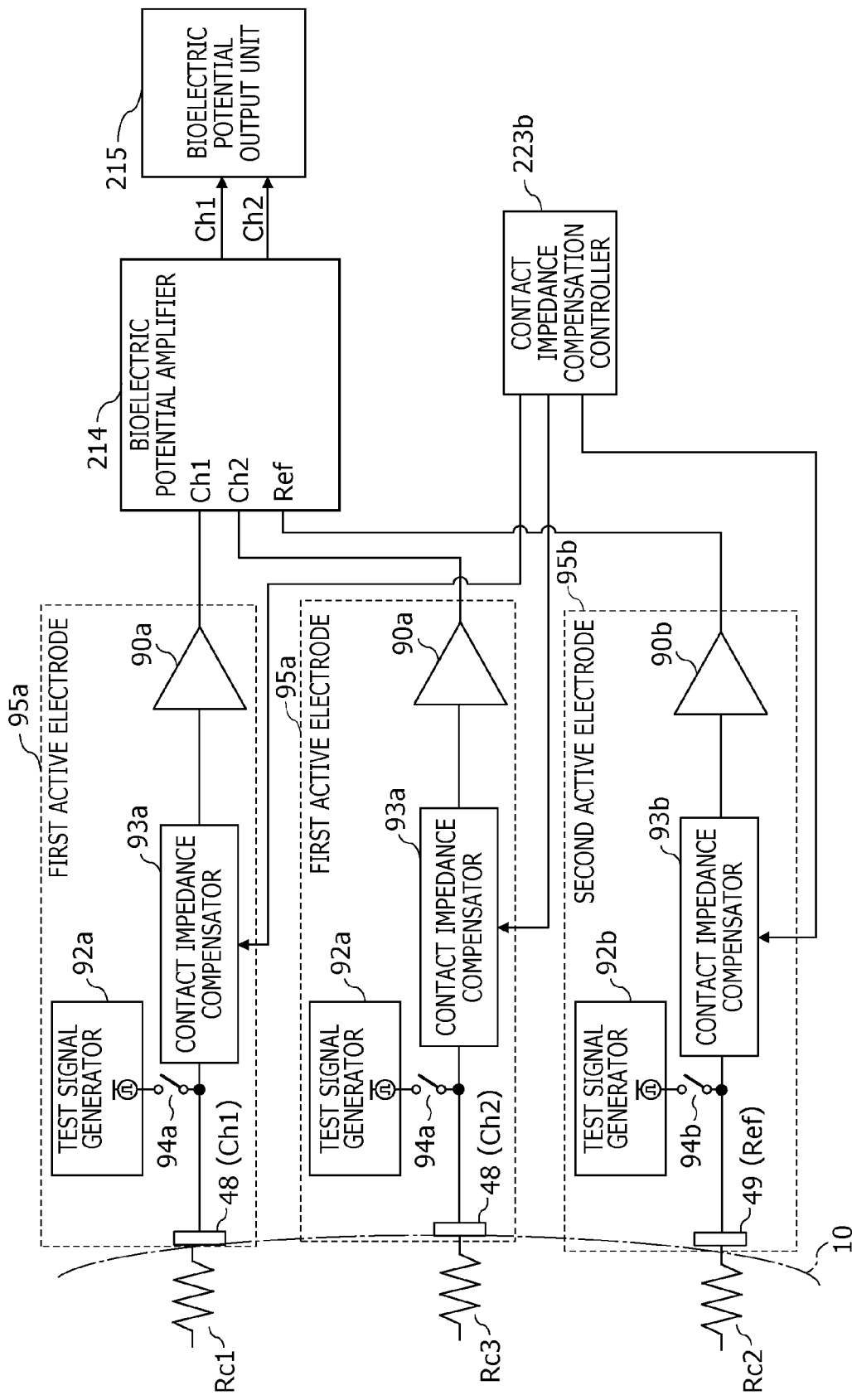
FIG. 29 is a block diagram illustrating a detailed configuration of a bioelectric potential measuring device according to Modification 2 of Embodiment 1.

Next, Modification 2 of Embodiment 1 is described. FIG. 29 is a block diagram illustrating a detailed configuration of a bioelectric potential measuring device according to the present modification.

As illustrated in FIG. 29, the headset 1 may have two or more electrodes 48. In FIG. 29, a first active electrode 95a for the electrode 48 (Ch2) is added to the configuration of the bioelectric potential measuring device 1b illustrated in FIG. 10. The first active electrode 95a for Ch2 includes a test signal generator 92a, a contact impedance compensator 93a, and a buffer 90a, as in the first active electrode 95a for Ch1 illustrated in FIG. 10. An output of the first active electrode 95a for Ch2 is coupled to a bioelectric potential amplifier 214.

Bioelectric potentials of Ch1, Ch2, and Ref are supplied to the bioelectric potential amplifier 214. Differences of a potential signal of Ch1 and a potential signal of Ch2 from a reference potential (Ref) are amplified by the bioelectric potential amplifier 214. Digital data of the bioelectric potentials of Ch1 and Ch2 output from the bioelectric potential amplifier 214 is supplied to a bioelectric potential output unit 215.

The contact impedance compensation controller 223b equalizes synthetic impedance Rc1t of the electrode 48 for Ch1, synthetic impedance Rc2t of the electrode 49 for Ref, and synthetic impedance Rc3t of the electrode 48 for Ch2 to a highest one of contact impedance Rc1, Rc2, and Rc3 on the basis of the contact impedance Ch1z (Rc1) of the electrode 48 for Ch1, Refz (Rc2) of the electrode 49 for Ref, and Ch2z (Rc3) of the electrode 48 for Ch2 that are output from a bioelectric potential evaluator (not illustrated). For example, in a case where Rc1=1 MΩ, Rc2=10 kΩ, and Rc3=10 kΩ, the synthetic impedance Rc1t, synthetic impedance Rc2t, and synthetic impedance Rc3t are determined to be 1 MΩ.

Control signals Sa0 to Sa10 are supplied to each contact impedance compensator 93a so that an impedance compensation amount Ra1 of the electrode 48 for Ch1, an impedance compensation amount Ra2 of the electrode 49 for Ref, and an impedance compensation amount Ra3 of the electrode 48 for Ch2 satisfy Ra1=0 kΩ, Ra2=990 kΩ, and Ra3=990 kΩ. In this case, the formula (9) is established both as for the electrode 48 for Ch1 and the electrode 49 for Ref and as for the electrode 48 for Ch2 and the electrode 49 for Ref, and therefore a common mode rejection ratio of a bioelectric potential measurement system of FIG. 29 is expressed by the formula (11). Accordingly, a degradation of a bioelectric potential waveform caused by hum noise is improved as compared with a state before impedance compensation. Compensation of an amplitude of the bioelectric potential waveform is similar to that in Embodiment 1, and therefore description thereof is omitted.

In the information processing system 100 according to the present modification, a bioelectric potential of high quality can be measured by equalizing contact impedance to a higher value even in a case where a bioelectric potential is measured by using multiple channels.

Compensation of contact impedance and compensation of an amplitude of a bioelectric potential waveform according to the present embodiment and the modifications are applicable not only to the headset 1 for brain wave measurement, but also to a patch-type module for measuring an electrocardiographic potential, a wristband for measuring a muscle potential, or glasses for measuring an ocular potential.

Embodiment 2

Figure 30:
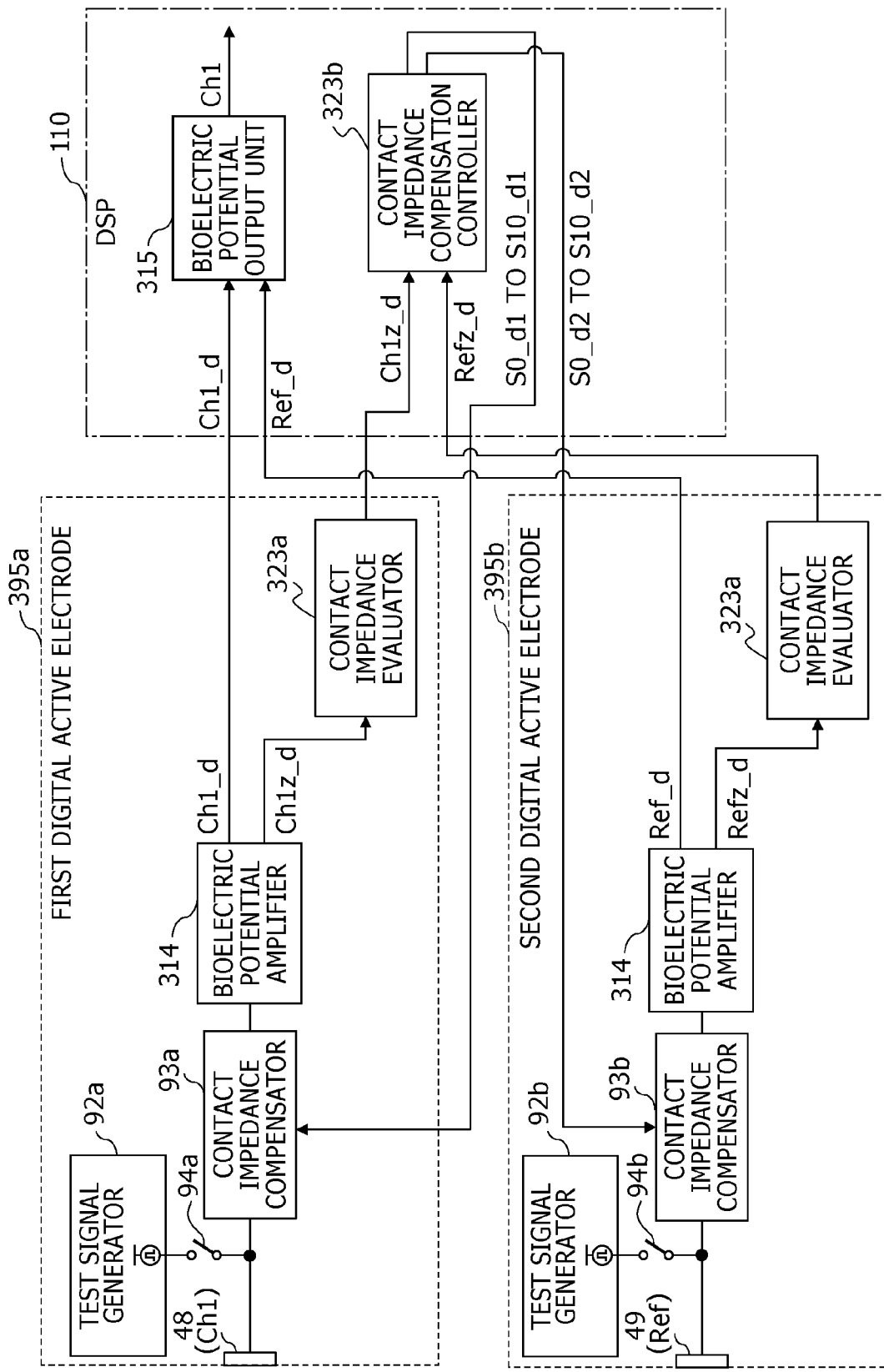
FIG. 30 is a block diagram illustrating a configuration of part of an information processing system according to Embodiment 2.

Next, an information processing system according to Embodiment 2 is described. FIG. 30 is a block diagram illustrating a configuration of part of the information processing system according to the present embodiment.

The information processing system according to the present embodiment is different from the information processing system 100 according to Embodiment 1 in that an electrode 48 and an electrode 49 are digital active electrodes including a contact impedance evaluator. An overall basic configuration of the information processing system according to the present embodiment is identical to the configuration illustrated in FIGS. 6, 7, and 8. Therefore, a first digital active electrode 395a, a second digital active electrode 395b, a contact impedance evaluator 323a, and a contact impedance compensation controller 323b that are differences from Embodiment 1 are described below.

Configuration of Digital Active Electrode

As illustrated in FIG. 30, the first digital active electrode 395a and the second digital active electrode 395b have a configuration for digital output including a bioelectric potential amplifier 314 and the contact impedance evaluator 323a.

The bioelectric potential amplifier 314 disposed in each of the first digital active electrode 395a and the second digital active electrode 395b amplifies a bioelectric potential obtained by an electrode 48 (Ch1) or an electrode 49 (Ref), and the amplified bioelectric potential is converted into a digital code by an A/D converter (not illustrated). The bioelectric potential amplifier 314 for Ch1 may perform differential amplification between Ch1 and a signal (not illustrated) of the same phase as Ch1 (Ref).

The wire from the first active electrode 95a to the bioelectric potential amplifier 14 and the wire from the second active electrode 95b to the bioelectric potential amplifier 14 according to Embodiment 1 illustrated in FIG. 10 are for sending an analog signal and need to be covered with a shield as needed (a ground potential, an earth potential, or the like of the headset 1 is used as a potential of the shield). Meanwhile, a bioelectric potential output from the first digital active electrode 395a according to the present embodiment is a digital value, and therefore it is only necessary to draw a wire so that the digital signal is not impaired. This mitigates restrictions on the wires as compared with analog output, thereby making it possible to more easily achieve multiple channels by increasing the number of electrodes.

The first digital active electrode 395a for Ch1 illustrated in FIG. 30 outputs a digital value Ch1_d of a bioelectric potential Ch1 of the electrode 48 (Ch1) and a digital value Ch1z_d of contact impedance of Ch1.

The second digital active electrode 395b for Ref outputs a digital value Ref_d of a bioelectric potential Ref of Ref and a digital value Refz_d of contact impedance of the electrode 49. A bioelectric potential output unit 315 obtains a difference between the digital values Ch1_d and Ref_d of the respective bioelectric potentials Ch1 and Ref and outputs the bioelectric potential Ch1 of Ch1 obtained after subtraction.

The contact impedance compensation controller 323b compensates contact impedance according to a flow similar to the flow of FIG. 20A on the basis of the digital value Ch1z_d of the contact impedance of Ch1 and the digital value Refz_d of the contact impedance of Ref and supplies control signals S0_d1 to S10_d1 and control signals S0_d2 to S10_d2 to the contact impedance compensators 93a and 93b, respectively. A flow of impedance compensation and a flow of waveform compensation are similar to those in Embodiment 1, and therefore description thereof is omitted.

The contact impedance Ch1z_d of Ch1 and the contact impedance Refz_d of Ref can be measured with higher accuracy and at a higher speed by increasing resolution and sampling frequency of digital output of the first digital active electrode 395a and the second digital active electrode 395b.

This allows contact impedance compensation and amplitude compensation to follow a change of a contact state better than Embodiment 1.

The bioelectric potential output unit 315, the contact impedance compensation controller 323b, and a following digital signal processing block may be realized on a DSP as illustrated in FIG. 30. The first digital active electrode 395a and the DSP 110 of FIG. 30 exchange digital signals Ch1_d, Ch1z_d, and S0_d1 to S10_d1 through a serial interface such as an SPI. The second digital active electrode 395b and the DSP 110 exchange digital signals Ref_d, Refz_d, and S0_d2 to S10_d2 through a serial interface such as an SPI. Since the digital signals can be collectively exchanged through the serial interface, functions of the DSP 110 can be realized by a commercially available microcomputer (MCU).

Effects

As described above, according to the information processing system according to the present embodiment, an electrode unit includes active electrodes for digital output (digital active electrodes). Since the contact impedance compensator 93a is provided in each active electrode, it is possible to improve freedom of a wire variation, thereby increasing expandability of the bioelectric potential measurement system.

In the above embodiments, an information processing apparatus, an information processing system, and an information processing method have been described as one aspect of the present disclosure. However, the present disclosure may be a program for causing a computer to execute the above information processing method. The present disclosure may be a digital signal representing the computer program.

The present disclosure may be a computer-readable non-transitory recording medium such as a flexible disc, a hard disk, a CD-ROM, an MO, a DVD, a DVD-ROM, a DVD-RAM, a BD (Blu-ray (Registered Trademark) Disc), or a semiconductor memory on which the computer program or the digital signal is recorded. Alternatively, the present disclosure may be the digital signal recorded on such a non-transitory recording medium.

The present disclosure may be the computer program or the digital signal transmitted over a telecommunication line, wireless or wired communication line, a network such as the Internet, or data broadcasting.

The present disclosure may be a computer system including a microprocessor and a memory, wherein the memory stores therein the computer program, and the microprocessor operates in accordance with the computer program.

The program or the digital signal may be executed by another independent computer system by being transferred on the aforementioned non-transitory recording medium or by being transferred over the network or the like.

The information processing apparatus, the information processing system, the information processing method, and the computer program according to the embodiments of the present disclosure have been described above. However, the present disclosure is not limited to the above embodiments.

For example, in the above embodiments, a brain wave is assumed as a bioelectric potential to be measured. However, a bioelectric potential to be measured is not limited to a brain wave, and may be an electrocardiographic wave or may be other biological information. In this case, the shape of the electronic apparatus is not limited to a headphone-type or a band-type and may be a different shape depending on a position where the electronic apparatus is attached.

Contact impedance measured by a measuring electrode may be compensated or contact impedance measured by a reference electrode may be compensated.

The electrodes may be active electrodes including an amplifier or may be digital active electrodes that can convert a biological signal into a digital value.

It is only necessary that at least one measuring electrode and at least one reference electrode be provided, and a plurality of measuring electrodes and a plurality of reference electrodes may be provided.

The electronic apparatus and the information processing apparatus may be coupled through a wire or may be coupled wirelessly. The information processing apparatus and the display may be coupled through a wire or may be coupled wirelessly.

The steps in the above embodiments may be changed or omitted. The steps may be performed in a different order.

Furthermore, the above embodiments may be combined.

An information processing system according to the present disclosure has a bioelectric potential measuring device and is useful as a health monitoring apparatus or the like. Furthermore, the information processing system according to the present disclosure is applicable for use as an educational apparatus or the like.

What is claimed is:

1. An electronic apparatus comprising:
a measuring electrode configured to be in contact with first skin of a user;
a reference electrode configured to be in contact with second skin of the user;
a first amplifier circuit;
a second amplifier circuit;
a first compensation circuit including first short lines, first resistances, a first terminal coupled to the measuring electrode, and a second terminal coupled to the first amplifier circuit, each of the first short lines corresponding to a respective one of the first resistances;
a second compensation circuit including second short lines, second resistances, a third terminal coupled to the reference electrode, and a fourth terminal coupled to the second amplifier circuit, each of the second short lines corresponding to a respective one of the second resistances; and
a controller,
wherein the first compensation circuit selects one or more of the first short lines, and thereby a first resistance value between the first terminal and the second terminal is set,
wherein the second compensation circuit selects one or more of the second short lines, and thereby a second resistance value between the third terminal and the fourth terminal is set,
wherein a first sum of a third resistance value between the measuring electrode and the first skin and the first resistance value is equal to a second sum of a fourth resistance value between the reference electrode and the second skin and the second resistance.

2. The electronic apparatus according to claim 1, further comprising:
a first test circuit that is coupled to the measuring electrode and includes a first current source; and
a second test circuit that is coupled to the reference electrode and includes a second current source,
wherein the controller causes the first current source to output a first current, causes the first amplifier circuit measure a first voltage while the first current is being output, and calculates the third resistance value by using a current value of the first current and a voltage value of the first voltage, and wherein the controller causes the second current source to output a second current, causes the second amplifier circuit to measure a second voltage while the second current is being output, and calculates the fourth resistance value by using a current value of the second current and a voltage value of the second voltage.

3. The electronic apparatus according to claim 1, further comprising a third compensation circuit that determines a coefficient of compensation of an amplitude of a bioelectric potential on a basis of the third resistance value and the fourth resistance value and compensates the amplitude of the bioelectric potential.

4. The electronic apparatus according to claim 3, further comprising an operation input unit, wherein the first sum of the third resistance value and the first resistance value is received by the operation input unit, and wherein the second sum of the fourth resistance value and the second resistance is received by the operation input unit.

5. The electronic apparatus according to claim 3, wherein the third compensation circuit determines the coefficient of compensation of the amplitude of the bioelectric potential on a basis of a common mode rejection ratio that indicates a degree of removing a signal common to the second terminal and the fourth terminal.

6. The electronic apparatus according to claim 1, wherein a first active electrode includes the measuring electrode and the first amplifier circuit, a second active electrode includes the reference electrode and the second amplifier circuit, the first active electrode further includes a first test circuit and the first compensation circuit, and the second active electrode further includes a second test circuit and the second compensation circuit.

7. The electronic apparatus according to claim 6, wherein the measuring electrode and the reference electrode each further include an A/D converter and the controller.

8. The electronic apparatus according to claim 6, wherein the first active electrode further includes a coupling pad that couples the measuring electrode to the first compensation circuit, the second active electrode further includes a coupling pad that couples the reference electrode to the second compensation circuit, the first active electrode and the second active electrode each fit within a first circle having a diameter D;

the coupling pad of the measuring electrode and the coupling pad of the reference electrode each have a size that fits within a second circle having a diameter P; and D≥P+T+C+A is satisfied where T is a length of the first test circuit and the second test circuit in a direction normal to the first circle, C is a length of the first compensation circuit and the second compensation circuit in the direction normal to the first circle, and A is a length of the first amplifier circuit and the second amplifier circuit in the direction normal to the first circle.

9. The electronic apparatus according to claim 1, wherein the measuring electrode includes a coupling pad that couples the measuring electrode to the first compensation circuit;

the reference electrode includes a coupling pad that couples the reference electrode to the second compensation circuit;

the measuring electrode and the reference electrode each have a size that fits within a first circle having a diameter D;

the coupling pad of the measuring electrode and the coupling pad of the reference electrode each have a size that fits within a second circle having a diameter P; and D≥P+T+C is satisfied where T is a length of the first test circuit and the second test circuit in a direction normal to the first circle, and C is a length of the first compensation circuit and the second compensation circuit in the direction normal to the first circle.

* * * * *